(12) United States Patent
Simon et al.

(10) Patent No.: US 10,279,163 B2
(45) Date of Patent: May 7, 2019

(54) ELECTRICAL AND MAGNETIC STIMULATORS USED TO TREAT MIGRAINE/SINUS HEADACHE, RHINITIS, SINUSITIS, RHINOSINUSITIS, AND COMORBID DISORDERS

(71) Applicant: ElectroCore, LLC, Basking Ridge, NJ (US)

(72) Inventors: Bruce J. Simon, Mountain Lakes, NJ (US); Joseph P. Errico, Warren, NJ (US); John T. Raffle, Austin, TX (US)

(73) Assignee: Electrocore, Inc., Basking Ridge, NJ (US)

( * ) Notice: Subject to any disclaimer, the term of this patent is extended or adjusted under 35 U.S.C. 154(b) by 0 days.

(21) Appl. No.: 14/217,762

(22) Filed: Mar. 18, 2014

(65) Prior Publication Data
US 2015/0265836 A1 Sep. 24, 2015
US 2016/0361540 A9 Dec. 15, 2016

Related U.S. Application Data

(63) Continuation of application No. 13/183,721, filed on Jul. 15, 2011, now Pat. No. 8,676,324, which is a (Continued)

(51) Int. Cl.
*A61N 1/05* (2006.01)
*A61N 1/04* (2006.01)
(Continued)

(52) U.S. Cl.
CPC ....... *A61N 1/0456* (2013.01); *A61N 1/36014* (2013.01); *A61N 1/36021* (2013.01);
(Continued)

(58) Field of Classification Search
CPC ............ A61N 1/36017; A61N 1/36021; A61N 1/36025; A61N 1/0456; A61N 1/36053
See application file for complete search history.

(56) References Cited

U.S. PATENT DOCUMENTS 3,590,810 A 7/1971 Kopecky
4,196,737 A 4/1980 Bevilacqua
(Continued)

FOREIGN PATENT DOCUMENTS

EP 2777764 8/2015
KR 101242190 3/2013
(Continued)

OTHER PUBLICATIONS

Greicius et al., Functional connectivity in the resting brain: A network analysis of the default mode hypothesis, PNAS, Jan. 2003, vol. 100, No. 1, pp. 253-258.
(Continued)

*Primary Examiner* — Michael J D Abreu
(74) *Attorney, Agent, or Firm* — Dentons US LLP

(57) ABSTRACT

Transcutaneous electrical nerve stimulation devices and magnetic stimulation devices are disclosed, along with methods of treating medical disorders using energy that is delivered noninvasively by such devices. The disorders comprise migraine and other primary headaches such as cluster headaches, including nasal or paranasal sinus symptoms that resemble an immune-mediated response ("sinus" headaches). The devices and methods may also be used to treat rhinitis, sinusitis, or rhinosinusitis, irrespective of whether those disorders are co-morbid with a headache. They may also be used to treat other disorders that may be co-morbid with migraine or cluster headaches, such as anxiety disorders. In preferred embodiments of the disclosed methods, one or both of the patient's vagus nerves are stimulated non-invasively. In other embodiments, parts of
(Continued)

the sympathetic nervous system and/or the adrenal glands are stimulated.

35 Claims, 10 Drawing Sheets

Related U.S. Application Data continuation-in-part of application No. 13/109,250, filed on May 17, 2011, now Pat. No. 8,676,330, which is a continuation-in-part of application No. 13/075,746, filed on Mar. 30, 2011, now Pat. No. 8,874,205.

(60) Provisional application No. 61/451,259, filed on Mar. 10, 2011, provisional application No. 61/471,405, filed on Apr. 4, 2011.

(51) Int. Cl.
*A61N 2/02* (2006.01)
*A61N 1/36* (2006.01)
*A61N 2/00* (2006.01)
*A61N 1/40* (2006.01)

(52) U.S. Cl.
CPC ........... *A61N 1/36053* (2013.01); *A61N 1/40* (2013.01); *A61N 2/002* (2013.01); *A61N 2/006* (2013.01); *A61N 2/008* (2013.01); *A61N 2/02* (2013.01); *A61N 1/36025* (2013.01)

(56) References Cited

U.S. PATENT DOCUMENTS

| | | | |
|---|---|---|---|
| 4,989,605 A | 2/1991 | Rossen | |
| 5,458,141 A | 10/1995 | Neil | |
| 5,899,922 A | 5/1999 | Loos | |
| 5,983,131 A | 11/1999 | Weaver et al. | |
| 6,341,236 B1 | 1/2002 | Osorio et al. | |
| 6,449,507 B1* | 9/2002 | Hill ................. | A61N 1/056 128/898 |
| 6,463,327 B1 | 10/2002 | Lurie et al. | |
| 6,587,719 B1 | 7/2003 | Barrett et al. | |
| 6,610,713 B2 | 8/2003 | Tracey | |
| 7,734,340 B2 | 6/2010 | De Ridder | |
| 7,797,041 B2 | 9/2010 | Libbus et al. | |
| 2002/0099417 A1 | 7/2002 | Naritoku et al. | |
| 2002/0183237 A1 | 12/2002 | Puskas | |
| 2003/0212311 A1 | 11/2003 | Nova et al. | |
| 2004/0073271 A1 | 4/2004 | Harry et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 | 5/2005 | Fox et al. | |
| 2005/0137644 A1 | 6/2005 | Boveja et al. | |
| 2005/0216062 A1 | 9/2005 | Herbst | |
| 2005/0267544 A1 | 12/2005 | Lee et al. | |
| 2006/0074284 A1 | 4/2006 | Juola et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0106337 A1 | 5/2007 | Errico et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0150027 A1* | 6/2007 | Rogers ................. | A61N 1/0456 607/55 |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0077192 A1 | 3/2008 | Harry et al. | |
| 2008/0114199 A1 | 5/2008 | Riehl et al. | |
| 2008/0132964 A1 | 6/2008 | Cohen et al. | |
| 2008/0177190 A1 | 7/2008 | Libbus et al. | |
| 2008/0208266 A1* | 8/2008 | Lesser ................. | A61N 1/36114 607/2 |
| 2008/0306325 A1 | 12/2008 | Burnett et al. | |
| 2009/0112283 A1 | 4/2009 | Kriksunov et al. | |
| 2009/0132018 A1 | 5/2009 | DiUbaldi et al. | |
| 2009/0157149 A1 | 6/2009 | Wahlgren et al. | |
| 2009/0234417 A1 | 9/2009 | Pastena et al. | |
| 2009/0234419 A1 | 9/2009 | Maschino et al. | |
| 2009/0240297 A1 | 9/2009 | Shavit et al. | |
| 2009/0287035 A1 | 11/2009 | Dietrich et al. | |
| 2010/0030299 A1* | 2/2010 | Covalin ................. | A61N 1/0456 607/46 |
| 2010/0152794 A1 | 6/2010 | Radivojevic et al. | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1* | 9/2011 | Simon et al. ................. | 600/9 |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0245486 A1 | 9/2013 | Simon et al. | |
| 2014/0005743 A1 | 1/2014 | Giuffrida et al. | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| WO | WO 1993/01862 | 2/1993 |
| WO | WO2005/007120 | 1/2005 |
| WO | WO2007/092062 | 8/2007 |
| WO | WO2008/042902 | 4/2008 |
| WO | WO2007/058780 | 5/2008 |
| WO | WO 2009/021080 | 2/2009 |
| WO | WO 2009/135693 | 11/2009 |
| WO | WO2013066135 | 5/2013 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

Europe Office Action dated Apr. 24, 2018 in related Application No. 15796247.3 filed May 20, 2015 (6 pages).

KR101242190 dated Mar. 25, 2013, Espacenet computer generated English translation (11 pages).

(56) References Cited

OTHER PUBLICATIONS

International Search Report and Written Opinion dated Aug. 25, 2015 in related Application No. PCT/US15/31847 filed May 20, 2015 (10 pages).
Europe Office Action dated Jul. 26, 2018 in related Application No. 11818591.7 filed Aug. 12, 2011 (8 pages).

* cited by examiner

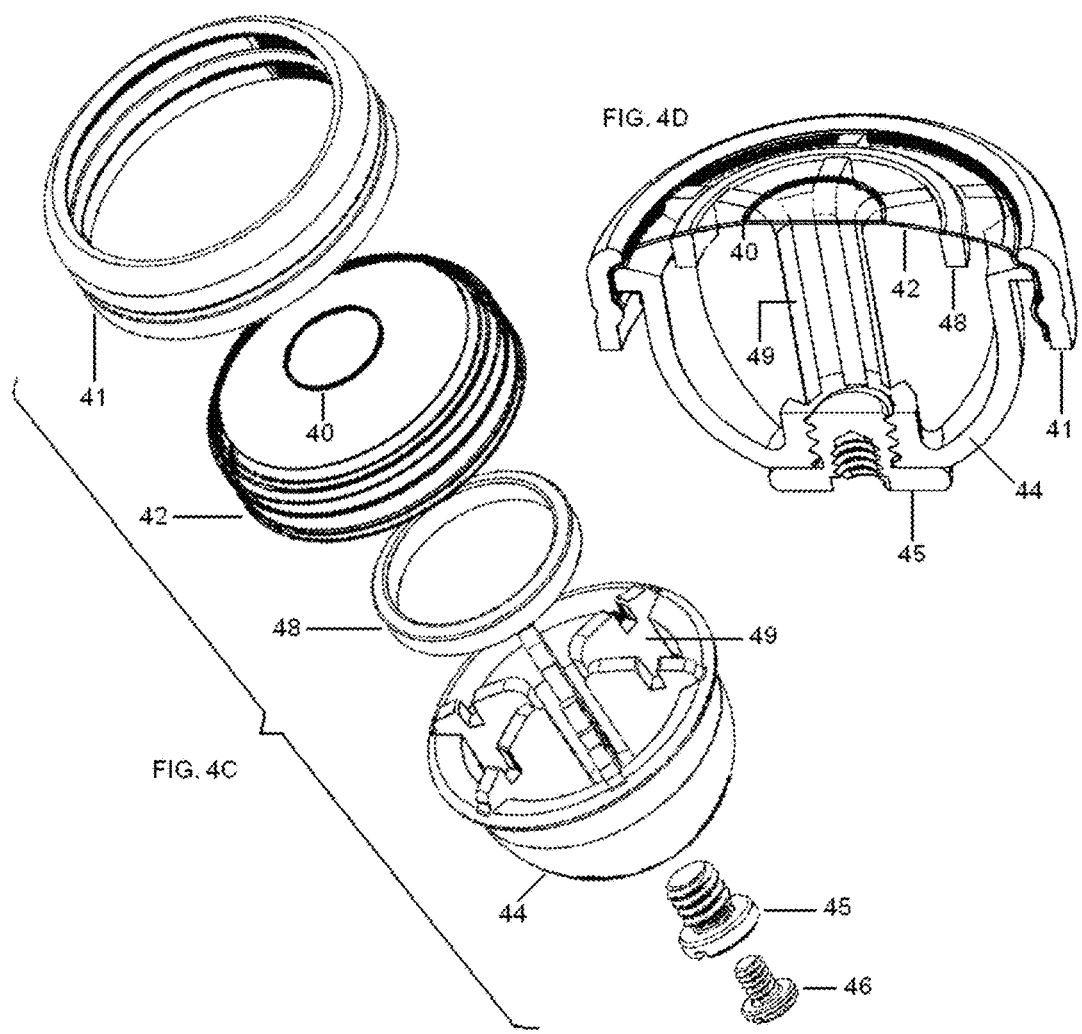

ELECTRICAL AND MAGNETIC STIMULATORS USED TO TREAT MIGRAINE/SINUS HEADACHE, RHINITIS, SINUSITIS, RHINOSINUSITIS, AND COMORBID DISORDERS

CROSS REFERENCE TO RELATED APPLICATIONS

The present application is a Continuation of U.S. application Ser. No. 13/183,721 filed 15 Jul. 2011 now U.S. Pat. No. 8,676,324 issued 18 Mar. 2014, which is (1) a Continuation in Part of U.S. application Ser. No. 13/109,250 filed 17 May 2011 and claims the benefit of U.S. Provisional Application No. 61/471,405 filed 4 Apr. 2011, and (2) a Continuation in Part of U.S. application Ser. No. 13/075,746 filed 30 Mar. 2011 and claims the benefit of U.S. Provisional Application No. 61/451,259 filed 10 Mar. 2011; each of which is incorporated herein by reference in its entirety.

BACKGROUND OF THE INVENTION

The field of the present invention relates to the delivery of energy impulses (and/or fields) to bodily tissues for therapeutic purposes. It relates more specifically to the use of non-invasive devices, especially non-invasive electrical nerve stimulation devices and magnetic stimulation devices, along with methods of treating medical disorders using energy that is delivered by such devices. The disorders comprise migraine and other primary headaches such as cluster headaches, including sinus symptoms that resemble an immune-mediated response ("sinus" headaches), irrespective of whether those symptoms arise from an allergy that is co-morbid with the headache. The methods may also be used to treat other disorders that may be co-morbid with migraine headaches, such as anxiety disorders in which the nervous system may also be hyper-reactive and in which attacks may be triggered by some of the same factors that trigger migraine and asthma attacks. In preferred embodiments of the disclosed methods, one or both of the patient's vagus nerves are stimulated non-invasively. In other embodiments, parts of the sympathetic nervous system and/or the adrenal glands are stimulated.

Treatments for various infirmities sometime require the destruction of otherwise healthy tissue in order to produce a beneficial effect. Malfunctioning tissue is identified and then lesioned or otherwise compromised in order to produce a beneficial outcome, rather than attempting to repair the tissue to its normal functionality. A variety of techniques and mechanisms have been designed to produce focused lesions directly in target nerve tissue, but collateral damage is inevitable.

Other treatments for malfunctioning tissue can be medicinal in nature, but in many cases the patients become dependent upon artificially synthesized chemicals. In many cases, these medicinal approaches have side effects that are either unknown or quite significant. Unfortunately, the beneficial outcomes of surgery and medicines are often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue holds significant promise for the treatment of many ailments, because such stimulation is generally a wholly reversible and non-destructive treatment.

Nerve stimulation is thought to be accomplished directly or indirectly by depolarizing a nerve membrane, causing the discharge of an action potential; or by hyperpolarization of a nerve membrane, preventing the discharge of an action potential. Such stimulation may occur after electrical energy, or also other forms of energy, are transmitted to the vicinity of a nerve [F. RATTAY. The basic mechanism for the electrical stimulation of the nervous system. Neuroscience 89 (2, 1999):335-346; Thomas HEIMBURG and Andrew D. Jackson. On solution propagation in biomembranes and nerves. PNAS 102 (28, 2005): 9790-9795]. Nerve stimulation may be measured directly as an increase, decrease, or modulation of the activity of nerve fibers, or it may be inferred from the physiological effects that follow the transmission of energy to the nerve fibers.

One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference).

Another application of electrical stimulation of nerves has been the treatment of radiating pain in the lower extremities by stimulating the sacral nerve roots at the bottom of the spinal cord (see U.S. Pat. No. 6,871,099 to WHITEHURST, et al., the disclosure of which is incorporated herein by reference).

Electrical stimulation of the brain with implanted electrodes has also been approved for use in the treatment of various conditions, including movement disorders such as essential tremor and Parkinson's disease. The principle underlying these approaches involves disruption and modulation of hyperactive neuronal circuit transmission at specific sites in the brain. Unlike potentially dangerous lesioning procedures in which aberrant portions of the brain are physically destroyed, electrical stimulation is achieved by implanting electrodes at these sites. The electrodes are used first to sense aberrant electrical signals and then to send electrical pulses to locally disrupt pathological neuronal transmission, driving it back into the normal range of activity. These electrical stimulation procedures, while invasive, are generally conducted with the patient conscious and a participant in the surgery.

However, brain stimulation, and deep brain stimulation in particular, is not without some drawbacks. The procedure requires penetrating the skull, and inserting an electrode into brain matter using a catheter-shaped lead, or the like. While monitoring the patient's condition (such as tremor activity, etc.), the position of the electrode is adjusted to achieve significant therapeutic potential. Next, adjustments are made to the electrical stimulus signals, such as frequency, periodicity, voltage, current, etc., again to achieve therapeutic results. The electrode is then permanently implanted, and wires are directed from the electrode to the site of a surgically implanted pacemaker. The pacemaker provides the electrical stimulus signals to the electrode to maintain the therapeutic effect. While the therapeutic results of deep brain stimulation are promising, significant complications may arise from the implantation procedure, including stroke induced by damage to surrounding tissues and the neurovasculature.

Most of the above-mentioned applications of electrical stimulation involve the surgical implantation of electrodes within a patient. In contrast, for embodiments of the present invention, the disclosed devices and medical procedures stimulate nerves by transmitting energy to nerves and tissue non-invasively. They may offer the patient an alternative that does not involve surgery. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that invasive procedures do involve inserting a substance or device into or through the skin or into an internal body cavity beyond a body orifice. For example, transcutaneous electrical nerve stimulation (TENS) is non-invasive because it involves attaching electrodes to the surface of the skin (or using a form-fitting conductive garment) without breaking the skin. In contrast, percutaneous electrical stimulation of a nerve is minimally invasive because it involves the introduction of an electrode under the skin, via needle-puncture of the skin (see commonly assigned co-pending US Patent Application 2010/0241188, entitled Percutaneous Electrical Treatment of Tissue to ERRICO et al, which is hereby incorporated by reference).

Potential advantages of non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures generally present fewer problems with biocompatibility. In cases involving the attachment of electrodes, non-invasive methods have less of a tendency for breakage of leads, and the electrodes can be easily repositioned if necessary. Non-invasive methods are sometimes painless or only minimally painful and may be performed without the need for even local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace, and the cost of non-invasive procedures may be reduced relative to comparable invasive procedures.

Electrodes that are applied non-invasively to the surface of the body have a long history, including electrodes that were used to stimulate underlying nerves [L. A. GEDDES. Historical Evolution of Circuit Models for the Electrode-Electrolyte Interface. Annals of Biomedical Engineering 25 (1997):1-14]. However, electrical stimulation of nerves in general fell into disfavor in middle of the twentieth century, until the "gate theory of pain" was introduced by Melzack and Wall in 1965. This theory, along with advances in electronics, reawakened interest in the use of implanted electrodes to stimulate nerves, initially to control pain.

Screening procedures were then developed to determine suitable candidates for electrode implantation, which involved first determining whether the patient responded when stimulated with electrodes applied to the surface of the body in the vicinity of the possible implant. It was subsequently found that the surface stimulation often controlled pain so well that there was no need to implant a stimulating electrode [Charles Burton and Donald D. Maurer. Pain Suppression by Transcutaneous Electronic Stimulation. IEEE Transactions on Biomedical Engineering BME-21(2, 1974): 81-88]. Such non-invasive transcutaneous electrical nerve stimulation (TENS) was then developed for treating different types of pain, including pain in a joint or lower back, cancer pain, post-operative pain, post-traumatic pain, and pain associated with labor and delivery [Steven E. ABRAM. Transcutaneous Electrical Nerve Stimulation. pp 1-10 in: Joel B. Myklebust, ed. Neural stimulation (Volume 2). Boca Raton, Fla. CRC Press 1985; WALSH D M, Lowe A S, McCormack K. Willer J-C, Baxter G D, Allen J M. Transcutaneous electrical nerve stimulation: effect on peripheral nerve conduction, mechanical pain threshold, and tactile threshold in humans. Arch Phys Med Rehabil 79(1998):1051-1058; J A CAMPBELL. A critical appraisal of the electrical output characteristics of ten transcutaneous nerve stimulators. Clin. phys. Physiol. Meas. 3(2, 1982): 141-150; U.S. Pat. No. 3,817,254, entitled Transcutaneous stimulator and stimulation method, to Maurer; U.S. Pat. No. 4,324,253, entitled Transcutaneous pain control and/or muscle stimulating apparatus, to Greene et al; U.S. Pat. No. 4,503,863, entitled Method and apparatus for transcutaneous electrical stimulation, to Katims; U.S. Pat. No. 5,052,391, entitled High frequency high intensity transcutaneous electrical nerve stimulator and method of treatment, to Silberstone et al; U.S. Pat. No. 6,351,674, entitled Method for inducing electroanesthesia using high frequency, high intensity transcutaneous electrical nerve stimulation, to Silverstone].

As TENS was being developed to treat pain, non-invasive electrical stimulation using surface electrodes was simultaneously developed for additional therapeutic or diagnostic purposes, which are known collectively as electrotherapy. Neuromuscular electrical stimulation (NMES) stimulates normally innervated muscle in an effort to augment strength and endurance of normal (e.g., athletic) or damaged (e.g., spastic) muscle. Functional electrical stimulation (FES) is used to activate nerves innervating muscle affected by paralysis resulting from spinal cord injury, head injury, stroke and other neurological disorders, or muscle affected by foot drop and gait disorders. FES is also used to stimulate muscle as an orthotic substitute, e.g., replace a brace or support in scoliosis management. Another application of surface electrical stimulation is chest-to-back stimulation of tissue, such as emergency defibrillation and cardiac pacing. Surface electrical stimulation has also been used to repair tissue, by increasing circulation through vasodilation, by controlling edema, by healing wounds, and by inducing bone growth. Surface electrical stimulation is also used for iontophoresis, in which electrical currents drive electrically charged drugs or other ions into the skin, usually to treat inflammation and pain, arthritis, wounds or scars. Stimulation with surface electrodes is also used to evoke a response for diagnostic purposes, for example in peripheral nerve stimulation (PNS) that evaluates the ability of motor and sensory nerves to conduct and produce reflexes. Surface electrical stimulation is also used in electroconvulsive therapy to treat psychiatric disorders; electroanesthesia, for example, to prevent pain from dental procedures; and electrotactile speech processing to convert sound into tactile sensation for the hearing impaired. All of the above-mentioned applications of surface electrode stimulation are intended not to damage the patient, but if higher currents are used with special electrodes, electrosurgery may be performed as a means to cut, coagulate, desiccate, or fulgurate tissue [Mark R. Prausnitz. The effects of electric current applied to skin: A review for transdermal drug delivery. Advanced Drug Delivery Reviews 18 (1996) 395-425].

Despite its attractiveness, non-invasive electrical stimulation of a nerve is not always possible or practical. This is primarily because the current state of the art may not be able to stimulate a deep nerve selectively or without producing excessive pain, since the stimulation may unintentionally stimulate nerves other than the nerve of interest, including nerves that cause pain. For this reason, forms of electrical stimulation other than TENS may be best suited for the treatment of particular types of pain [Paul F. WHITE, shitong Li and Jen W. Chiu. Electroanalgesia: Its Role in Acute and Chronic Pain Management. Anesth Analg 92(2001):505-13].

For some other electrotherapeutic applications, it has also been difficult to perform non-invasive stimulation of a nerve, in lieu of stimulating that nerve invasively. The therapies most relevant to the present invention involve electrical stimulation of the vagus nerve in the neck, which was developed initially for the treatment of epilepsy. The left vagus nerve is ordinarily stimulated at a location within the neck by first surgically implanting an electrode there, then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al and U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060; GROVES D A, Brown V J. Vagal nerve stimulation: a review of its applications and potential mechanisms that mediate its clinical effects. Neurosci Biobehav Rev (2005) 29:493-500; Reese TERRY, Jr. Vagus nerve stimulation: a proven therapy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4].

When it is desired to avoid the surgical implantation of an electrode, vagal nerve stimulation (VNS) may be performed less invasively by positioning one or more electrodes in the esophagus, trachea, or jugular vein, but with one electrode positioned on the surface of the body [U.S. Pat. No. 7,340,299, entitled Methods of indirectly stimulating the vagus nerve to achieve controlled asystole, to PUSKAS; and U.S. Pat. No. 7,869,884, entitled Non-surgical device and methods for trans-esophageal vagus nerve stimulation, to SCOTT et al]. Despite their advantage as being non-surgical, such methods nevertheless exhibit other disadvantages associated with invasive procedures.

In other patents, non-invasive VNS is disclosed, but at a location other than in the neck [e.g., U.S. Pat. No. 4,865,048, entitled Method and apparatus for drug free neurostimulation, to ECKERSON; U.S. Pat. No. 6,609,025 entitled Treatment of obesity by bilateral sub-diaphragmatic nerve stimulation to BARRETT et al; U.S. Pat. No. 5,458,625, entitled Transcutaneous nerve stimulation device and method for using same, to KENDALL; U.S. Pat. No. 7,386,347, entitled Electric stimulator for alpha-wave derivation, to Chung et al.; U.S. Pat. No. 7,797,042, entitled Device for applying a transcutaneous stimulus or for transcutaneous measuring of a parameter, to Dietrich et al.; patent application US2010/0057154, entitled Device and Method for the Transdermal Stimulation of a Nerve of the Human Body, to Dietrich et al; US2006/0122675, entitled Stimulator for auricular branch of vagus nerve, to Libbus et al; US2008/0288016, entitled Systems and Methods for Stimulating Neural Targets, to Amurthur et al]. However, because such non-invasive VNS occurs at a location other than the neck, it is not directly comparable to invasive VNS in the neck, for which therapeutic results are well documented. Among other patents and patent applications, non-invasive VNS is sometimes mentioned along with invasive VNS methods, but without addressing the problem of unintentional stimulation of nerves other than the vagus nerve, particularly nerves that cause pain [e.g., US20080208266, entitled System and Method for Treating Nausea and Vomiting by Vagus Nerve Stimulation, to LESSER et al]. Other patents are vague as to how non-invasive electrical stimulation in the vicinity of the vagus nerve in the neck is to be accomplished [e.g., U.S. Pat. No. 7,499,747, entitled External baroreflex activation, to KIEVAL et al].

The present invention uses electrical nerve stimulation to treat headaches, particularly non-invasive vagal nerve stimulation in the neck. According to the International Classification of Headache Disorders (ICHD-II), there are four types of primary headaches: migraine, tension-type, cluster headache plus other trigeminal autonomic cephalalgias, and other primary headaches (e.g., cough headache, exertional headache). Additional headache types are recognized, but they are attributable to some causative factor such as head and/or neck trauma, vascular disorder, other intracranial disorders such as hypertension, substance abuse, infection, homeostasis disorder, facial structural problems (e.g., tooth or ear), psychiatric problems, or cranial neuralgia [Jes OLESEN et al. The International Classification of Headache Disorders, Second Edition (ICHD-II). Cephalalgia 24 (Suppl. 1, 2004): 1-160]. An overview of the diagnosis and treatment of primary and some secondary headaches is found in a publication by the British Association for the Study of Headaches (BASH) [T J STEINER, E A MacGregor, P T G Davies. Guidelines for All Healthcare Professionals in the Diagnosis and Management of Migraine, Tension-Type, Cluster and Medication-Overuse Headache, 3rd Edition, 2007. BASH. Department of Neurology, Hull Royal Infirmary, Anlaby Road, Hull HU3 2JZ Great Britain].

SUMMARY OF THE INVENTION

In one aspect of the invention, devices and methods are described to produce therapeutic effects in a patient by utilizing an energy source that transmits energy non-invasively to nervous tissue. In particular, the disclosed devices can transmit energy to, or in close proximity to, a vagus nerve in the neck of the patient, in order to temporarily stimulate, block and/or modulate electrophysiological signals in that nerve. The methods that are disclosed herein comprise stimulating the vagus nerve with particular stimulation waveform parameters, preferably using the nerve stimulator devices that are also described herein.

A novel stimulator device is used to modulate electrical activity of a vagus nerve or other nerves or tissue. The stimulator comprises a source of electrical power and two or more remote electrodes that are configured to stimulate a deep nerve relative to the nerve axis. The device also comprises continuous electrically conducting media within which the electrodes are in contact, wherein a conducting medium has a shape that conforms to the contour of a target body surface of a patient when the medium is applied to the target body surface. In another aspect of the invention, a non-invasive magnetic stimulator device is used to modulate electrical activity of the vagus nerve or other nerves or tissue.

For the present medical applications, a device is ordinarily applied to the patient's neck. In a preferred embodiment of the invention, the stimulator comprises two electrodes that lie side-by-side within separate stimulator heads, wherein the electrodes are separated by electrically insulating material. Each electrode and the patient's skin are in continuous contact with an electrically conducting medium that extends from the skin to the electrode. The conducting media for different electrodes are also separated by electrically insulating material. In another embodiment of the invention, a non-invasive magnetic stimulator device is ordinarily applied to the patient's neck.

A source of power supplies a pulse of electric charge to the electrodes or magnetic stimulator, such that the electrodes or magnetic stimulator produce an electric current and/or an electric field within the patient. The electrical or magnetic stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m and an electrical field gradient of greater than 2 V/m/mm.

Current passing through an electrode may be about 0 to 40 mA, with voltage across the electrodes of 0 to 30 volts. The current is passed through the electrodes in bursts of pulses. There may be 1 to 20 pulses per burst, preferably five pulses. Each pulse within a burst has a duration of 20 to 1000 microseconds, preferably 200 microseconds. A burst followed by a silent inter-burst interval repeats at 1 to 5000 bursts per second (bps), preferably at 15-50 bps. The preferred shape of each pulse is a full sinusoidal wave. The preferred stimulator shapes an elongated electric field of effect that can be oriented parallel to a long nerve, such as a vagus nerve in the patient's neck. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves that produce pain.

The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, shaping an elongated electrical field of effect as with the electrode-based stimulator.

Teachings of the present invention demonstrate how the disclosed non-invasive stimulators may be positioned and used against body surfaces, particularly at a location on the patient's neck under which a vagus nerve is situated. Those teachings also describe the production of certain beneficial, therapeutic effects in a patient. An exemplary teaching is the treatment of migraine and other primary headaches such as cluster headaches, including sinus symptoms that resemble an immune-mediated response ("sinus" headaches), irrespective of whether those symptoms arise from an allergy that is co-morbid with the headache. Thus, the devices and methods may be used to treat allergic or non-allergic rhinitis, acute or chronic sinusitis, or acute or chronic rhinosinusitis, independently of whether the patient has a headache.

The treatment causes patients to experience a very rapid (within a matter of a few seconds) relief from headache pain, as well as a rapid opening of the nasal passages within approximately 20 minutes. Effects of the disclosed treatment method last for 4 to 5 hours, and the method has none of the side effects typically associated with pseudoephedrine products or other allergy medications. The disclosure also describes treatment of other disorders that may be co-morbid with migraine headaches, such as anxiety disorders, in which attacks may be triggered by some of the same factors that trigger migraine and asthma attacks. In preferred embodiments of the disclosed methods, a vagus nerve is stimulated non-invasively, but in other embodiments, parts of the sympathetic nervous system and/or the adrenal glands are stimulated. However, it should be understood that application of the methods and devices is not limited to the examples that are given.

The novel systems, devices and methods for treating conditions using the disclosed stimulator or other non-invasive stimulation devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

This application refers to the following patents and patent applications, the entire disclosures of which are hereby incorporated by reference for all purposes: U.S. Provisional Patent Application No. 61/487,439 filed May 18, 2011. This application is a continuation-in-part of U.S. patent application Ser. No. 13/109,250 filed May 17, 2011 which claims the benefit of priority of U.S. Provisional Patent Application No. 61/471,405 filed Apr. 4, 2011 and this application is a continuation-in-part of U.S. patent application Ser. No. 13/075,746 filed Mar. 30, 2011 which claims the benefit of priority of U.S. Provisional Patent Application No. 61/451,259 filed Mar. 10, 2011. This application is a continuation-in-part of U.S. patent application Ser. No. 13/024,727 filed Feb. 10, 2011 which is a continuation-in-part application of U.S. patent application Ser. No. 13/005,005 filed Jan. 12, 2011, which is a continuation-in-part application of U.S. patent application Ser. No. 12/964,050 filed Dec. 19, 2010, which claims the benefit of priority of U.S. Provisional Patent Application No. 61/415,469 filed Nov. 19, 2010 and is a continuation-in-part application of U.S. patent application Ser. No. 12/859,568 filed Aug. 9, 2010, which is a continuation-in-part of U.S. patent application Ser. No. 12/408,131 filed Mar. 20, 2009 and a continuation-in-part application of U.S. patent application Ser. No. 12/612,177 filed Nov. 9, 2009.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIGS. 4A-4D illustrate preferred and alternate embodiments of the head of the dual-electrode stimulator that is shown in FIG. 3.

DETAILED DESCRIPTION OF THE PREFERRED EMBODIMENTS

Figure 1A:
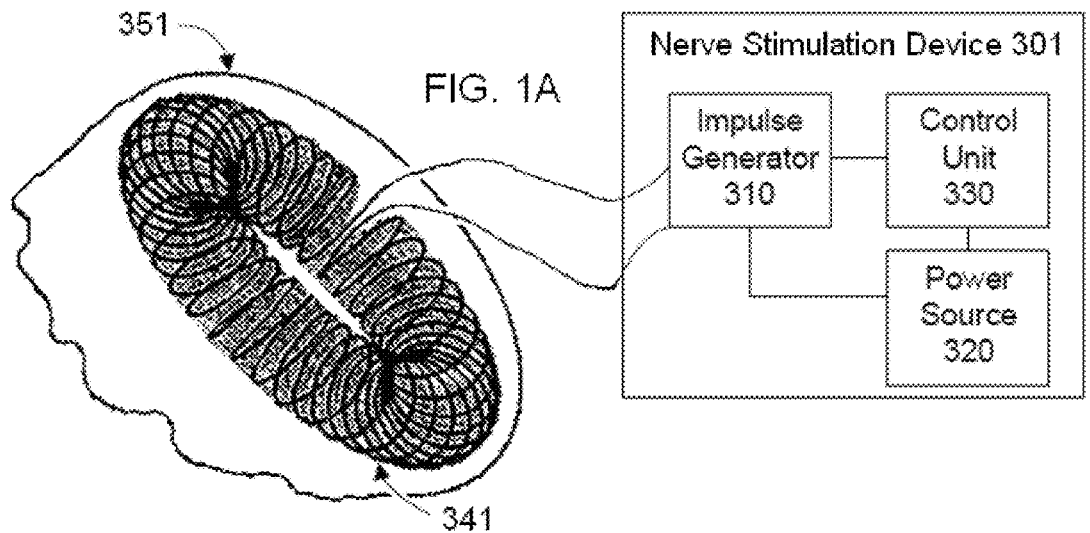
FIGS. 1A-1B are a schematic view of magnetic and electrode-based nerve or tissue modulating devices according to the present invention, which supply controlled pulses of electrical current to magnetic coils or to electrodes, respectively, and each of which are continuously in contact with a volume that is filled with electrically conducting material.

In the present invention, energy is transmitted non-invasively to a patient. The invention is particularly useful for producing applied electrical impulses that interact with the signals of one or more nerves to achieve a therapeutic result.

In particular, the present disclosure describes devices and methods to stimulate a vagus nerve non-invasively at a location on the patient's neck.

There is a long-felt but unsolved need to stimulate the vagus nerve electrically in the neck, totally non-invasively, selectively, and essentially without producing pain. As described below, this is evidenced by the failure of others to solve the problem that is solved by the present invention, such that investigators abandoned the attempt to non-invasively stimulate electrically in the neck, in favor of stimulating the vagus nerve at other anatomical locations, or in favor of stimulating the vagus nerve non-electrically. Japanese patent application JP2009233024A with a filing date of Mar. 26, 2008, entitled Vagus Nerve Stimulation System, to Fukui YOSHIHITO, is concerned with stimulation of the vagus nerve on the surface of the neck to control heart rate, rather than epilepsy, depression, or other infirmities that vagal nerve stimulation (VNS) is ordinarily intended to treat. Nevertheless, the approach that is taken by Yoshihito illustrates the difficulties encountered with non-invasive electrical stimulation the vagus nerve. Yoshihito notes that because electrical stimulation on the surface of the neck may co-stimulate the phrenic nerve that is involved with the control of respiration, the patient hiccups and does not breathe normally, resulting in "a patient sense of incongruity and displeasure." Yoshihito's proposed solution to the problem is to modulate the timing and intensity of the electrical stimulation at the neck as a function of the respiratory phase, in such a way that the undesirable respiratory effects are minimized. Thus, Yoshihito's approach is to compensate for non-selective nerve stimulation, rather than find a way to stimulate the vagus nerve selectively. However, such compensatory modulation might also prevent the stimulation from achieving a beneficial effect in treating epilepsy, depression, and other infirmities that are treated with VNS. Furthermore, Yoshihito does not address the problem of pain in the vicinity of the stimulation electrodes. Similar issues could conceivably arise in connection with possible co-stimulation of the carotid sinus nerve [Ingrid J. M. Scheffers, Abraham A. Kroon, Peter W. de Leeuw. Carotid Baroreflex Activation: Past, Present, and Future. Curr Hypertens Rep 12(2010):61-66]. Side effects due to co-activation of muscle that is controlled by the vagus nerve itself may also occur, which exemplify another type of non-selective stimulation [M Tosato, K Yoshida, E Toft and J J Struijk. Quasi-trapezoidal pulses to selectively block the activation of intrinsic laryngeal muscles during vagal nerve stimulation. J. Neural Eng. 4 (2007): 205-212].

One circumvention of the problem that the present invention solves is to non-invasively stimulate the vagus nerve at an anatomical location other than the neck, where the nerve lies closer to the skin. A preferred alternate location is in or around the ear (tragus, meatus and/or concha) although other locations have been proposed [Manuel L. KARELL. TENS in the Treatment of Heroin Dependency. The Western Journal of Medicine 125 (5, 1976):397-398; Enrique C. G. VENTUREYRA. Transcutaneous vagus nerve stimulation for partial onset seizure therapy. A new concept. Child's Nery Syst 16 (2000):101-102; T. KRAUS, K. Hosl, O. Kiess, A. Schanze, J. Kornhuber, C. Forster. BOLD fMRI deactivation of limbic and temporal brain structures and mood enhancing effect by transcutaneous vagus nerve stimulation. J Neural Transm 114 (2007): 1485-1493; POLAK T, Markulin F, Ehlis A C, Langer J B, Ringel T M, Fallgatter A J. Far field potentials from brain stem after transcutaneous vagus nerve stimulation: optimization of stimulation and recording parameters. J Neural Transm 116(10, 2009):1237-1242; U.S. Pat. No. 5,458,625, entitled Transcutaneous nerve stimulation device and method for using same, to KENDALL; U.S. Pat. No. 7,797,042, entitled Device for applying a transcutaneous stimulus or for transcutaneous measuring of a parameter, to Dietrich et al.; patent application US2010/0057154, entitled Device and Method for the Transdermal Stimulation of a Nerve of the Human Body, to Dietrich et al; See also the non-invasive methods and devices that Applicant disclosed in commonly assigned co-pending U.S. patent application Ser. No. 12/859,568 entitled Non-invasive Treatment of Bronchial Constriction, to SIMON]. However, it is not certain that stimulation in this minor branch of the vagus nerve will have the same effect as stimulation of a main vagus nerve in the neck, where VNS electrodes are ordinarily implanted, and for which VNS therapeutic procedures produce well-documented results.

Another circumvention of the problem is to substitute electrical stimulation of the vagus nerve in the neck with some other form of stimulation. For example, mechanical stimulation of the vagus nerve on the neck has been proposed as an alternative to electrical stimulation [Jared M. HUSTON, Margot Gallowitsch-Puerta, Mahendar Ochani, Kanta Ochani, Renqi Yuan, Mauricio Rosas-Ballina, Mala Ashok, Richard S. Goldstein, Sangeeta Chavan, Valentin A. Pavlov, Christine N. Metz, Huan Yang, Christopher J. Czura, Haichao Wang, Kevin J. Tracey. Transcutaneous vagus nerve stimulation reduces serum high mobility group box 1 levels and improves survival in murine sepsis Crit Care Med 35 (12, 2007):2762-2768; Artur BAUHOFER and Alexander Torossian. Mechanical vagus nerve stimulation—A new adjunct in sepsis prophylaxis and treatment? Crit Care Med 35 (12, 2007):2868-2869; Hendrik SCHMIDT, Ursula Muller-Werdan, Karl Werdan. Assessment of vagal activity during transcutaneous vagus nerve stimulation in mice. Crit Care Med 36 (6, 2008):1990; see also the non-invasive methods and devices that Applicant disclosed in commonly assigned co-pending U.S. patent application Ser. No. 12/859,568 entitled Non-invasive Treatment of Bronchial Constriction, to SIMON]. However, such mechanical VNS has only been performed in animal models, and there is no evidence that such mechanical VNS would be functionally equivalent to electrical VNS.

Another circumvention of the problem is to use magnetic rather than purely electrical stimulation of the vagus nerve in the neck [Q. AZIZ et al. Magnetic Stimulation of Efferent Neural Pathways to the Human Oesophagus. Gut 33: S53-S70 (Poster Session F218) (1992); AZIZ, Q., J. C. Rothwell, J. Barlow, A. Hobson, S. Alani, J. Bancewicz, and D. G. Thompson. Esophageal myoelectric responses to magnetic stimulation of the human cortex and the extracranial vagus nerve. Am. J. Physiol. 267 (Gastrointest. Liver Physiol. 30): G827-G835, 1994; Shaheen HAMDY, Qasim Aziz, John C. Rothwell, Anthony Hobson, Josephine Barlow, and David G. Thompson. Cranial nerve modulation of human cortical swallowing motor pathways. Am. J. Physiol. 272 (Gastrointest. Liver Physiol. 35): G802-G808, 1997; Shaheen HAMDY, John C. Rothwell, Qasim Aziz, Krishna D. Singh, and David G. Thompson. Long-term reorganization of human motor cortex driven by short-term sensory stimulation. Nature Neuroscience 1 (issue 1, May 1998):64-68; A. SHAFIK. Functional magnetic stimulation of the vagus nerve enhances colonic transit time in healthy volunteers. Tech Coloproctol (1999) 3:123-12; see also the non-invasive methods and devices that Applicant disclosed in co-pending U.S. patent application Ser. No. 12/859,568 entitled Non-invasive Treatment of Bronchial Constriction, to SIMON, as well as co-pending U.S. patent application Ser. No. 12/964,050 entitled Magnetic Stimulation Devices and Methods of Therapy, to SIMON et al]. Magnetic stimulation might functionally approximate electrical stimulation. However, magnetic stimulation has the disadvantage that it ordinarily requires complex and expensive equipment, and the duration of stimulation may be limited by overheating of the magnetic stimulator. Furthermore, in some cases, magnetic stimulation in the neck might also inadvertently stimulate nerves other than the vagus nerve, such as the phrenic nerve [SIMILOWSKI, T., B. Fleury, S. Launois, H. P. Cathala, P. Bouche, and J. P. Derenne. Cervical magnetic stimulation: a new painless method for bilateral phrenic nerve stimulation in conscious humans. J. Appl. Physiol. 67(4): 1311-1318, 1989; Gerrard F. RAFFERTY, Anne Greenough, Terezia Manczur, Michael I. Polkey, M. Lou Harris, Nigel D. Heaton, Mohamed Rela, and John Moxham. Magnetic phrenic nerve stimulation to assess diaphragm function in children following liver transplantation. Pediatr Crit Care Med 2001, 2:122-126; W. D-C. MAN, J. Moxham, and M. I. Polkey. Magnetic stimulation for the measurement of respiratory and skeletal muscle function. Eur Respir J 2004; 24: 846-860]. Furthermore, magnetic stimulation may also stimulate nerves that cause pain. Other stimulators that make use of magnetic fields might also be used, but they too are complex and expensive and may share other disadvantages with more conventional magnetic stimulators [U.S. Pat. No. 7,699,768, entitled Device and method for non-invasive, localized neural stimulation utilizing hall effect phenomenon, to Kishawi et al].

Transcutaneous electrical stimulation (as well as magnetic stimulation) can be unpleasant or painful, in the experience of patients that undergo such procedures. The quality of sensation caused by stimulation depends strongly on current and frequency, such that currents barely greater than the perception threshold generally cause painless sensations described as tingle, itch, vibration, buzz, touch, pressure, or pinch, but higher currents can cause sharp or burning pain. As the depth of penetration of the stimulus under the skin is increased (e.g., to deeper nerves such as the vagus nerve), any pain will generally begin or increase. Strategies to reduce the pain include: use of anesthetics placed on or injected into the skin near the stimulation and placement of foam pads on the skin at the site of stimulation [Jeffrey J. BORCKARDT, Arthur R. Smith, Kelby Hutcheson, Kevin Johnson, Ziad Nahas, Berry Anderson, M. Bret Schneider, Scott T. Reeves, and Mark S. George. Reducing Pain and Unpleasantness During Repetitive Transcranial Magnetic Stimulation. Journal of ECT 2006; 22:259-264], use of nerve blockades [V. HAKKINEN, H. Eskola, A. Yli-Hankala, T. Nurmikko and S. Kolehmainen. Which structures are sensitive to painful transcranial stimulation? Electromyogr. clin. Neurophysiol. 1995, 35:377-383], the use of very short stimulation pulses [V. SUIHKO. Modeling the response of scalp sensory receptors to transcranial electrical stimulation. Med. Biol. Eng. Comput., 2002, 40, 395-401], decreasing current density by increasing electrode size [Kristof VERHOEVEN and J. Gert van Dijk. Decreasing pain in electrical nerve stimulation. Clinical Neurophysiology 117 (2006) 972-978], using a high impedance electrode [N. SHA, L. P. J. Kenney, B. W. Heller, A. T. Barker, D. Howard and W. Wang. The effect of the impedance of a thin hydrogel electrode on sensation during functional electrical stimulation. Medical Engineering & Physics 30 (2008): 739-746] and providing patients with the amount of information that suits their personalities [Anthony DELITTO, Michael J Strube, Arthur D Shulman, Scott D Minor. A Study of Discomfort with Electrical Stimulation. Phys. Ther.

1992; 72:410-424]. U.S. Pat. No. 7,614,996, entitled Reducing discomfort caused by electrical stimulation, to RIEHL discloses the application of a secondary stimulus to counteract what would otherwise be an uncomfortable primary stimulus. Other methods have been described for invasive, rather than non-invasive stimulation [U.S. Pat. No. 7,904,176, entitled Techniques for reducing pain associated with nerve stimulation, to Ben-Ezra et al.].

Additional considerations related to pain resulting from the stimulation are as follows. When stimulation is repeated over the course of multiple sessions, patients may adapt to the pain and exhibit progressively less discomfort. Patients may be heterogeneous with respect to their threshold for pain caused by stimulation, including heterogeneity related to gender and age. Electrical properties of an individual's skin vary from day to day and may be affected by cleaning, abrasion, and the application of various electrode gels and pastes. Skin properties may also be affected by the stimulation itself, as a function of the duration of stimulation, the recovery time between stimulation sessions, the transdermal voltage, the current density, and the power density. The application of multiple electrical pulses can result in different perception or pain thresholds and levels of sensation, depending on the spacing and rate at which pulses are applied. The separation distance between two electrodes determines whether sensations from the electrodes are separate, overlap, or merge. The limit for tolerable sensation is sometimes said to correspond to a current density of 0.5 $mA/cm^2$, but in reality the functional relationship between pain and current density is very complicated. Maximum local current density may be more important in producing pain than average current density, and local current density generally varies under an electrode, e.g., with greater current densities along edges of the electrode or at "hot spots." Furthermore, pain thresholds can have a thermal and/or electrochemical component, as well as a current density component. Pulse frequency plays a significant role in the perception of pain, with muscle contraction being involved at some frequencies and not others, and with the spatial extent of the pain sensation also being a function of frequency. The sensation is also a function of the waveform (square-wave, sinusoidal, trapezoidal, etc.), especially if pulses are less than a millisecond in duration [Mark R. PRAUSNITZ. The effects of electric current applied to skin: A review for transdermal drug delivery. Advanced Drug Delivery Reviews 18 (1996): 395-425].

Considering that there are so many variables that may influence the likelihood of pain during non-invasive electrical stimulation (detailed stimulus waveform, frequency, current density, electrode type and geometry, skin preparation, etc.), considering that these same variables must be simultaneously selected in order to independently produce a desired therapeutic outcome by vagal nerve stimulation, and considering that one also wishes to selectively stimulate the vagus nerve (e.g., avoid stimulating the phrenic nerve), it is understandable that prior to the present disclosure, no one has described devices and methods for stimulating the vagus nerve electrically in the neck, totally non-invasively, selectively, and without causing substantial pain.

Applicant discovered the disclosed devices and methods in the course of experimentation with a magnetic stimulation device that was disclosed in Applicant's commonly assigned co-pending U.S. patent application Ser. No. 12/964,050 entitled Magnetic Stimulation Devices and Methods of Therapy, to SIMON et al. Thus, combined elements in the invention do not merely perform the function that the elements perform separately (viz., perform therapeutic VNS, minimize stimulation pain, or stimulate the vagus nerve selectively), and one of ordinary skill in the art would not have combined the claimed elements by known methods because the archetypal magnetic stimulator was known only to Applicant. That stimulator used a magnetic coil, embedded in a safe and practical conducting medium that was in direct contact with arbitrarily-oriented patient's skin, which had not been described in its closest art [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May 1999. (UMI Microform Number: 9940153, UMI Company, Ann Arbor, Mich.)].

Referring now to FIG. 1, FIG. 1A is a schematic diagram of Applicant's above-mentioned magnetic nerve stimulating/modulating device 301 for delivering impulses of energy to nerves for the treatment of medical conditions. As shown, device 301 may include an impulse generator 310; a power source 320 coupled to the impulse generator 310; a control unit 330 in communication with the impulse generator 310 and coupled to the power source 320; and a magnetic stimulator coil 341 coupled via wires to impulse generator coil 310. The stimulator coil 341 is toroidal in shape, due to its winding around a toroid of core material.

Although the magnetic stimulator coil 341 is shown in FIG. 1A to be a single coil, in practice the coil may also comprise two or more distinct coils, each of which is connected in series or in parallel to the impulse generator 310. Thus, the coil 341 shown in FIG. 1A represents all the magnetic stimulator coils of the device collectively. In a preferred embodiment, coil 341 actually contains two coils that may be connected either in series or in parallel to the impulse generator 310.

The item labeled in FIG. 1A as 351 is a volume, surrounding the coil 341, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 351 corresponds also to sinuousness or curvature on the surface of the body, against which the conducting medium 351 is applied, so as to make the medium and body surface contiguous. As time-varying electrical current is passed through the coil 341, a magnetic field is produced, but because the coil winding is toroidal, the magnetic field is spatially restricted to the interior of the toroid. An electric field and eddy currents are also produced. The electric field extends beyond the toroidal space and into the patient's body, causing electrical currents and stimulation within the patient. The volume 351 is electrically connected to the patient at a target skin surface in order to significantly reduce the current passed through the coil 341 that is needed to accomplish stimulation of the patient's nerve or tissue. In a preferred embodiment of the magnetic stimulator that is shown in FIG. 5D, the conducting medium with which the coil 341 is in contact need not completely surround the toroid.

The design of the magnetic stimulator 301, which is adapted herein for use with surface electrodes, makes it possible to shape the electric field that is used to selectively stimulate a deep nerve such as a vagus nerve in the neck of a patient. Furthermore, the design produces significantly less pain or discomfort (if any) to a patient than stimulator devices that are currently known in the art. Conversely, for a given amount of pain or discomfort on the part of the patient (e.g., the threshold at which such discomfort or pain begins), the design achieves a greater depth of penetration of the stimulus under the skin.

Figure 1B:
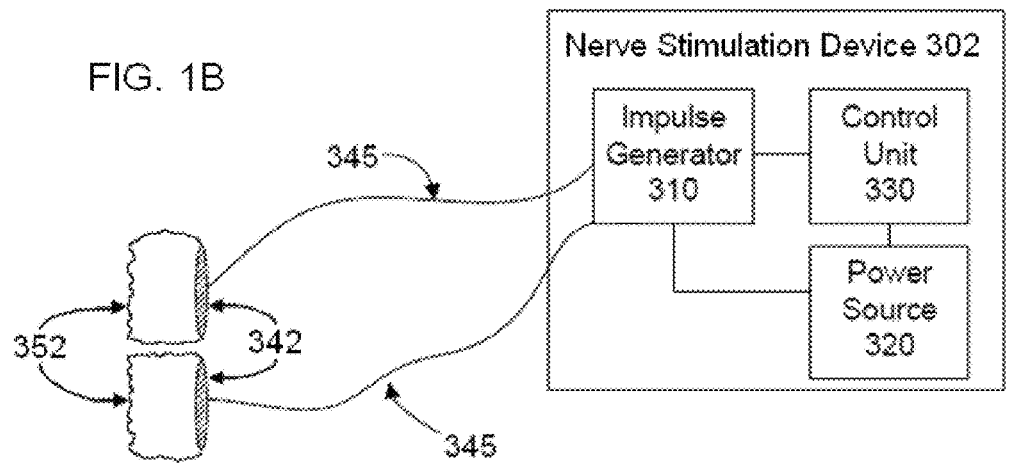

FIG. 1B shows an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 342 coupled via wires 345 to impulse generator 310. In a preferred embodiment, the same impulse generator 310, power source 320, and control unit 330 may be used for either the magnetic stimulator 301 or the electrode-based stimulator 302, allowing the user to change parameter settings depending on whether coils 341 or the electrodes 342 are attached.

Although a pair of electrodes 342 is shown in FIG. 1B, in practice the electrodes may also comprise three or more distinct electrode elements, each of which is connected in series or in parallel to the impulse generator 310. Thus, the electrodes 342 that are shown in FIG. 1B represent all electrodes of the device collectively.

The item labeled in FIG. 1B as 352 is a volume, contiguous with an electrode 342, that is filled with electrically conducting medium. As shown, the medium is also deformable such that it is form-fitting when applied to the surface of the body. Thus, the sinuousness or curvature shown at the outer surface of the electrically conducting medium 352 corresponds also to sinuousness or curvature on the surface of the body, against which the conducting medium 352 is applied, so as to make the medium and body surface contiguous. As described below in connection with a preferred embodiment, the volume 352 is electrically connected to the patient at a target skin surface in order to shape the current density passed through an electrode 342 that is needed to accomplish stimulation of the patient's nerve or tissue. As also described below in connection with embodiments of the invention, conducting medium with which the electrode 342 is in contact need not completely surround an electrode.

The control unit 330 controls the impulse generator 310 to generate a signal for each of the device's coils or electrodes. The signals are selected to be suitable for amelioration of a particular medical condition, when the signals are applied non-invasively to a target nerve or tissue via the coil 341 or electrodes 342. It is noted that nerve stimulating/modulating device 301 or 302 may be referred to by its function as a pulse generator. Patent application publications US2005/0075701 and US2005/0075702, both to SHAFER, both of which are incorporated herein by reference, relating to stimulation of neurons of the sympathetic nervous system to attenuate an immune response, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara, Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard and computer mouse as well as any externally supplied physiological signals, analog-to-digital converters for digitizing externally supplied analog signals, communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurlo, Przemyslaw Plonecki, Jacek Starzyński, Stanislaw Wincenciak, Andrzej Rysz. Mathematical Modeling of Vagus Nerve Stimulation. pp. 92-97 in: Krawczyk, A. Electromagnetic Field, Health and Environment: Proceedings of EHE'07. Amsterdam, IOS Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

Figure 2A:
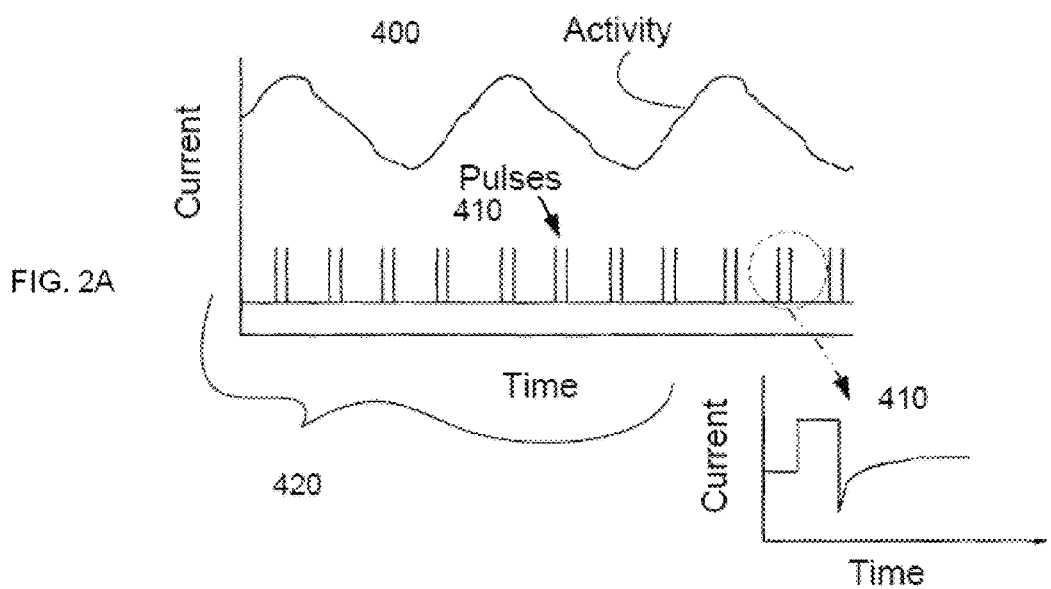
FIGS. 2A-2C illustrate an exemplary electrical voltage/current profile for a blocking and/or modulating impulses that are applied to a portion or portions of a nerve, in accordance with an embodiment of the present invention.

Referring now to FIG. 2, FIG. 2A illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are produced non-invasively within the patient by the magnetic stimulator or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the coil 341 or electrodes 342 that deliver the stimulating, blocking and/or modulating impulse 410 to the nerve. Nerve stimulating/modulating device 301 or 302 may be externally powered and/or recharged may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes, the device disclosed in patent publication No. US2005/0216062 (the entire disclosure of which is incorporated herein by reference) may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type the user wishes, who can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 50 Hz, more preferably around 25 Hz. The modulation signal may have a pulse width selected to influence the therapeutic result, such as about 20 microseconds or greater, such as about 20 microseconds to about 1000 microseconds. For example, the electric field induced by the device within tissue in the vicinity of a nerve is 10 to 600 V/m, preferably around 300 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz.

An objective of the stimulators disclosed herein is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385].

To date, the selection of stimulation waveform parameters for vagal nerve stimulation (VNS) has been highly empirical, in which the parameters are varied about some initially successful set of parameters, in an effort to find an improved set of parameters for each patient. A more efficient approach to selecting stimulation parameters might be to select a stimulation waveform that mimics electrical activity in the regions of the brain that one is attempting stimulate indirectly, in an effort to entrain the naturally occurring electrical waveform, as suggested in patent number U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to Begnaud, et al]. However, some VNS stimulation waveforms, such as those described herein, are discovered by trial and error, and then deliberately improved upon.

Invasive vagal nerve stimulation typically uses square wave pulse signals. The typical waveform parameter values for VNS therapy for epilepsy and depression are: a current between 1 and 2 mA, a frequency of between 20 and 30 Hz, a pulse width of 250-500 microseconds, and a duty cycle of 10% (signal ON time of 30 s, and a signal OFF time to 5 min). Output current is gradually increased from 0.25 mA to the maximum tolerable level (maximum, 3.5 mA), with typical therapeutic settings ranging from 1.0 to 1.5 mA. Greater output current is associated with increased side effects, including voice alteration, cough, a feeling of throat tightening, and dyspnea. Frequency is typically 20 Hz in depression and 30 Hz in epilepsy. The therapy is adjusted in a gradual, systematic fashion to individualize therapy for each patient. To treat migraine headaches, typical VNS parameters are a current of 0.25 to 1 mA, a frequency of 30 Hz, a pulse width of 500 microseconds, and an 'ON' time of 30 s every 5 min. To treat migraine plus epilepsy, typical parameters are 1.75 mA, a frequency of 20 Hz, a pulse width of 250 microseconds, and 'ON' time of 7 s followed by an 'OFF' time of 12 s. To treat mild to moderate Alzheimer's disease, typical VNS waveform parameters are: a current of 0.25 to 0.5 mA, a frequency of 20 Hz, a pulse width of 500 microseconds, and an 'ON' time of 30 s every 5 min. [ANDREWS, A. J., 2003. Neuromodulation. I. Techniques-deep brain stimulation, vagus nerve stimulation, and transcranial magnetic stimulation. Ann. N. Y. Acad. Sci. 993, 1-13; LABINER, D. M., Ahern, G. L., 2007. Vagus nerve stimulation therapy in depression and epilepsy: therapeutic parameter settings. Acta. Neurol. Scand. 115, 23-33; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060]. Applicant found that these square waveforms are not ideal for non-invasive VNS stimulation as they produce excessive pain.

Prepulses and similar waveform modifications have been suggested as means to improve selectivity of vagus and other nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figures 2B, 2C:
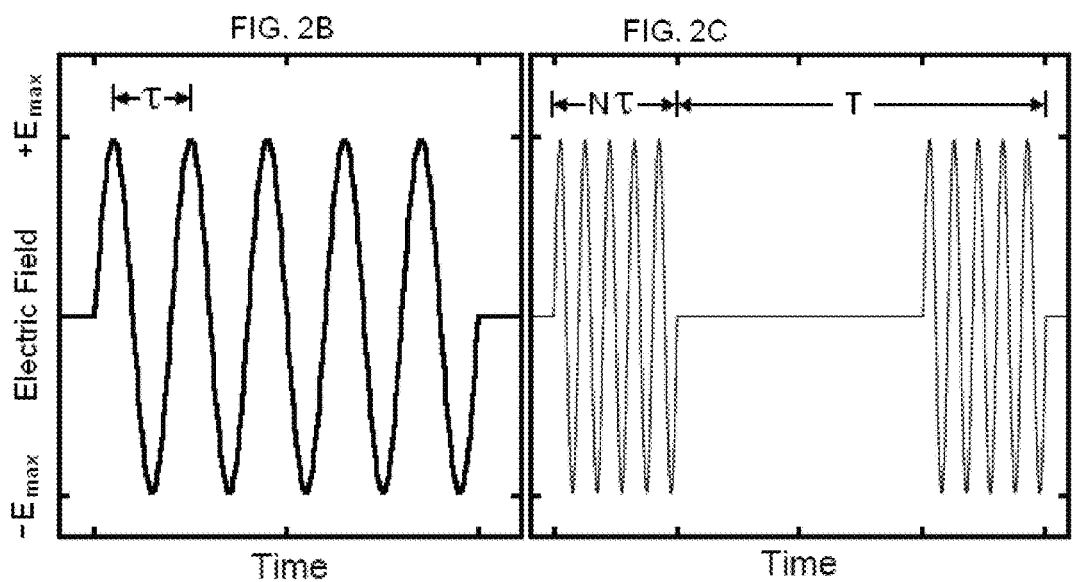

Applicant also found that stimulation waveforms consisting of bursts of square pulses are not ideal for non-invasive VNS stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2B and 2C. As seen there, individual sinusoidal pulses have a period of $\tau$, and a burst consists of N such pulses. This is followed by a period with no signal (the inter-burst period). The pattern of a burst plus followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds (a much smaller value of T is shown in FIG. 2C to make the bursts discernable). Applicant is unaware of such a waveform having been used with vagal nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein for VNS. Furthermore, the signal used for muscle strengthening may be other than sinusoidal (e.g., triangular), and the parameters $\tau$, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation: The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008):1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181]. By way of example, the electric field shown in FIGS. 2B and 2C may have an $E_{max}$ value of 17 V/m, which is sufficient to stimulate the vagus nerve but is significantly lower than the threshold needed to stimulate surrounding muscle.

In order to compare the electrical stimulator that is disclosed herein with existing electrodes and stimulators that have been used for non-invasive electrical stimulation, it is useful to first summarize the relevant physics of electric fields and currents that are produced by the electrodes. According to Maxwell's equation (Ampere's law with Maxwell correction): $\nabla \times B = J + \in (\partial E/\partial t)$, where B is the magnetic field, J is the electrical current density, E is the electric field, $\in$ is the permittivity, and t is time [Richard P. FEYNMAN, Robert B. Leighton, and Matthew Sands. The Feynman Lectures on Physics. Volume II. Addison-Wesley Publ. Co. (Reading, Mass., 1964), page 15-15].

According to Faraday's law, $\nabla \times E = -\partial B/\partial t$. However, for present purposes, changes in the magnetic field B may be ignored, so $\nabla \times E = 0$, and E may therefore be obtained from the gradient of a scalar potential $\Phi$: $E = \nabla \Phi$. In general, the scalar potential $\Phi$ and the electric field E are functions of position and time (t).

The electrical current density J is also a function of position (r) and time (t), and it is determined by the electric field and conductivity as follows, where the conductivity $\sigma$ is generally a tensor and a function of position (r): $J = \sigma E = \sigma \nabla \Phi$.

Because $\nabla \cdot \nabla \times B = 0$, Ampere's law with Maxwell's correction may be written as:

$\nabla \cdot J + \nabla \cdot \in (\partial E/\partial t) = 0$. If the current flows in material that is essentially unpolarizable (i.e., is presumed not to be a dielectric so that $\in = 0$), substitution of the expression for J into the above expression for Ampere's law gives $-\nabla \cdot (\sigma \nabla \Phi) = 0$, which is a form of Laplace's equation. If the conductivity of material in the device (or patient) is itself a function of the electric field or potential, then the equation becomes non-linear, which could exhibit multiple solutions, frequency multiplication, and other such non-linear behavior. The equation has been solved analytically for special electrode configurations, but for more general electrode configurations, it must be solved numerically [Petrus J. CILLIERS. Analysis of the current density distribution due to surface electrode stimulation of the human body. Ph.D. Dissertation, Ohio State University, 1988. (UMI Microform Number: 8820270, UMI Company, Ann Arbor Mich.); Martin REICHEL, Teresa Breyer, Winfried Mayr, and Frank Rattay. Simulation of the Three-Dimensional Electrical Field in the Course of Functional Electrical Stimulation. Artificial Organs 26(3, 2002):252-255; Cameron C. McINTYRE and Warren M. Grill. Finite Element Analysis of the Current-Density and Electric Field Generated by Metal Microelectrodes. Annals of Biomedical Engineering 29 (2001): 227-235; A. PATRICIU, T. P. DeMonte, M. L. G. Joy, J. J. Struijk. Investigation of current densities produced by surface electrodes using finite element modeling and current density imaging. Proceedings of the 23rd Annual EMBS International Conference, Oct. 25-28, 2001, Istanbul, Turkey: 2403-2406; Yong H U, X B Xie, L Y Pang, X H Li K D K Luk. Current Density Distribution Under Surface Electrode on Posterior Tibial Nerve Electrical Stimulation. Proceedings of the 2005 IEEE Engineering in Medicine and Biology 27th Annual Conference Shanghai, China, Sep. 1-4, 2005: 3650-3652].

The equation has also been solved numerically in order to compare different electrode shapes and numbers [Abhishek DATTA, Maged Elwassif, Fortunato Battaglia and Marom Bikson. Transcranial current stimulation focality using disc and ring electrode configurations: FEM analysis. J. Neural Eng. 5 (2008) 163-174; Jay T. RUBENSTEIN, Francis A. Spelman, Mani Soma and Michael F. Suesserman. Current Density Profiles of Surface Mounted and Recessed Electrodes for Neural Prostheses. IEEE Transactions on Biomedical Engineering BME-34 (11, 1987): 864-875; David A. KSIENSKI. A Minimum Profile Uniform Current Density Electrode. IEEE Transactions on Biomedical Engineering 39 (7, 1992): 682-692; Andreas KUHN, Thierry Keller, Silvestro Micera, Manfred Morari. Array electrode design for transcutaneous electrical stimulation: A simulation study. Medical Engineering & Physics 31 (2009) 945-951]. The calculated electrical fields may be confirmed using measurements using a phantom [A. M. SAGI_DOLEV, D. Prutchi and R. H. Nathan. Three-dimensional current density distribution under surface stimulation electrodes. Med. and Biol. Eng. and Comput. 33(1995): 403-408].

If capacitive effects cannot be ignored, an additional term involving the time-derivative of the gradient of the potential appears in the more general expression, as obtained by substituting the expressions for J and E into the divergence of Ampere's law with Maxwell's correction:

$$-\nabla \cdot (\sigma \nabla \Phi) - \nabla \cdot (\in \nabla (\partial \Phi / \partial t)) = 0$$

The permittivity $\in$ is a function of position (r) and is generally a tensor. It may result from properties of the body and may also be a property of the electrode design [L. A. GEDDES, M. Hinds and K. S. Foster. Stimulation with capacitor electrodes. Med. and Biol. Eng. and Comput. 25(1987):359-360]. As a consequence of such a term, the waveform of the electrical potential at points within the body will generally be altered relative to the waveform of the voltage signal(s) applied to the electrode(s). Furthermore, if the permittivity of a material in the device itself (or patient) is a function of the electric field or potential, then the equation becomes non-linear, which could exhibit multiple solutions, frequency multiplication, and other such non-linear behavior. This time-dependent equation has been solved numerically [KUHN A, Keller T. A 3D transient model for transcutaneous functional electrical stimulation. Proc. 10th Annual Conference of the International FES Society July 2005—Montreal, Canada: pp. 1-3; Andreas KUHN, Thierry Keller, Marc Lawrence, Manfred Morari. A model for transcutaneous current stimulation: simulations and experiments. Med Biol Eng Comput 47(2009):279-289; N. FILIPOVIC, M. Nedeljkovic, A. Peulic. Finite Element Modeling of a Transient Functional Electrical Stimulation. Journal of the Serbian Society for Computational Mechanics 1 (1, 2007):154-163; Todd A. KUIKEN, Nikolay S. Stoykov, Milica Popovic, Madeleine Lowery and Allen Taflove. Finite Element Modeling of Electromagnetic Signal Propagation in a Phantom Arm. IEEE Transactions on Neural Systems and Rehabilitation Engineering 9 (4, 2001): 346-354].

In any case, Dirichlet (D) boundary conditions define voltage sources, and Neumann (N) boundary conditions describe the behavior of the electric field at the crossover boundary from skin to air, as follows:

$$N: \partial \Phi / \partial n = \sigma(r) \text{ and } D: \Phi = V(t)$$

where n denotes the outward pointing normal vector, i.e., the vector orthogonal to the boundary curve; and V(t) denotes the voltage applied to an electrode. Thus, no conduction current can flow across an air/conductor interface, so according to the interfacial boundary conditions, the component of any current normal to the an air/conductor interface must be zero. In constructing the above differential equation for $\Phi$ as a function of time, the divergence of J is taken, which satisfies the continuity equation: $\nabla \cdot J = -\partial \rho / \partial t$, where $\rho$ is the charge density. Conservation of charge requires that sides of this equation equal zero everywhere except at the surface of the electrode where charge is impressed upon the system (injected or received).

It is an objective of the present invention to shape an elongated electric field of effect that can be oriented parallel to a long nerve such as the vagus nerve in the neck. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which current flow is restricted. Shaping of the electric field refers both to the circumscribing of regions within which there is a significant electric field and to configuring the directions of the electric field within those regions. Our invention does so by configuring elements that are present within the equations that were summarized above, comprising (but not limited to) the following exemplary configurations that may be used alone or in combination.

First, different contours or shapes of the electrodes affect $\nabla \cdot J$. For example, charge is impressed upon the system (injected or received) differently if an electrode is curved versus flat, or if there are more than two electrodes in the system.

Second, values of the voltage V(t) in the above boundary condition is manipulated to shape the electric field. For example, if the device contains two pairs of electrodes that are perpendicular or at a variable angle with respect to one another, the waveform of the voltage across one pair of electrodes may be different than the waveform of the voltage across the second pair, so that the superimposed electric fields that they produce may exhibit beat frequencies, as has been attempted with electrode-based stimulators [U.S. Pat. No. 5,512,057, entitled Interferential stimulator for applying localized stimulation, to REISS et al.], and acoustic stimulators [U.S. Pat. No. 5,903,516, entitled Acoustic force generator for detection, imaging and information transmission using the beat signal of multiple intersecting sonic beams, to GREENLEAF et al].

Third, the scalar potential (D in the above equation $\partial \Phi / \partial n = \sigma(r)$ may be manipulated to shape the electric field. For example, this is accomplished by changing the boundaries of conductor/air (or non-conductor) interfaces, thereby creating different boundary conditions. For example, the conducting material may pass through conducting apertures in an insulated mesh before contacting the patient's skin, creating thereby an array of electric field maxima. As another example, an electrode may be disposed at the end of a long tube that is filled with conducting material, or the electrode may be situated at the bottom of a curved cup that is filled with conducting material. In those cases the dimensions of the tube or cup would affect the resulting electric fields and currents.

Fourth, the conductivity $\sigma$ (in the equation $J = \sigma E$) may be varied spatially within the device by using two or more different conducting materials that are in contact with one another, for given boundary conditions. The conductivity may also be varied by constructing some conducting material from a semiconductor, which allows for adjustment of the conductivity in space and in time by exposure of the semiconductor to agents to which they are sensitive, such as electric fields, light at particular wavelengths, temperature, or some other environmental variable over which the user of the device has control. For the special case in which the semiconductor's conductivity may be made to approach zero, that would approximate the imposition of an interfacial boundary condition as described in the previous paragraph.

Fifth, a dielectric material having a high permittivity E, such as Mylar, neoprene, titanium dioxide, or strontium titanate, may be used in the device, for example, in order to permit capacitative electrical coupling to the patient's skin. Changing the permittivity in conjunction along with changing the waveform V(t) would especially affect operation of the device, because the permittivity appears in a term that is a function of the time-derivative of the electric potential: $\nabla \cdot (\in \nabla (\partial \Phi / \partial t))$.

In configurations of the present invention, an electrode is situated in a container that is filled with conducting material. The disclosure below applies as well to conducting material within the magnetic stimulation device. In one embodiment, the container contains holes so that the conducting material (e.g., a conducting gel) can make physical contact with the patient's skin through the holes. For example, the conducting medium 351 in FIG. 1A or 352 in FIG. 1B may comprise a chamber surrounding the electrode, filled with a conductive gel that has the approximate viscosity and mechanical consistency of gel deodorant (e.g., Right Guard Clear Gel from Dial Corporation, 15501 N. Dial Boulevard, Scottsdale, Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue.

Agar can also be used as part of the conducting medium, but it is not preferred, because agar degrades in time, is not ideal to use against skin, and presents difficulties with cleaning the patient. Rather than using agar as the conducting medium, an electrode can instead be in contact with in a conducting solution such as 1-10% NaCl that also contacts an electrically conducting interface to the human tissue. Such an interface is useful as it allows current to flow from the electrode into the tissue and supports the conducting medium, wherein the device can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J Martens. Conducting polymerhydrogels for medical electrode applications. Sci. Technol. Adv. Mater. 11 (2010) 014107 (13 pp)]. For example it may be the following hypoallergenic, bacteriostatic electrode gel: SIGNAGEL Electrode Gel from Parker Laboratories, Inc., 286 Eldridge Rd., Fairfield, N.J. 07004. Another example is the KM10T hydrogel from Katecho Inc., 4020 Gannett Ave., Des Moines, Iowa 50321.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the electrode and conducting solution in from the tissue, yet allow current to pass.

The electrode-base based stimulator in FIG. 1B shows two equivalent electrodes 342, side-by-side, wherein electrical current would pass through the two electrodes in opposite directions. Thus, the current will flow from one electrode, through the tissue and back through the other electrode, completing the circuit within the electrodes' conducting media that are separated from one another. An advantage of using two equivalent electrodes in this configuration is that this design will increase the magnitude of the electric field gradient between them, which is crucial for exciting long, straight axons such as the vagus nerve in the neck and other deep peripheral nerves.

Figure 3A:
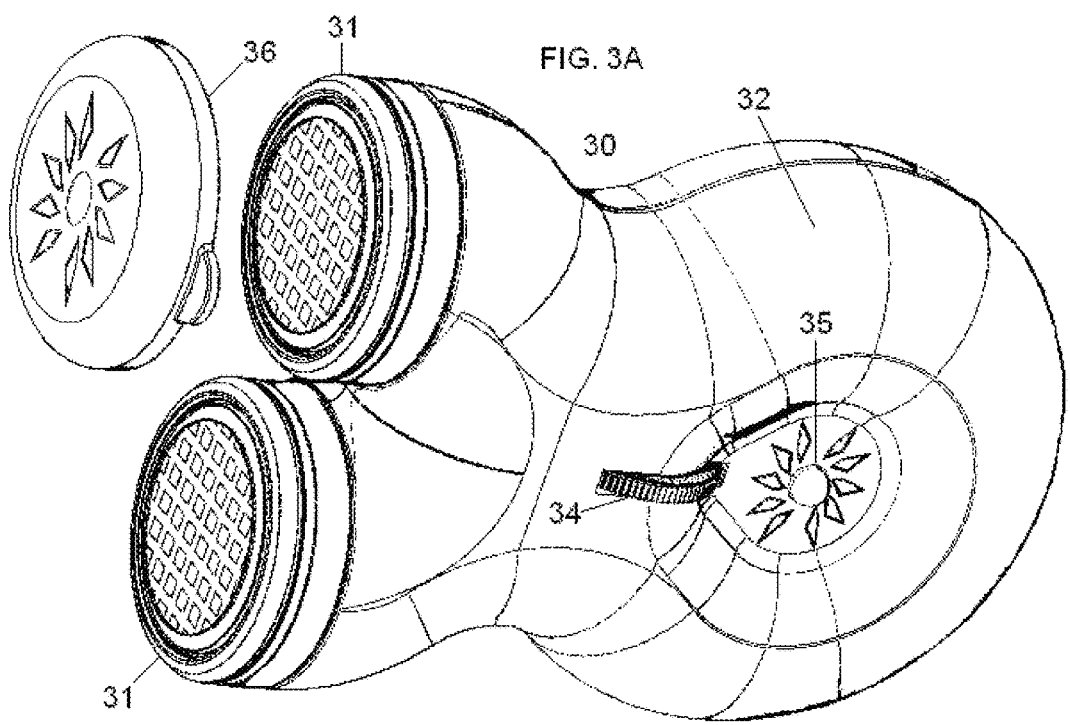
FIGS. 3A-3B illustrate a dual-electrode stimulator according to an embodiment of the present invention, which is shown to house the stimulator's electrodes and electronic components.
Figure 3B:
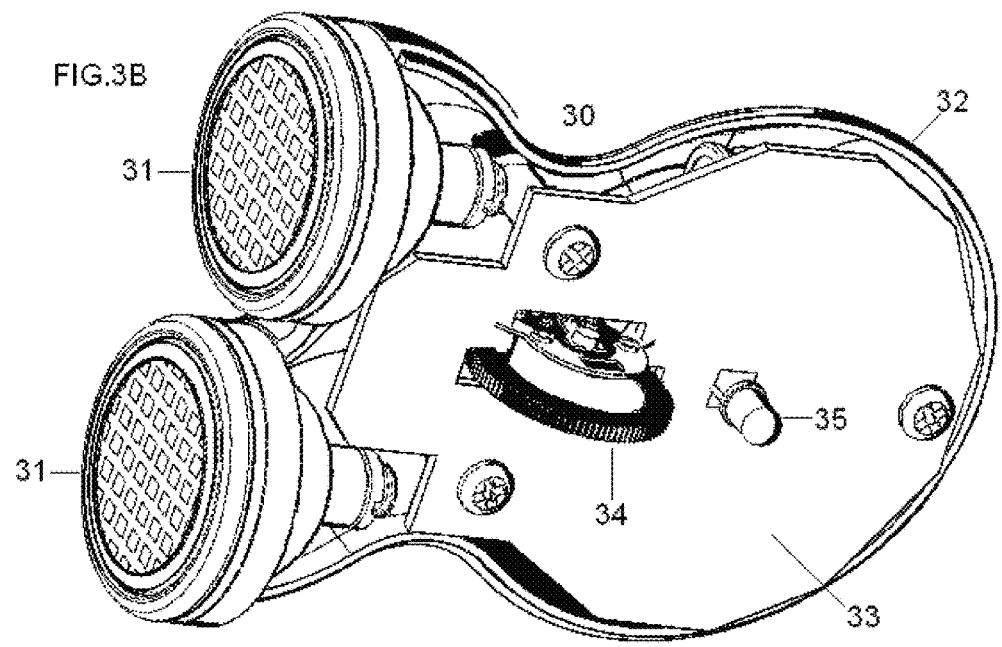

A preferred embodiment of the electrode-based stimulator is shown in FIG. 3A. A cross-sectional view of the stimulator along its long axis is shown in FIG. 3B. As shown, the stimulator 30 comprises two heads 31 and a body 32 that joins them. Each head 31 contains a stimulating electrode. The body of the stimulator 32 contains the electronic components and battery (not shown) that are used to generate the signals that drive the electrodes, which are located behind the insulating board 33 that is shown in FIG. 3B. However, in other embodiments of the invention, the electronic components that generate the signals that are applied to the electrodes may be separate, but connected to the electrode head 31 using wires. Furthermore, other embodiments of the invention may contain a single such head or more than two heads.

Heads of the stimulator 31 are applied to a surface of the patient's body, during which time the stimulator may be held in place by straps or frames (not shown), or the stimulator may be held against the patient's body by hand. In either case, the level of stimulation power may be adjusted with a wheel 34 that also serves as an on/off switch. A light 35 is illuminated when power is being supplied to the stimulator. Thus, in this embodiment of the invention, mechanical and electronic components of the stimulator (impulse generator, control unit, and power source) are compact, portable, and simple to operate. A cap 36 is provided to cover each of the stimulator heads 31, to protect the device when not in use, to avoid accidental stimulation, and to prevent material within the head from leaking or drying. However, for embodiments of the stimulator head in which the head is covered with Mylar or some other high-dielectric material that can capacitively couple the signal to the skin, the Mylar may completely seal the gel within the stimulator head, thereby preventing exposure of the gel to the outside. In that case, there would be no gel evaporation. Then, the cap 36 would be less advantageous because the head can be cleaned between stimulation sessions (e.g., with isopropyl alcohol) with no chance of contaminating the internal gel.

Figure 4A:
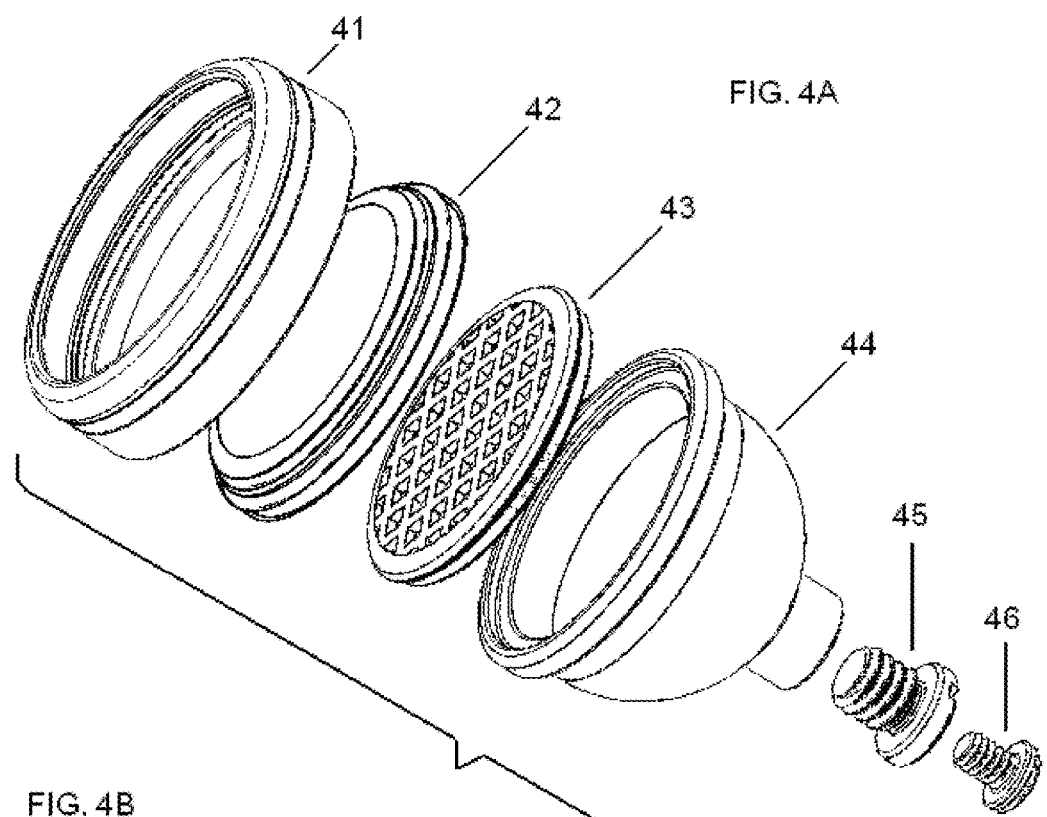
Figure 4B:
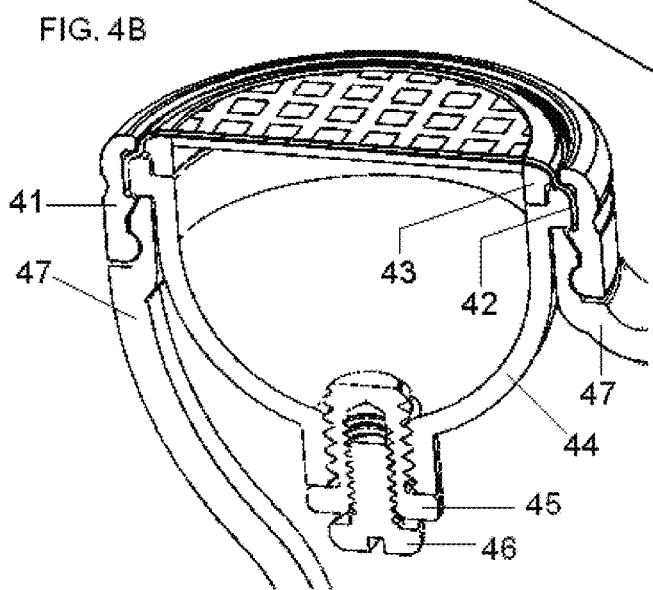

Construction of the stimulator head is shown in more detail in FIG. 4. In the embodiment shown in FIGS. 4A and 4B, the stimulator head contains an aperture screen, but in the embodiment shown in FIGS. 4C and 4D, there is no aperture screen. Referring now to the exploded view shown in FIG. 4A, the electrode head is assembled from a snap-on cap 41 that serves as a tambour for a conducting membrane 42, an aperture screen 43, the head-cup 44, the electrode which is also a screw 45, and a lead-mounting screw 46 that is inserted into the electrode 45. The electrode 45 seen in each stimulator head has the shape of a screw that is flattened on its tip. Pointing of the tip would make the electrode more of a point source, such that the above-mentioned equations for the electrical potential may have a solution corresponding more closely to a far-field approximation. Rounding of the electrode surface or making the surface with another shape will likewise affect the boundary conditions. Completed assembly of the stimulator head is shown in FIG. 4B, which also shows how the head is attached to the body of the stimulator 47.

As examples, the conducting membrane 42 may be a sheet of Tecophlic material from Lubrizol Corporation, 29400 Lakeland Boulevard, Wickliffe, Ohio 44092. The apertures may be open, or they may be plugged with conducting material, for example, KM10T hydrogel from Katecho Inc., 4020 Gannett Ave., Des Moines, Iowa 50321. If the apertures are so-plugged, the conducting membrane 42 becomes optional. The head-cup 44 is filled with conducting material, for example, SIGNAGEL Electrode Gel from Parker Laboratories, Inc., 286 Eldridge Rd., Fairfield, N.J. 07004. The snap-on cap 41, aperture screen 43, head-cup 44 and body of the stimulator are made of a non-conducting material, such as acrylonitrile butadiene styrene. The depth of the head-cup from its top surface to the electrode may be between one and six centimeters. The head-cup may have a different curvature than what is shown in FIG. 4, or it may be tubular or conical or have some other inner surface geometry that will affect the Neumann boundary conditions.

The alternate embodiment of the stimulator head that is shown in FIG. 4C also contains a snap-on cap 41, a conducting membrane 42, the head-cup 44, the electrode which is also a screw 45, and a lead-mounting screw 46 that is inserted into the electrode 45. This alternate embodiment differs from the embodiment shown in FIGS. 4A and 4B in regard to the mechanical support that is provided to the conducting membrane 42. Whereas the aperture screen had provided mechanical support to the membrane in the other embodiment, in the alternate embodiment a reinforcing ring 40 is provided to the membrane. That reinforcement ring rests on non-conducting struts 49 that are placed in the head-cup 44, and a non-conducting strut-ring 48 is placed within notches in the struts 49 to hold the struts in place. An advantage of the alternate embodiment is that without apertures, current flow is less restricted through the conducting membrane 42. Furthermore, although the struts and strut-ring are made of non-conducting material in this alternate embodiment, the design may be adapted to position additional electrode or other conducting elements within the head-cup for other more specialized configurations of the stimulator head, the inclusion of which will influence the electric fields that are generated by the device. Completed assembly of the alternate stimulator head is shown in FIG. 4D, without showing attachment to the body of the stimulator, and without showing the insertion of the lead-mounting screw 46. In fact, it is also possible to insert a lead under the head of the electrode 45, and many other methods of attaching the electrode to the signal-generating electronics of the stimulator are known in the art.

Another embodiment of the electrode-based stimulator is shown in FIG. 5, showing a device in which electrically conducting material is dispensed from the device to the patient's skin. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

Figure 5A:
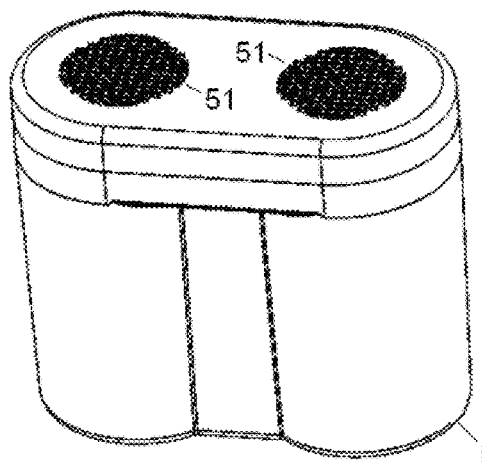
FIGS. 5A-5D illustrate an alternate embodiment of the dual-electrode stimulator, also comparing it with an embodiment of the magnetic stimulator according to the present invention.
Figure 5B:
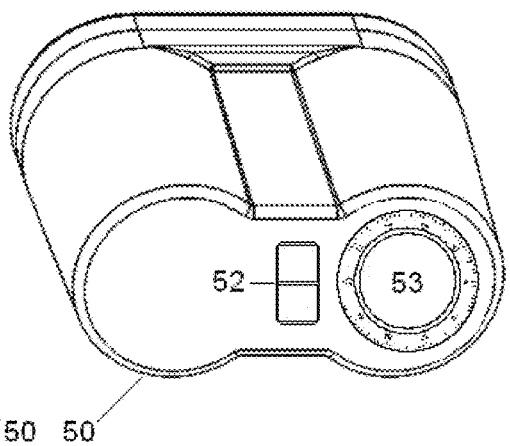
Figure 5C:
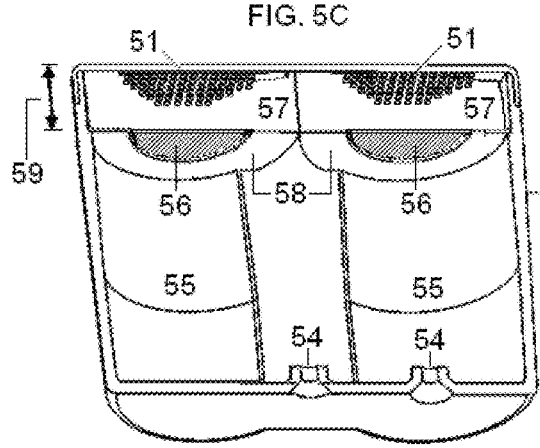
Figure 5D:
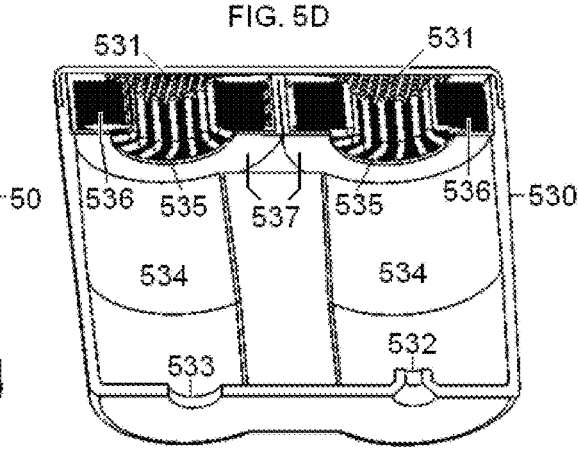

FIGS. 5A and 5C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 5A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 5B and 5C show the bottom of the self-contained stimulator 50. An on/off switch 52 is attached through a port 54, and a power-level controller 53 is attached through another port 54. The switch is connected to a battery power source (320 in FIG. 1B), and the power-level controller is attached to the control unit (330 in FIG. 1B) of the device. The power source battery and power-level controller, as well as the impulse generator (310 in FIG. 1B) are located (but not shown) in the rear compartment 55 of the housing of the stimulator 50.

Individual wires (not shown) connect the impulse generator (310 in FIG. 1B) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (352 in FIG. 1B) to each head compartment 57. In addition, a non-conducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another.

In a preferred embodiment, the magnetic stimulator coil 341 in FIG. 1A has a body that is similar to the electrode-based stimulator shown in FIG. 5C. To compare the electrode-based stimulator with the magnetic stimulator, refer to FIG. 5D, which shows the magnetic stimulator 530 sectioned along its long axis to reveal its inner structure. As described below, it reduces the volume of conducting material that must surround a toroidal coil, by using two toroids, side-by-side, and passing electrical current through the two toroidal coils in opposite directions. In this configuration, the induced electrical current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

As seen in FIG. 5D, a mesh 531 has openings that permit a conducting gel (within 351 in FIG. 1A) to pass from the inside of the stimulator to the surface of the patient's skin at the location of nerve or tissue stimulation. Thus, the mesh with openings 531 is the part of the magnetic stimulator that is applied to the skin of the patient.

FIG. 5D also shows openings at the opposite end of the magnetic stimulator 530. One of the openings is an electronics port 532 through which wires pass from the stimulator coil(s) to the impulse generator (310 in FIG. 1A). The second opening is a conducting gel port 533 through which conducting gel (351 in FIG. 1A) may be introduced into the magnetic stimulator 530 and through which a screw-driven piston arm may be introduced to dispense conducting gel through the mesh 531. The gel itself is contained within cylindrical-shaped but interconnected conducting medium chambers 534 that are shown in FIG. 5D. The depth of the conducting medium chambers 534, which is approximately the height of the long axis of the stimulator, affects the magnitude of the electric fields and currents that are induced by the magnetic stimulator device [Rafael CARBUNARU and Dominique M. Durand. Toroidal coil models for transcutaneous magnetic stimulation of nerves. IEEE Transactions on Biomedical Engineering. 48 (No. 4, April 2001): 434-441].

FIG. 5D also show the coils of wire 535 that are wound around toroidal cores 536, consisting of high-permeability material (e.g., Supermendur). Lead wires (not shown) for the coils 535 pass from the stimulator coil(s) to the impulse generator (310 in FIG. 1A) via the electronics port 532. Different circuit configurations are contemplated. If separate lead wires for each of the coils 535 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As also seen in FIG. 5D, the coils 535 and cores 536 around which they are wound are mounted as close as practical to the corresponding mesh 531 with openings through which conducting gel passes to the surface of the patient's skin. As shown, each coil and the core around which it is wound is mounted in its own housing 537, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium. A difference between the structure of the electrode-based stimulator shown in FIG. 5C and the magnetic stimulator shown in FIG. 5D is that the conducting gel is maintained within the chambers 57 of the electrode-based stimulator, which is generally closed on the back side of the chamber because of the presence of the electrode 56; but in the magnetic stimulator, the hole of each toroidal core and winding is open, permitting the conducting gel to enter the interconnected chambers 534.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance. The currents passing through the coils of the magnetic stimulator will saturate the core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described in connection with FIG. 2. Additional disclosure of the magnetic stimulator shown in FIG. 1A is provided in Applicant's commonly assigned co-pending U.S. patent application Ser. No. 12/964,050 entitled Magnetic Stimulation Devices and Methods of Therapy, to SIMON et al., which is hereby incorporated by reference for all purposes.

In preferred embodiments of the electrode-based stimulator shown in FIG. 1B, electrodes are made of a metal, such as stainless steel. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18(2, 2008):35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20(1, 1994):29-35].

For example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71(1991):746-751].

Although the electrode may consist of arrays of conducting material, the embodiments shown in FIGS. 3 to 5 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6, 2005):448-452; Dejan B. POPOVIC and Mirjana B. Popovic. Automatic determination of the optimal shape of a surface electrode: Selective stimulation. Journal of Neuroscience Methods 178 (2009) 174-181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 3 to 5 provide a uniform surface current density, which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stødkilde-Jørgensen. Current Density Imaging and Electrically Induced Skin Burns Under Surface Electrodes. IEEE Transactions on Biomedical Engineering 52 (12, 2005): 2024-2031; R. H. GEUZE. Two methods for homogeneous field defibrillation and stimulation. Med. and Biol. Eng. and Comput. 21(1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6, 2006): 368-381; Russell G. MAUS, Erin M. McDonald, and R. Mark Wightman. Imaging of Nonuniform Current Density at Microelectrodes by Electrogenerated Chemiluminescence. Anal. Chem. 71(1999): 4944-4950]. In fact, patients found the design shown in FIGS. 3 to 5 to be less painful in a direct comparison with a commercially available grid-pattern electrode [UltraStim grid-pattern electrode, Axelggard Manufacturing Company, 520 Industrial Way, Fallbrook, Calif., 2011].

The electrode-based stimulator designs shown in FIGS. 3 to 5 situate the electrode remotely from the surface of the skin within a chamber, with conducting material placed in the chamber between the skin and electrode. Such a chamber design had been used prior to the availability of flexible, flat, disposable electrodes [U.S. Pat. No. 3,659,614, entitled Adjustable headband carrying electrodes for electrically stimulating the facial and mandibular nerves, to Jankelson; U.S. Pat. No. 3,590,810, entitled Biomedical body electrode, to Kopecky; U.S. Pat. No. 3,279,468, entitled Electrotherapeutic facial mask apparatus, to Le Vine; U.S. Pat. No. 6,757,556, entitled Electrode sensor, to Gopinathan et al; U.S. Pat. No. 4,383,529, entitled Iontophoretic electrode device, method and gel insert, to Webster; U.S. Pat. No. 4,220,159, entitled Electrode, to Francis et al. U.S. Pat. No. 3,862,633, U.S. Pat. No. 4,182,346, and U.S. Pat. No. 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 3 to 5 are also self-contained units, housing the electrodes, signal electronics, and power supply. Portable stimulators are also known in the art, for example, patent U.S. Pat. No. 7,171,266, entitled Electro-acupuncture device with stimulation electrode assembly, to Gruzdowich. One of the many novelties of the designs shown in FIGS. 3 to 5 is that two or more remote electrodes are configured for placement relative to the axis of a deep, long nerve, such that the stimulator along with a correspondingly suitable stimulation waveform shapes the electric field, producing a selective physiological response by stimulating that nerve, but avoiding substantial stimulation of nerves and tissue other than the target nerve, particularly avoiding the stimulation of nerves that produce pain.

Examples in the remaining disclosure will be directed to methods for using the disclosed electrical stimulation devices for treating a patient. Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6:
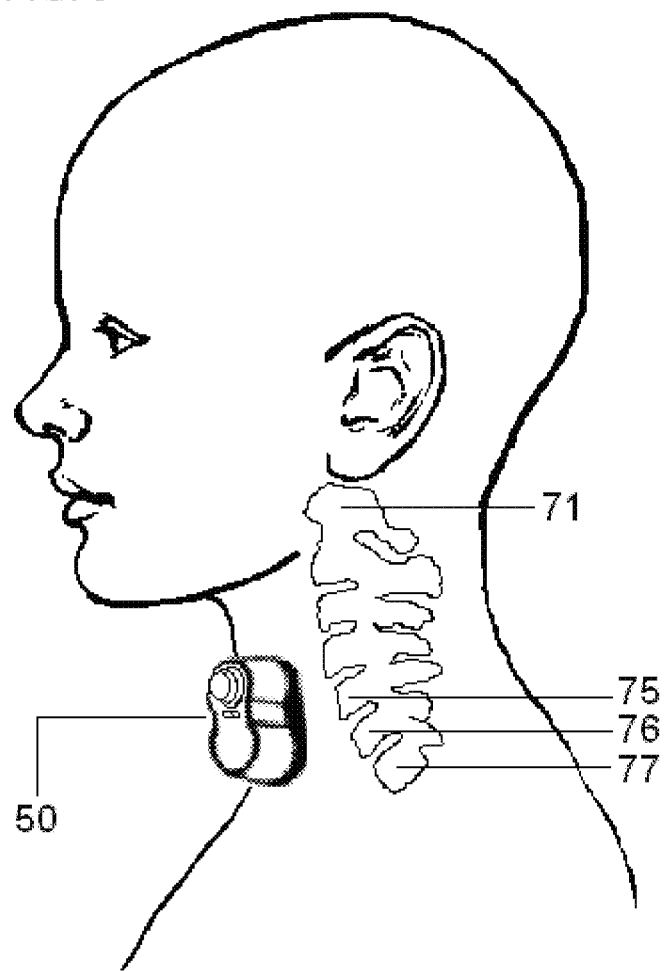
FIG. 6 illustrates the approximate position of the housing of a stimulator according one embodiment of the present invention, when the stimulator is used to stimulate the vagus nerve in the neck of a patient.

FIG. 6 illustrates use of the devices shown in FIGS. 3 to 5 to stimulate the vagus nerve at that location in the neck, in which the stimulator device 50 in FIG. 5 is shown to be applied to the target location on the patient's neck as described above. The illustration would also apply to the application of the magnetic stimulator device 530 in FIG. 5D. For reference, locations of the following vertebrae are also shown: first cervical vertebra 71, the fifth cervical vertebra 75, the sixth cervical vertebra 76, and the seventh cervical vertebra 77.

Figure 7:
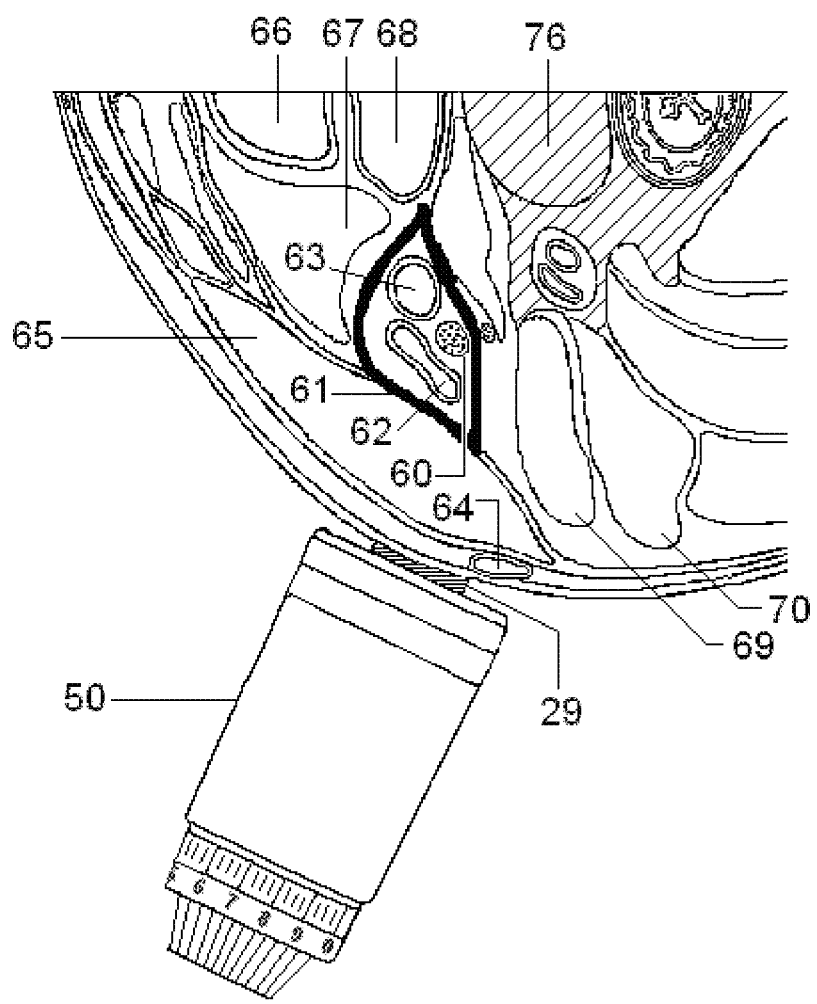
FIG. 7 illustrates the housing of a stimulator according one embodiment of the present invention, as the stimulator is positioned to stimulate the vagus nerve in a patient's neck via electrically conducting gel (or some other conducting material), which is applied to the surface of the neck in the vicinity of the identified anatomical structures.

FIG. 7 provides a more detailed view of use of the electrical stimulator, when positioned to stimulate the vagus nerve at the neck location that is indicated in FIG. 6. As shown, the stimulator 50 in FIG. 5 touches the neck indirectly, by making electrical contact through conducting gel 29 (or other conducting material) which may be is dispensed through mesh openings (identified as 51 in FIG. 5) of the stimulator or applied as an electrode gel or paste. The layer of conducting gel 29 in FIG. 7 is shown to connect the device to the patient's skin, but it is understood that the actual location of the gel layer(s) may be generally determined by the location of mesh 51 shown in FIG. 5. Furthermore, it is understood that for other embodiments of the invention, the conductive head of the device may not necessitate the use of additional conductive material being applied to the skin. The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

If it is desired to maintain a constant intensity of stimulation in the vicinity of the vagus nerve (or any other nerve or tissue that is being stimulated), methods may also be employed to modulate the power of the stimulator in order to compensate for patient motion or other mechanisms that would otherwise give rise to variability in the intensity of stimulation. In the case of stimulation of the vagus nerve, such variability may be attributable to the patient's breathing, which may involve contraction and associated change in geometry of the sternocleidomastoid muscle that is situated close to the vagus nerve (identified as 65 in FIG. 7). Methods for compensating for motion and other confounding factors were disclosed by the present applicant in commonly assigned co-pending application Ser. No. 12/859,568, entitled Non-Invasive Treatment of Bronchial Constriction, to SIMON, which is hereby incorporated by reference.

Methods of treating a patient comprise stimulating the vagus nerve as indicated in FIGS. 6 and 7, using the electrical or magnetic stimulation devices that are disclosed herein. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to produce a therapeutic result in the patient. Stimulation parameters for each patient are adjusted on an individualized basis. Ordinarily, the amplitude of the stimulation signal is set to the maximum that is comfortable for the patient, and then the other stimulation parameters are adjusted.

In other embodiments of the invention, pairing of vagus nerve stimulation may be with a time-varying sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect. For example, the hypothalamus is well known to be responsive to the presence of bright light, so exposing the patient to bright light that is fluctuating with the same stimulation frequency as the vagus nerve (or a multiple of that frequency) may be performed in an attempt to enhance the role of the hypothalamus in producing the desired therapeutic effect. For migraine headaches, the desired effect is to reduce the frequency of migraines and/or the reduction of migraine pain and its duration [D. J. ANDERSON. The Treatment of Migraine with Variable Frequency Photo-Stimulation. Headache 29(1989):154-155; David NOTON. Migraine and photic stimulation: report on a survey of migraineurs using flickering light therapy. Complementary Therapies in Nursing and Midwifery 6(2000): 138-142]. Such paired stimulation does not rely upon neuronal plasticity and is in that sense different from other reports of paired stimulation [Navzer D. ENGINEER, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature (2011): published online doi:10.1038/nature09656].

Use of the above-described devices and methods to treat migraine headaches is now disclosed. Migraine headache is a disorder of the brain characterized by a complex, but stereotypical, dysfunction of sensory processing. The annual prevalence of migraine is 6-9% among men and 15-17% among women. Migraine appears in all ages but reaches a peak in middle age, decreasing in old age. Migraine headaches often occur on both sides of the head in children, but then an adult pattern of unilateral pain often emerges in adolescence. Migraine headache pain is usually located in the temple, forehead or eye, or back of the head, sometimes reported as starting in the occipital/neck regions, and later becoming fronto-temporal. The pain is throbbing and aggravated by physical effort. Approximately 20-30% of migraine sufferers (migraineurs) experience an aura, ordinarily a visual aura. The aura typically lasts for 5 minutes to an hour, during which time the patient experiences sensations such as moving zig-zag flashes of light, blind spots or tingling in the hand or face. Allodynia (perception of pain when a usually nonpainful stimulus is applied, such as hair combing) is reported in about two-thirds of migraineurs during the attack [SCHER A I, Stewart W F, Ricci J A, Lipton R B. Factors associated with the onset and remission of chronic daily headache in a population-based study. Pain. 106(2003):81-89; Bert B. VARGAS, David W. Dodick. The Face of Chronic Migraine: Epidemiology, Demographics, and Treatment Strategies. Neurol Clin 27 (2009): 467-479].

Both twin studies and population-based epidemiological surveys strongly suggest that migraine without aura is a multifactorial disorder, caused by a combination of genetic and environmental factors. Inherited susceptibility for common migraine (without or with aura) involves a gene sequence variant on chromosome 8, which is flanked between two genes (PGCP and MTDH/AEG-1) that are involved in glutamate homeostasis. MTDH/AEG-1 regulates the activity of the EAAT2 gene product, which is responsible for clearing glutamate from brain synapses in the brain. Plasma glutamate carboxypeptidase (PGCP) is a proteinase that acts on the unsubstituted N- and C-termini of dipeptides, which like other glutamate carboxypeptidases may regulate the concentration of glutamate in the extra cellular space.

Migraine with aura has an even stronger genetic basis. Families with Familial Hemiplegic Migraine (FHM) most often have a mutation involving a Cav2.1 (P/Q) type voltage-gated calcium channel on chromosome 19. In other families with FHM, a mutation occurs on chromosome 1 in a gene encoding the A2 subunit of the Na+, K+ ATPase. A third mutant gene that is located on chromosome 2, a neuronal voltage-gated sodium channel, has also been found to produce FHM.

Some migraine sufferers become symptom-free for long periods of time. Others continue to have headaches with fewer or less typical migraine features, resembling tension-type headaches, rather than full-blown migraine. Considering the above-mentioned age-related incidence of migraine, this may be partly due to aging. It may also be due to the migraineur learning to avoid the factors that trigger migraines or to successful prophylactic treatment [SCHER A I, Stewart W F, Ricci J A, Lipton R B. Factors associated with the onset and remission of chronic daily headache in a population-based study. Pain 106(2003):81-89; BOARDMAN H F, Thomas E, Millson D S, Croft P R. The natural history of headache: predictors of onset and recovery Cephalalgia 26(2006):1080-1088; BIGAL M E, Lipton R B. Modifiable risk factors for migraine progression. Headache 46(9, 2006):1334-43; BIGAL M E, Lipton R B. Modifiable risk factors for migraine progression (or for chronic daily headaches)—clinical lessons. Headache 46 (Suppl 3, 2006): 5144-6].

Migraine attacks may also continue over many years without major changes in frequency, severity or symptoms. In some migraineurs, migraine attack frequency and disability may increase over time, in which there may be a progression from episodic migraine to chronic (chronified or transformed) migraine. The progression may be due to treatment exacerbating the problem, to unsuccessful or futile avoidance of triggers, or conceivably to progressive neurological changes that are analogous to progressive neurodegeneration [Paul R. MARTIN and Colin MacLeod. Behavioral management of headache triggers: Avoidance of triggers is an inadequate strategy. Clinical Psychology Review 29 (2009) 483-495]. Attempts have been made to document progressive neurological changes in migraineurs so as better understand putative progression [VALFRE W, Rainero I, Bergui M, Pinessi L. Voxel-based morphometry reveals grey matter abnormalities in migraine Headache 48(2008):109-17]. However, conclusions drawn from brain imaging of migraineurs are controversial because observed progressive changes might not be irreversible [Arne May. Morphing voxels: the hype around structural imaging of headache patients. Brain 132(2009): 1419-1425]. Such imaging may be most useful in conjunction with biomarkers that do not involve brain imaging, but that may be also be used to diagnose, stage, and evaluate therapies for migraine [Aron D Mosnaim, Javier Puente and Marion E Wolf. Biological correlates of migraine and cluster headaches: an overview of their potential use in diagnosis and treatment. Pragmatic and Observational Research 1(2010): 25-32].

The diagnosis and treatment of migraine is complicated by the potential co-morbidity of migraine with other disorders. Those disorders include ischemic stroke and transient ischemic attack (TIA), sub-clinical cerebral lesions, coronary heart disease, patent foramen ovale, depression, generalized anxiety disorder, panic disorder, bipolar disorders, restless leg syndrome, obesity, epilepsy (co-morbid with aura), fibromyalgia, irritable bowel syndrome, and celiac disease. Additional disorders that may be co-morbid with migraine comprise allergic rhinitis, sinusitis, and asthma, the co-morbidity of which is largely responsible for the considerable underreporting and misdiagnosis of migraine [H. C. DIENER, M. Küper, and T. Kurth. Migraine-associated risks and co-morbidity. J Neurol (2008) 255:1290-1301; Shuu-Jiun WANG, Ping-Kun Chen and Jong-Ling Fuh. Co-morbidities of migraine. Frontiers in Neurology 1 (Article 16, 2010): pp. 1-9. doi: 10.3389/fneur.2010.00016; Marcelo E. BIGAL, Richard B. Lipton, Philip R. Holland, Peter J. Goadsby. Obesity, migraine, and chronic migraine. Possible mechanisms of interaction. Neurology 68 (2007): 1851-1861].

A migraine headache typically passes through the following stages: prodrome, aura, headache pain, and postdrome. All these phases do not necessarily occur, and there is not necessarily a distinct onset or end of each stage, with the possible exception of the aura. An interictal period follows the postdrome, unless the postdrome of one migraine attack overlaps the prodrome of the next migraine attack.

The prodrome stage comprises triggering events followed by premonitory symptoms. Triggers (also called precipitating factors) usually precede the attack by less than 48 h. The most commonly reported triggers are: stress and negative emotions; hormonal factors for females (menstruation, menopause, pregnancy, use of oral contraceptives, and hormone replacement therapy); flicker, glare and eyestrain; noise; odors (exhaust fumes, cleaning solutions, perfume); hunger and thirst (skipped meals, delayed meals, fasting, dehydration, withdrawal of reactive foods and drinks, particularly caffeinated); consumption of certain foods (e.g., chocolate, monosodium glutamate, pungent foods) and alcohol; weather (cold, heat, high humidity, sudden changes in weather, allergens such as pollen); fatigue; and lack of sleep or too much sleep [Burstein R, Jakubowski M. A unitary hypothesis for multiple triggers of the pain and strain of migraine. J Comp Neurol 493(2005):9-14; Vincent T. Martin, Michael M. Behbehani. Towards a rational understanding of migraine trigger factors. Medical Clinics of North America 85(4, 2001): 911-41].

The prodrome is often characterized by fatigue, sleepiness, elation, food cravings, depression, irritability, among other symptoms. Clinical signs of sensory hyper-excitability often make their debut during the premonitory phase, which later accompany the headache phase, such as photo/phonophobia, hyperosmia and cutaneous allodynia of the scalp. Patients may also describe nausea during the prodrome. The average duration of the prodrome is 6 to 10 hours, but in half of migraine attacks, the prodrome is less than two hours (or absent), and in approximately 15% of migraine attacks, the prodrome lasts for 12 hours to 2 days. The following symptoms were found to be most predictive of imminent headache pain: difficulty with speech, reading or writing, and yawning. Many prodromal symptoms persist after the headache (during the postdrome), but the following decrease significantly: yawning, blurred vision, and nausea/vomiting [Leslie KELMAN. The premonitory symptoms (prodrome): a tertiary care study of 893 migraineurs. Headache 44(2004): 865-872; N. J. Giffin, L. Ruggiero, R. B. Lipton, S. D. Silberstein, J. F. Tvedskov, J. Olesen, J. Altman, P. J. Goadsby, and A. Macrae. Premonitory symptoms in migraine. An electronic diary study. Neurology 60 (2003): 935-940].

It is widely agreed that the aura, which is present in 20-30% of migraine attacks, is due to cortical spreading depression (CSD) within the brain, as now described. An electrophysiological wave is usually initiated within the occipital region of the brain where visual processing occurs, and the wave propagates at a rate of approximately 3 mm/min through neighboring cortical tissue, which is perceived as a scintillating scotoma (zig-zag line) that moves within the visual field as the CSD propagates. Such an aura may be initiated, for example, by viewing a bright light (e.g., reflection of the sun) while the occipital region is in a hypersensitive state. More generally, CSD is triggered when a minimum critical volume of brain tissue is simultaneously depolarized by an intense stimulus, such as concentrated KCl application, direct electrical stimulation, trauma, ischemia or epileptic activity. However, aura symptoms, regardless of their form, vary to a great extent in duration and severity from patient to patient, and also within the same individual. This variation may be due to unique paths that the CSD wave follows in individual attacks as it propagates through regions of the brain that have different functions (e.g., related to speech, memory, motor functions). Furthermore, non-visual and possibly non-perceived (silent) auras may also arise when the CSD is not initiated in the occipital portion of the brain [C. AYATA. Spreading depression: from serendipity to targeted therapy in migraine prophylaxis. Cephalalgia 29 (2009), 1097-1114; Markus A. DAHLEM, Felix M. Schneider, and Eckehard Scholl. Failure of feedback as a putative common mechanism of spreading depolarizations in migraine and stroke. Chaos 18(2, 2008): 026110, pp. 1-11; M B VINCENT and N Hadjikhani. Migraine aura and related phenomena: beyond scotomata and scintillations. Cephalagia 27 (12, 2007):1368-77].

Although the headache phase can begin at any hour, it most commonly begins as mild pain when the patient awakens in the morning. It then gradually builds at variable rates to reach a peak at which the pain is usually described as moderate to severe. The typical headache is unilateral and throbbing, aggravated by movement, with all stimuli tending to accentuate the headache. Patients frequently develop cutaneous allodynia, and sensory hypersensitivity results in patients seeking a dark, quiet place. Blurry vision, nasal stuffiness, anorexia, hunger, diarrhea, abdominal cramps, polyuria, facial pallor, sensations of heat or cold, and sweating might also occur. Depression, fatigue, anxiety, nervousness, irritability, and impairment of concentration are common. The pain phase lasts 4-72 h in adults and 1-72 h in children, with a mean duration generally of less than 1 day. The pain intensity usually follows a smooth curve with a crescendo with a diminuendo.

After the headache has resolved, many patients are left with a postdrome that lingers for one to two days. The main complaints are cognitive difficulties, such as mental tiredness. Patients also describe symptoms of neural hyperexcitability, such as photophobia and allodynia.

The following is known about the pathophysiology of migraine. The trigeminovascular system consists of the neurons innervating the cerebral vessels whose cell bodies are located in a trigeminal ganglion [Arne MAY and Peter J Goadsby. The Trigeminovascular System in Humans: Pathophysiologic Implications for Primary Headache Syndromes of the Neural Influences on the Cerebral Circulation. Journal of Cerebral Blood Flow and Metabolism 19(1999): 115-127]. It is widely accepted that migraine is a neurovascular disorder, wherein the intracranial throbbing pain of migraine is mediated by the interaction between nerves and blood vessels, involving neuronal activity and inflammation along the trigeminovascular pathway [Daniela PIETROBON and Jörg Striessnig. Neurobiology of migraine. Nature Reviews Neuroscience 4 (2003): 386-398; Stephen D SILBERSTEIN. Migraine. LANCET 363 (2004):381-391; M. LINDE. Migraine: a review and future directions for treatment. Acta Neurol Scand 114(2006): 71-83; Egilius L. H. SPIERLINGS. Mechanism of migraine and action of antimigraine medications. Medical Clinics of North America 85 (4, 2001): 943-958; Peter J. GOADSBY, Richard B. Lipton, Michel D. Ferrari. Migraine—Current understanding and treatment. N Engl J Med 346 (4, 2002): 257-270; Peter J. GOADSBY. Migraine pathophysiology. Headache 45[Suppl 1, 2005]:S14-S24; R J HARGREAVES and S L Shepheard. Pathophysiology of Migraine—New Insights. Can. J. Neurol. Sci. 26 (Suppl. 3, 1999): S12-S19; Daniela PIETROBON. Migraine: New molecular mechanisms. Neuroscientist 11(4, 2005): 373-386; Curtis P. SCHREIBER. The pathophysiology of primary headache. Prim Care Clin Office Pract 31 (2004) 261-276; Carlos M. VILLALON, David Centurión, Luis Felipe Valdivia, Peter de Vries and Pramod R. Saxena. Migraine: Pathophysiology, Pharmacology, Treatment and Future Trends. Current Vascular Pharmacology 1 (2003): 71-84; GOADSBY P J, Charbit A R, Andreou A P, et al. Neurobiology of migraine. Neuroscience 2009; 161:327-341; Till SPRENGER and Peter J Goadsby. Migraine pathogenesis and state of pharmacological treatment options. BMC Medicine 7(2009):71, doi:10.1186/1741-7015-7-71, pp 1-5].

Figure 8:
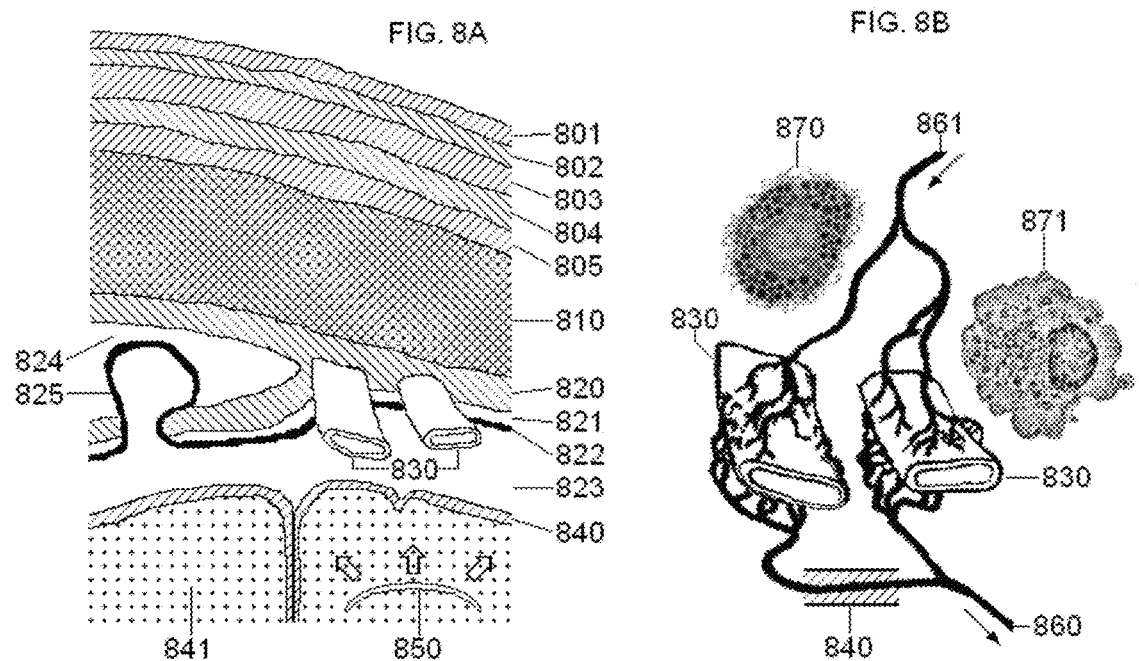
FIGS. 8A-8B illustrate meningeal blood vessels, nerves, and other structures that are involved in the pathophysiology of migraine headaches, some of which may be affected by stimulation of the vagus nerve according to the present invention.

The cranial blood vessels are illustrated in FIG. 8. As seen in FIG. 8A, the cranial vessels (arteries and veins) 830 lie between the skullcap bone 810 and grey matter of the cerebral hemispheres 841, within the meninges that comprises the dura mater 820, the arachnoid mater 822 and the pia mater 840. Other structures shown in FIG. 8A include skin 801, connective tissue 802, aponeurosis 803, loose areolar tissue 804, pericranium 805, subdural space 821, subarachnoid space 823, superior sagittal sinus 824, and an arachnoid granulation 825. The cranial vessels 830 are shown here within the dura mater 820. However, it is understood in what follows that the relevant noiceceptive nerve fibers may be located not only around the large cranial vessels, but also around pial vessels, sinuses such as the superior sagittal sinus 824, and dura mater 820.

The trigeminal ganglion is a sensory ganglion of the trigeminal nerve. The trigeminal nerve (V cranial nerve) consists of three main branches, the ophthalmic (V1), maxillary (V2), and mandibular (V3), each providing somatosensory innervations of distinct regions of the head, face, and orofacial cavity. Although the migraine headache pain arises primarily from activation of the opthalmic branch (V1), all branches of the trigeminal nerve share the same basic pathophysiology. For many individuals the first symptom of altered trigeminal function with subsequent inflammatory protein release may be at the maxillary (V2) or even mandibular (V3) trigeminal divisions. This is important clinically because some patients may experience the first symptoms in the region innervated by V2, namely, the area of the nasal passages, and they may be misdiagnosed (through the patient's own self diagnosis or clinician's diagnosis) with sinus headache. However, a trigeminally mediated neuroinflammatory response at the level of the nasal passages can explain the nasal congestion, discharge, and discomfort experienced by many patients at the onset of their migraine attacks. Similarly, pericranial (jaw and neck) muscle tenderness is a common symptom in migraine, which might be attributed in part to activation of the mandibular (V3) trigeminal division.

As shown in FIG. 8B, the development of headache depends on the activation of nociceptive afferent fibers 860 of trigeminal ganglion neurons innervating the blood vessels 830 in the meninges. Activation of the trigeminovascular afferents 860 by a variety of mechanisms leads to the release of vasoactive neuropeptides in the meninges. These trigeminal fibers contain substance P (SP) and calcitonin gene-related peptide (CGRP), both of which can be released when the fibers are stimulated. Neurokinin A (formerly known as substance K), produced from the same gene as substance P, may also be released. Trigeminal ganglion fiber stimulation also increases cerebral blood flow through release of a powerful vasodilator peptide, vasoactive intestinal polypeptide (VIP). Vasodilation of meningeal blood vessels also occurs via activation of parasympathetic efferents 861, wherein nitric oxide (NO) and acetylcholine (ACh) are released. The dilation also causes mechanical stretching or bending of the perivascular nerve fibers, which results in fiber depolarization, in addition to that attributable to the above-mentioned released chemicals.

Stimulation may also results in leakage of plasma from dural blood vessels (plasma extravasation), leaked components of which may contribute to the nociception. Additional structural changes in the dura mater after trigeminal ganglion stimulation include degranulation of mast cells 870 (not drawn to scale) and activation of macrophages 871 (not drawn to scale). Activation of such resident immune cells, which are prominent components of the intracranial meninges, is also likely to serve as an important step in promoting the enhanced excitability of meningeal nociceptors. Inhibition of neuroinflammation in the vicinity of a nociceptor might therefore be accomplished through the inhibition of pro-inflammatory cytokines and/or histamine or the release of anti-inflammatory cytokines and/or antihistamines.

In addition to the above-mentioned self-reinforcing mechanisms for activation of nociceptive afferent fibers 860 of trigeminal ganglion neurons innervating the blood vessels 830 in the meninges, cortical spreading depression (CSD) that accompanies migraine aura may also activate the fibers. FIG. 8A shows a wave of cortical spreading depression 850 that is propagating (shown with arrows) within the cerebral hemisphere. As seen in FIG. 8B, the wave may eventually reach pia mater 840, activating perivascular trigeminal terminals therein. Such CSD-mediated activation will stimulate nearby nociceptive fibers that impinge upon a blood vessel 830, resulting in the release of substance P, calcitonin gene-related peptide, etc.; and it will also result in a nociceptive afferent signal that is sent to central brain structures via the trigeminal nerve branch.

Figure 9:
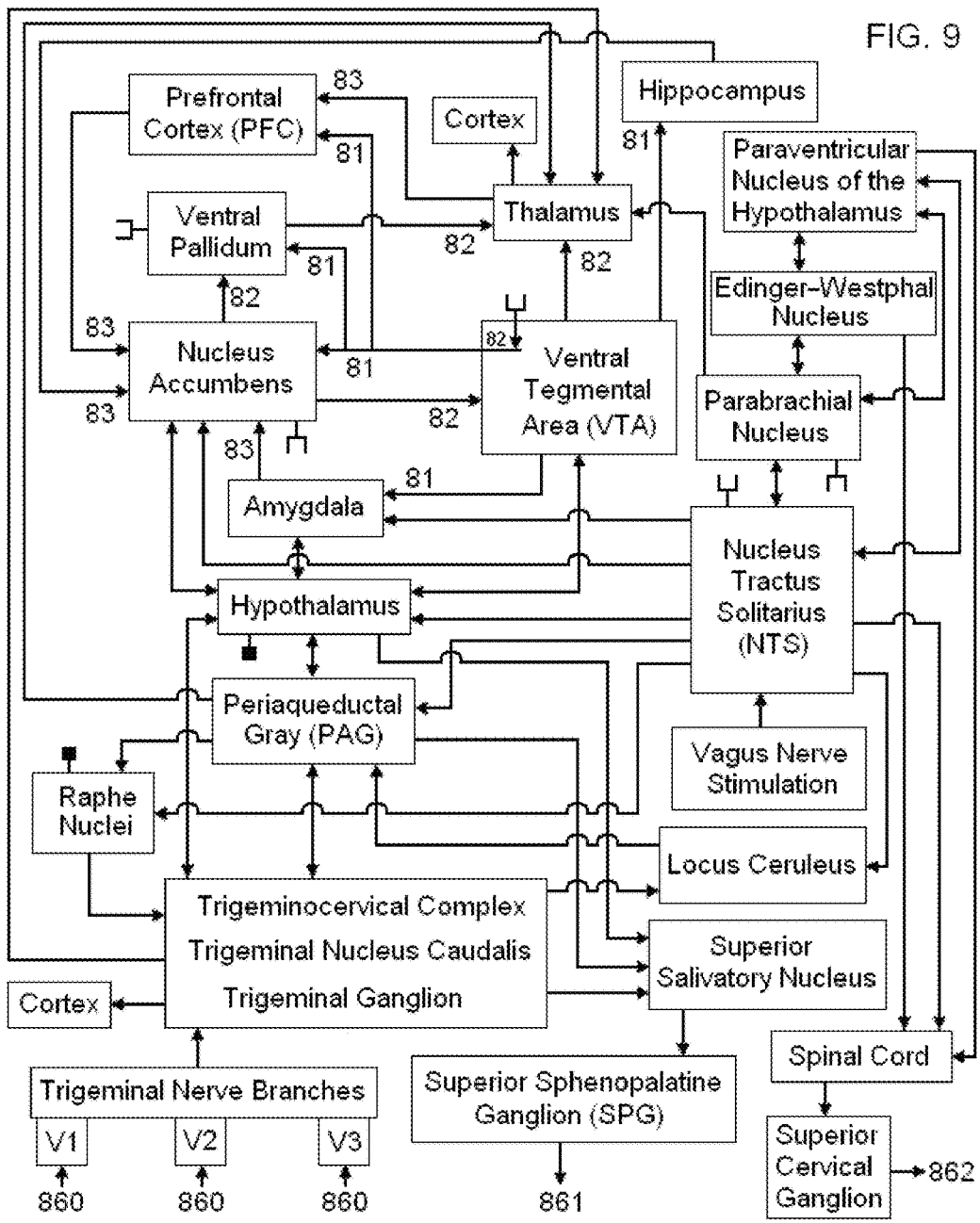
FIG. 9 illustrates neuronal mechanisms or pathways through which stimulation of the vagus nerve may reduce the pain of a migraine headache and/or ameliorate sinus symptoms that resemble an immune-mediated response ("sinus" headaches) and/or treat rhinitis, sinusitis, or rhinosinusitis, irrespective of whether those conditions are co-morbid with a headache.

After meningeal stimulation and/or inflammation, the corresponding afferent signal 860 is relayed to the trigeminal nucleus caudalis (TNC), as shown in FIG. 9. As described above in connection with description of the branches of the trigeminal nerve, the meningeal signal arrives from the ophthalmic branch (V1), but more generally a signal may arrive from the maxillary (V2) and/or mandibular (V3) branches as well, which are also labeled as an afferent signal 860. Stimulation of the superior sagittal sinus (824 in FIG. 8) also causes excitation in the TNC, as well as in the dorsal horn at the C1 and C2 levels. Stimulation of a branch of C2, the greater occipital nerve, increases neuronal activity in the same regions, i.e., the TNC and C1/2 dorsal horn. This group of neurons from the superficial laminae of trigeminal nucleus caudalis and C1/2 dorsal horns is known functionally as the trigeminocervical complex. Thus, a substantial portion of the trigeminovascular nociceptive signals comes through mostly caudal cells. This provides an anatomical explanation for the experience of pain to the back of the head in migraine.

As also shown in FIG. 9, following neuronal transmission in the caudal brain stem and high cervical spinal cord of the trigeminocervical complex, information is relayed to the thalamus, contralateral to the acute migraine pain, which processes and forwards the processed signal to the cerebral cortex, where it is perceived as migraine pain. Stimulating the superior sagittal sinus (824 in FIG. 8) also activates neurons in the ventrolateral periaqueductal gray matter (PAG) and in the dorsal pons, near the locus ceruleus. Notably, electrical stimulation with electrodes in the PAG and locus ceruleus induces migraine-like headaches. The PAG is involved in craniovascular pain not only through ascending projections to the thalamus but also through descending, mostly inhibitory modulation of nociceptive afferent information via projections to serotonergic neurons in the raphe nucleus. Upon activation, the nucleus locus ceruleus, the main central noradrenergic nucleus, reduces cerebral blood flow, apparently by causing vasodilation in other vessels to divert the flow of blood. In contrast, the main serotonin-containing nucleus in the brain stem, the raphe nucleus, increases cerebral blood flow when activated.

As also shown in FIG. 9, a migraine-related pathway involves pre- and postganglionic parasympathetic neurons in the superior salivatory nucleus (SSN) and sphenopalatine ganglion (SPG), respectively. The SSN stimulates the release of acetylcholine, vasopressin intestinal peptide, and nitric oxide from meningeal terminals of SPG neurons, resulting directly or indirectly in the cascade of events that include the dilation of intracranial blood vessels, plasma protein extravasation, and local release of inflammatory molecules that activate adjacent terminals of meningeal nociceptors. This autonomic activation also leads to lacrimation, reddening of the eye, and nasal congestion. The efferent circuit element 861 shown in FIG. 9 is the same as the element so-labeled in FIG. 8B. The SSN receives extensive input from more than fifty brain areas, three of which are shown in FIG. 9. Furthermore, the same hypothalamic, limbic, and cortical areas that project to the SSN also appear to receive extensive afferent connections from the trigeminovascular pathway. This provides a neuroanatomical mechanism by which stimulation of the afferent 860 in FIGS. 8 and 9 can lead to a positive-feedback stimulation of the efferent 861 [BURSTEIN R, Jakubowski M. A unitary hypothesis for multiple triggers of the pain and strain of migraine. J Comp Neurol 2005; 493:9-14].

The foregoing sequence of activation, from meninges inflammation to trigeminal nucleus caudalis to thalamus, PAG, locus ceruleus, raphe nuclei and back via the SSN and SPG does not ascribe a proximal cause of the trigeminal activation, other than possibly the cortical spreading depression that is associated with aura experienced by some migraineurs. This is because the proximal events leading to activation of the trigeminal ganglia fibers may trigger the migraine, but they are not necessarily the cause of the migraine, for the following reason. Once the migraine has started, it becomes self-perpetuating, which is to say, painful stimulation from the ongoing migraine itself may be sufficient to feed back and maintain activation of the trigeminal ganglia, long after the triggering events have passed. In fact, it is conceivable that internal random or chaotic fluctuations of neuronal activity within the trigeminal ganglia itself, and the structures with which it is physiologically connected, may be sufficiently amplified by positive feedback of the system to trigger the migraine, without even the need for an external triggering event. For this reason, the pathophysiology of migraine triggers is important not so much as it relates to the initial events of the migraine attack, but rather as it relates to the origins of the hypersensitivity of the trigeminovascular and other neurological systems in migraineurs.

Hypersensitivity in migraine headaches, as well as the common migraine prodromal symptoms, may result from connection of the trigeminovascular pathway with an abnormal hypothalamus and/or limbic system, which in turn may be associated with imbalanced neurotransmitter levels. Such connections are shown in FIG. 9, many of which involve the hypothalamus, which is activated during a migraine attack [Marie Denuelle, Nelly Fabre, Pierre Payoux, Francois Chollet, Gilles Geraud. Hypothalamic Activation in Spontaneous Migraine Attacks. Headache 47 (2007):1418-1426]. Many migraine patients experience premonitory autonomic and endocrine symptoms (sleep disturbances, changes of wakefulness and alertness, as well as changes of appetite and thirst) that may well be attributed to primary hypothalamic dysfunction. In particular, the association of migraine with hormonal changes and the fact that migraine occurs most often in women may be attributed to involvement of the hypothalamus. The hypothalamus may also regulate activity of the thalamus, periaqueductal gray, locus ceruleus, trigeminocervical complex, and cortical structures via its secretion of orexin. Furthermore, the hypothalamus plays an important role in control of nociception, for example, involving the release of endogenous opioid peptides, as described below [K B Alstadhaug. Migraine and the hypothalamus. Cephalalgia 29(2009): 809-817].

Connections of the trigeminovascular pathway to the limbic system via the hypothalamus may also explain in part the hypersensitivity that is associated with migraine headaches. The extended amygdala with its connections within the limbic system mediates long-lasting responses during sustained stress, which is the prodromal symptom most commonly associated with migraine. Such responses persist long after the termination of stress, so migraine nociception may be enhanced as a consequence of the connection of the trigeminovascular pathway to an activated limbic system.

Hyperactivity of cranial parasympathetic nerves was mentioned above in connection with the superior salivatory nucleus and superior sphenopalatinate ganglion. Thus, parasympathetic symptoms such as facial flushing, lacrimation and nasal stuffiness may accompany migraine attacks. In contrast, sympathetic hypofunction appears to be associated with migraine. Even during headache-free periods, migraineurs have reduced sympathetic function, as compared with non-migraineurs. This is evidenced in migrainers by reduced norepinephrine levels, adrenergic receptor supersensitivity, orthostatic intolerance, decreased Valsalva maneuver response, impaired isometric exercise and cold-pressor responses and impaired pupillary control. These observations are consistent with the view that prolonged stimulation of the sympathetic nervous system in migraineurs has depleted norepinephrine levels. This leads to an increase in the release of other sympathetic neurotransmitters, particularly dopamine, adenosine, neuropeptide Y, dynorphin, and prostaglandins. Nausea/vomiting and yawning are symptoms that are associated with increased dopamine levels. Increased pain sensitivity and inflammation are symptoms that are associated with increased prostaglandin levels. Drowsiness is a symptom that is associated with increased adenosine levels. Also, the decreased norepinephrine levels will result in orthostatic intolerance and vasodilation. Furthermore, because the sympathetic system normally acts to inhibit the trigeminal system, hypofunction of the sympathetic nervous system will promote migraine attacks. The sympathetic nervous system works in conjunction with the hypothalamus and limbic system as part of the physiological stress response system. Then, according to this view, a prime cause of migraine would be prolonged stress and its sequela in a susceptible individual, which is consistent with the fact that stress is cited as the primary trigger of migraine attacks. The anticipation of migraine, as well as the actual migraine attacks, will contribute to that stress [Stephen J. Peroutka. Migraine: a chronic sympathetic nervous system disorder. Headache 44(2004): 53-64].

In addition to its role in producing prodromal symptoms such as yawning, dopamine that is produced in the hypothalamus and elsewhere may also act directly on trigeminal afferents to modulate (generally inhibit) the trigeminocervical complex [Annabelle R. CHARBIT, Simon Akerman and Peter J. Goadsby. Dopamine: what's new in migraine? Current Opinion in Neurology 23 (2010):275-281]. Another neurotransmitter that is implicated in migraine is serotonin (5-HT), wherein a low 5-HT state facilitates activation of the trigeminovascular nociceptive pathway when induced by cortical spreading depression [E. HAMEL. Serotonin and migraine: biology and clinical implications. Cephalalgia 27 (2007): 1295-1300].

Current treatments for migraine are made in the context of its above-described pathophysiology, but are often based on trial and error. Pharmacological treatments may be divided into those that are intended to prevent migraine attacks and those administered during an attack. Current preventive treatment includes the administration of one or more of the following: beta-blockers (Propranolol, Metoprolol), anti-convulsants (Valproate, Topiramate, Gabapentin, lamotrigine), antidepressants (Amitriptyline, dosulepin, nortriptyline, Venlafaxine), calcium-channel blockers (Flunarizine, Verapamil), serotonin antagonists (Pizotifen, Methysergide), and dietary supplements (Riboflavin, Coenzyme Q10). Drugs that are administered during a migraine attack fall into two categories: analgesics and nonsteroidal anti-inflammatory drugs (NSAIDS) that are not specific for migraine; and largely migraine-specific drugs (ergot-related compounds and triptans). The former group of drugs include: aspirin, paracetamol, Naproxen and ibuprofen. To counter nausea during the migraine attack, anti-emetics are often administered as well (domperidone, metoclopramide). Migraine-specific drugs are administered when the non-specific drugs are ineffective. They include ergot-related Dihydroergotamine as a nasal spray or injection, and triptans, which are serotonin 5-HT1B/1D receptor agonists: Sumatriptan, Zolmitriptan, Naratriptan, Rizatriptan, Eletriptan, Almotriptan, and Frovatriptan. Often a different triptan will be administered if the currently administered triptan is ineffective for three migraine attacks. Triptans have cardiovascular side effects and are contraindicated during pregnancy and when a selective serotonin reuptake inhibitor (SSRI) is being administered. Furthermore, only 30-40% of migraineurs are pain-free two hours after the administration of triptans. Of those who do respond, one in three will experience a migraine recurrence within 24 hours.

In situations in which the above-mentioned standard drug treatments are ineffective, the following experimental drug treatments have been tried: Botulinum Toxin Type A for prophylaxis (possibly blocking the local release of glutamate and substance P) and divalproex sodium, which increases the levels of inhibitory neurotransmitter gamma-aminobutyric acid (GABA). Additional drugs are under trial, notably CGRP1 antagonists, glutamate receptor antagonists, transient receptor potential vanilloid (TRPV1) receptor antagonists, nitric oxide synthesis inhibitors, and prostanoid receptor antagonists [Peter J Goadsby, Till Sprenger. Current practice and future directions in the prevention and acute management of migraine. Lancet Neurol 9 (2010): 285-98; Elizabeth W. Loder, Steven B. Graff-Radford, Timothy R. Smith. Migraine treatment strategies. The rationale for early intervention. 2003 National Headache Foundation 820 N. Orleans, Suite 217, Chicago, Ill. 60610-3132; Stephen D. Silberstein. Preventive treatment of migraine. TRENDS in Pharmacological Sciences 27 (8, 2006): 410-415; Teshamae S. Monteith and Peter J. Goadsby. Acute Migraine Therapy: New drugs and new approaches. Current Treatment Options in Neurology 13(2011):1-14].

Non-pharmacological treatments of migraine headaches have a long history [Peter J. KOEHLER and Christopher J. Boes. A history of non-drug treatment in headache, particularly migraine. Brain 133(2010): 2489-2500]. Behavioral therapy is sometimes used when the patient has overused drugs [Grazzi L, Andrasik F, D'Amico D, et al. Behavioral and pharmacologic treatment of transformed migraine with analgesic overuse: outcome at 3 years. Headache 42 (2002): 483-90]. Non-invasive physical treatments for migraine include spinal manipulation, mobilization, massage, therapeutic touch, therapeutic exercise, cold packs, and electrical modalities (including pulsating electromagnetic fields [PEMF], cranial electrotherapy, interferential therapy, transcutaneous electrical nerve stimulation [TENS], and ultrasound), and different combinations of physical treatments [Brønfort G, Nilsson N, Haas M, Evans R L, Goldsmith C H, Assendelft W J J, Bouter L M. Non-invasive physical treatments for chronic/recurrent headache. Cochrane Database of Systematic Reviews 2004 (update 2009), Issue 3. Art. No.: CD001878. DOI: 10.1002/14651858.CD001878.pub2]. Another noninvasive physical treatment for migraine is phototherapy [D. J. Anderson. The Treatment of Migraine with Variable Frequency Photo-Stimulation. Headache 29(1989):154-155; David Noton. Migraine and photic stimulation: report on a survey of migraineurs using flickering light therapy. Complementary Therapies in Nursing and Midwifery 6(2000): 138-142].

Acupuncture has slightly better outcomes and fewer adverse effects than prophylactic drug treatment for migraine [M. Romoli, G. Allais, G. Airola, C. Benedetto. Ear acupuncture in the control of migraine pain: selecting the right acupoints by the "needle-contact test". Neurol Sci 26(2005):5158-5161; Gianni Allais, Marco Romoli, Sara Rolando, Ilaria Castagnoli Gabellari, Chiara Benedetto. Ear acupuncture in unilateral migraine pain. Neurol Sci 31 (Suppl 1, 2010):5185-5187; Linde K, Allais G, Brinkhaus B, Manheimer E, Vickers A, White A R. Acupuncture for migraine prophylaxis. Cochrane Database of Systematic Reviews 2009, Issue 1. Art. No.: CD001218. DOI: 10.1002/14651858.CD001218.pub2].

Greater occipital nerve blockade and trigger point injections have also been used to treat migraine [Maria Gabriella SARACCO, W. Valfre, M. Cavallini, M. Aguggia. Greater occipital nerve block in chronic migraine. Neurol Sci 31 (Suppl 1, 2010):5179-5180; Bert B. Vargas, David W. Dodick. The Face of Chronic Migraine: Epidemiology, Demographics, and Treatment Strategies. Neurol Clin 27 (2009) 467-479; Ashkenazi A, Matro R, Shaw J W, et al. Greater occipital nerve block using local anesthetics alone or with triamcinolone for transformed migraine: a randomized comparative study. J Neurol Neurosurg Psychiatr 79(2008):415-7].

Electrical stimulation with implanted electrodes has also been tried, in lieu of occipital or auriculotemporal nerve blockade [Charles A. Popeney, Kenneth M. Aló. Peripheral Neurostimulation for the Treatment of Chronic, Disabling Transformed Migraine. Headache 43(2003):369-375; Thomas Simopoulos, Zahid Bajwa, George Lantz, Steve Lee, Rami Burstein. Implanted Auriculotemporal Nerve Stimulator for the Treatment of Refractory Chronic Migraine. Headache 50(6, 2010):1064-1069; U.S. Pat. No. 6,735,475, entitled Fully implantable miniature neurostimulator for stimulation as a therapy for headache and/or facial pain, to Whitehurst et al.].

Surgical treatment of those nerves may also be undertaken, although surgery has the disadvantage of irreversibility [Ivica Ducic, Emily C. Hartmann, Ethan E. Larson. Indications and Outcomes for Surgical Treatment of Patients with Chronic Migraine Headaches Caused by Occipital Neuralgia. Plast. Reconstr. Surg. 123(2009): 1453-1461; Jeffrey E. Janis, Daniel A. Hatef, Ivica Ducic, Jamil Ahmad, Corinne Wong, Ronald E. Hoxworth, Timothy Osborn. Anatomy of the Auriculotemporal Nerve: Variations in Its Relationship to the Superficial Temporal Artery and Implications for the Treatment of Migraine Headaches. Plast. Reconstr. Surg. 125(2010): 1422-1428].

In addition, magnetic stimulation just below the occipital bone has been used to treat migraine [Richard B Lipton, David W Dodick, Stephen D Silberstein, Joel R Saper, Sheena K Aurora, Starr H Pearlman, Robert E Fischell, Patricia L Ruppel, Peter J Goadsby. Single-pulse transcranial magnetic stimulation for acute treatment of migraine with aura: a randomized, double-blind, parallel-group, sham-controlled trial. Lancet Neurol 9(2010): 373-80; Thorsten Bartsch, Koen Paemeleire and Peter J. Goadsby. Neurostimulation approaches to primary headache disorders. Current Opinion in Neurology 22(2009):262-268; Peter J Goadsby, Till Sprenger. Current practice and future directions in the prevention and acute management of migraine. Lancet Neurol 9(2010): 285-98].

Finally, vagal nerve stimulation (VNS) has been used to treat migraine headaches. However, only invasive VNS has been reported; the VNS has not been reported to treat nasal congestion or other features resembling a "sinus" headache; and the parameters of stimulation are different than the parameters disclosed herein [R M SADLER, R A Purdy & S Rahey. Vagal nerve stimulation aborts migraine in patient with intractable epilepsy. Cephalalgia 22(2002), 482-484; E. Daniela HORD, M. Steven Evans, Sajjad Mueed, Bola Adamolekun, and Dean K. Naritoku. The Effect of Vagus Nerve Stimulation on Migraines. The Journal of Pain 4 (9, 2003): 530-534; Duncan A. GROVES, Verity J. Brown. Vagal nerve stimulation: a review of its applications and potential mechanisms that mediate its clinical effects. Neuroscience and Biobehavioral Reviews 29 (2005) 493-500; A MAUSKOP. Vagus nerve stimulation relieves chronic refractory migraine and cluster headaches. Cephalalgia 25(2005):82-86; M E LENAERTS, K J Oommen, J R Couch & V Skaggs. Can vagus nerve stimulation help migraine? Cephalalgia 28(2008), 392-395; Alberto Proietti CECCHINI, Eliana Mea and Vincenzo Tullo, Marcella Curone, Angelo Franzini, Giovanni Broggi, Mario Savino, Gennaro Bussone, Massimo Leone. Vagus nerve stimulation in drug-resistant daily chronic migraine with depression: preliminary data. Neurol Sci 30 (Suppl 1, 2009):S101-S104; A. MAY and T. P. Jürgens. Therapeutic neuromodulation in primary headache syndromes (Therapeutische Neuromodulation bei primären Kopfschmerzsyndromen). Nervenarzt 2010: doi_10.1007/s00115-010-3170-x; Patent application US20050216070, entitled Method and system for providing therapy for migraine/chronic headache by providing electrical pulses to vagus nerve(s), to Boveja et al.]. U.S. Pat. No. 4,537,195, entitled Electrical control of body discharges and headaches, to McDonnell discloses transcutaneous electrical stimulation to treat migraine headaches by applying one electrode to the arm and a second electrode to the neck, but does not disclose stimulation of the vagus nerve. U.S. Pat. No. 5,215,086, entitled Therapeutic treatment of migraine symptoms by stimulation, to Terry (Jr.) et al.; U.S. Pat. No. 6,735,475, entitled Fully implantable miniature neurostimulator for stimulation as a therapy for headache and/or facial pain, to Whitehurst et al.; and U.S. Pat. No. 7,769,461, entitled Skull-mounted electrical stimulation system and method for treating patients, to Whitehurst et al. disclose electrical stimulation to treat migraine headaches but they are not concerned with non-invasive stimulation.

When all the above methods of treating migraine fail, rescue treatment involves the administration of opioids, which has as its primary side effect the possibility of addiction. Accordingly, the use of opiates is generally restricted to patients who are unresponsive to many different migraine-specific therapies and who require frequent emergency room visits to abort their migraine attacks. However, even daily opioids may fail to provide sustained relief [Joel R. SAPER, Alvin E. Lake III, Philip A. Bain, Mark J. Stillman, John F. Rothrock, Ninan T. Mathew, Robert L. Hamel, Maureen Moriarty, Gretchen E. Tietjen. A Practice Guide for Continuous Opioid Therapy for Refractory Daily Headache: Patient Selection, Physician Requirements, and Treatment Monitoring. Headache 50(2010): 1175-1193].

It is possible to use drugs other than narcotics in an attempt to dissociate the neural pathways associated with pain production from pathways involving the perception of pain. One such drug is ketamine, which is very commonly used as a dissociative anesthetic, especially in veterinary medicine. At certain doses, ketamine produces euphoria and is therefore consumed by drug abusers. When used to treat depression, ketamine produces effects much more quickly than conventional antidepressant medication [Nancy A. Melville. Bolus Dose of Ketamine Offers Fast-Acting Alleviation of Acute Depression in ED Setting. Medscape Medical News (2010): Article 729622; Carlos A. Zarate, Jaskaran B. Singh, Paul J. Carlson, Nancy E. Brutsche, Rezvan Ameli, David A. Luckenbaugh, Dennis S. Charney, Husseini K. Manji. A Randomized Trial of an N-methyl-D-aspartate Antagonist in Treatment-Resistant Major Depression. Arch Gen Psychiatry. 2006; 63:856-864].

As described below, ketamine is also effective in the treatment of migraine headaches. The speed with which ketamine produces its effects, as well as the nature of those effects, are similar to those produced by Applicant's disclosed vagal nerve stimulation (VNS) methods, as described also in commonly assigned co-pending patent application Ser. No. 13/024,727, entitled "Non-invasive methods and devices for inducing euphoria in a patient and their therapeutic application," which is hereby incorporated by reference. The neuronal mechanisms underlying the effects of ketamine and the disclosed VNS methods appear to be similar, which leads to the present invention that uses the disclosed VNS stimulation to treat migraine. Because the disclosed VNS method has no known side-effects, it may be more suitable than the use of ketamine and related compounds to treat migraine.

Ketamine is a glutamate receptor antagonist. NICOLODI et al. claim that ketamine (as well as the NMDA receptor antagonist gapapentin) can cure chronic migraine by causing it to revert to episodic migraine [NICOLODI M, Sicuteri F. Negative modulators of excitatory amino acids in episodic and chronic migraine: preventing and reverting chronic migraine. Special lecture 7th INWIN Congress. Int J Clin Pharmacol Res. 18(2, 1998): 93-100]. Evidence has also been presented that ketamine can stop migraine aura, at least in patients with familial hemiplegic migraine [KAUBE H, Herzog J, Käufer T, Dichgans M, Diener H C. Aura in some patients with familial hemiplegic migraine can be stopped by intranasal ketamine. Neurology 55(1, 2000): 139-41]. Several other glutamate receptor antagonist drugs are under active development for the treatment of migraine [MONTEITH T S, Goadsby P J. Acute migraine therapy: new drugs and new approaches. Curr Treat Options Neurol. 2011 (1, 2011):1-14]. Some of the mechanisms by which glutamate receptor agonists inhibit migraine headaches involve the colocalization of glutamate with 5-HT(1B/1D/1F) receptors in trigeminal ganglia, as well as the effects of glutamate receptor agonists on the diameter of arteries that are involved in migraine pain [MA QP. Co-localization of 5-HT(1B/1D/1F) receptors and glutamate in trigeminal ganglia in rats. Neuroreport 12(8, 2001):1589-1591; CHAN K Y, Gupta S, de Vries R, Danser A H, Villalón C M, Muñoz-Islas E, Maassenvandenbrink A. Effects of ionotropic glutamate receptor antagonists on rat dural artery diameter in an intravital microscopy model. Br J Pharmacol. 160 (6, 2010):1316-25]. Furthermore, inherited forms of migraine susceptibility involve a sequence variant on chromosome 8q22.1, which is flanked by two genes involved in glutamate homeostasis, leading to the view that disruption of glutamate metabolism is a primary cause of migraine, and that treatment of migraine should address that cause.

In a preferred embodiment of the invention, glutamate receptor antagonist effects, brought about by nerve stimulation, comprise the following. The glutamate receptor, which is ordinarily found on the surface of a post-synaptic cell, has an ion channel that only opens when the following two conditions are met simultaneously: glutamate is bound to the receptor, and the postsynaptic cell is depolarized (which removes $Mg^{2+}$ blocking the channel). To antagonize glutamate receptors, a stimulated nerve may (1) block/inhibit the synthesis or release of the neurotransmitter glutamate from a pre-synaptic cell; (2) maintain a post-synaptic cell in a hyperpolarized state; (3) directly or indirectly modulate activity of the receptor via control of endogenous modulators such as glutathione, lipoic acid, H+, K+, and 5-HT1B/1D/1F receptors; and (4) a combination of these effects. The invention contemplates that different glutamate receptors (N-methyl-D-aspartate (NMDA), a-amino-3-hydroxy-5-methyl-4-isoazolepropionic acid (AMPA) and kainate) may be modulated by such nerve stimulation.

Pathways relating Applicant's vagal nerve stimulation method to its observed effects in migraineurs, including rapid dissociation of the perception of pain from the production of pain (relief within seconds to minutes through a euphoria-like mechanism) are shown in FIG. 9. Pathways relating to the relief of sinus congestion and related symptoms, involving for example direct or indirect inhibition of the superior salivatory nucleus parasympathetic pathway, are also shown. It is understood that the pathways shown there are a simplification of the actual mechanisms, that not all of the pathways may participate equally, that pathways not shown may also participate, and that future investigations may require that the pathways be modified. The arrows indicate the direction of information flow, some of which are bi-directional.

Beginning in the right middle right side of FIG. 9, the vagus nerve is stimulated, and the resulting signal is sent towards the brain. Vagal afferents traverse the brainstem in the solitary tract, with some eighty percent of the terminating synapses being located in the nucleus of the tractus solitarius (NTS). The NTS projects to a wide variety of structures, as shown in FIG. 9, including the amygdala, the nucleus accumbens, and the hypothalamus [JEAN A. The nucleus tractus solitarius: neuroanatomic, neurochemical and functional aspects. Arch Int Physiol Biochim Biophys 1991; 99(5):A3-A52]. The NTS also projects to the parabrachial nucleus, which in turn projects to the hypothalamus, the thalamus, the amygdala, the anterior insular, and infralimbic cortex, lateral prefrontal cortex, and other cortical regions. The thalamus projection shown in FIG. 9 is one from which the perception of pain may reach the cortex. Other pathways from the NTS to many of the other structures shown in FIG. 9 are multi-synaptic [M. CASTLE, E. Comoli and A. D. Loewy. Autonomic brainstem nuclei are linked to the hippocampus. Neuroscience 134 (2005) 657-669]. Through its direct or indirect projection to the amygdala and the nucleus accumbens, the NTS gains access to amygdala-hippocampus-entorhinal cortex pathways of the limbic system. The disclosed method of vagal nerve stimulation uses parameters (intensity, pulse-width, frequency, duty cycle, etc.) that activate the limbic system via the amygdala and nucleus accumbens or other routes [Jeong-Ho CHAE, Ziad Nahas, Mikhail Lomarev, Stewart Denslow, Jeffrey P. Lorberbaum, Daryl E. Bohning, Mark S. George. A review of functional neuroimaging studies of vagus nerve stimulation (VNS). Journal of Psychiatric Research 37 (2003) 443-455; G. C. Albert, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060].

In its most basic conception, the limbic system can be defined by its input from dopaminergic neurons originating in the ventral tegmental area (VTA) of the brain. Those dopamine-producing neurons are shown in FIG. 9 as 81, projecting to the nucleus accumbens, with neurons branching nearby that project to the ventral palladium (VP) and prefrontal cortex (PFC). In addition, dopamine-producing neurons 81 project from the VTA to the amygdala and to the hippocampus. The feeling of relief that may be felt by an individual is thought to occur when the VTA floods these dopaminergic neurons 81 with dopamine, thereby stimulating the nucleus accumbens, VP, PFC, amygdala, and hippocampus.

Feedback from the above-mentioned structures to the VTA determines the magnitude of the dopamine levels, as well as the steady state that obtained before the stimulation. The feedback loops involve neurons that use gamma-aminobutyric acid (GABA) as their neurotransmitter 82 as well as neurons that use glutamate as their neurotransmitter 83. The GABAminergic neurotransmission is generally inhibitory, while the glutamatergic neurotransmission is generally excitatory. As shown in FIG. 9, glutmatergic neurotransmission 83 occurs from the amygdala, PFC and hippocampus to the nucleus accumbens, as well as from the thalamus to the PFC. As also shown in FIG. 9, GABAminergic neurotransmission 82 occurs from the VTA and VP to the thalamus, from the nucleus accumbens to the VTA and VP, as well as within the VTA, which has the effect of inhibiting dopamine neurotransmission. The mechanism of inhibition is that a GABA-A receptor on the dopaminergic neuron binds to GABA released from a GABAminergic neuron, which inhibits dopaminergic neurotransmission. However, the GABAminergic neuron may contain mu-opioid and/or CB1 cannabinoid receptors on its surface. Mu opioid receptors are presynaptic, and inhibit neurotransmitter release. In particular, they inhibit the release of the inhibitory neurotransmitter GABA, and thereby disinhibit the dopamine pathways, causing more dopamine to be released.

Through such mechanisms, opioids and cannabinoids can indirectly modulate neurotransmission [Janice C. Froehlich. Opioid peptides. Alcohol health and research world. 132-136; Anupama Koneru, Sreemantula Satyanarayana and Shaik Rizwan. Endogenous Opioids: Their Physiological Role and Receptors. Global Journal of Pharmacology, 3 (3, 2009): 149-153; Julie LeMerrer, Jerome A. J. Becker, Katia Befort and Brigitte L. Kieffer. Reward Processing by the Opioid System in the Brain. Physiol Rev 89(2009): 1379-1412]. Receptors for opioids are shown in FIG. 8 with a fork or goal-post symbol (Ψ), and the opioids that bind and activate them are shown with a solid square (■). Different types of opioid receptors that modulate neurotransmission are found throughout the brain, but significant ones for present purposes are shown in FIG. 9 in the VTA, nucleus accumbens, VP, parabrachial nucleus, and NTS. Similar receptors for cannabinoids exist throughout the brain (not shown). It is thought that without neuromodulation via the opioid and cannabinoid receptors, the dopmainergic limbic system may generate a feeling of "want", but with the additional receptor systems, a hedonic feeling of "like" (or relief through euphoria) may be generated [Julie LeMerrer, Jerome A. J. Becker, Katia Befort, and Brigitte L. Kieffer. Reward Processing by the Opioid System in the Brain. Physiol Rev 89 (2009): 1379-1412; Kent C. Berridge and Morten L. Kringelbach. Affective neuroscience of pleasure: reward in humans and animals. Psychopharmacology 199 (2008):457-480; Susana PECINA, Kyle S. Smith, and Kent C. Berridge. Hedonic Hot Spots in the Brain. Neuroscientist 12(6, 2006):500-511].

Endorphins are endogenous opioid peptides that function as neurotransmitters, and beta-endorphin is released into the brain from hypothalamic neurons. It is also released into the blood from the pituitary gland under the control of the hypothalamus, but because endorphins cannot pass easily through the blood-brain barrier, only the opioids under direct control of the hypothalamus are shown with the solid square (■) that is attached to the hypothalamus in FIG. 9. The raphe nuclei also cause the release endorphins. Thus, through the production of endogenous opioid peptides, the hypothalamus and raphe nuclei can modulate neurotransmission involving opioid receptors that were described above. The hypothalamus also connects bi-directionally to components of the limbic system, through the medial forebrain bundle. Such bidirectional connections are shown in FIG. 9 to the amygdala, nucleus accumbens, and VTA with arrows on both ends. [Pedro RADA, Jessica R. Barsonb Sarah F. Leibowitz, Bartley G. Hoebel. Opioids in the hypothalamus control dopamine and acetylcholine levels in the nucleus accumbens. Brain Research 1312(2010): 1-9].

According to the foregoing description of FIG. 9, many pathways collectively bring about the euphoria-like mechanism whereby migraine pain production is dissociated from the perception of migraine pain. From the NTS projections, direct inhibition of the nucleus accumbens and indirect inhibition via the amygdala may lead to a reduced GABAnergic signal from the nucleus accumbens to the VTA and VP. Inhibition of the thalamus via the parabrachial nucleus reduces stimulation of the prefrontal cortex, which in turn results in reduced stimulation of the nucleus accumbens. From the NTS input to the hypothalamus, stimulation may (1) produce endogenous opioids that can further inhibit GABAnergic inhibition through binding to the opioid receptors; and (2) directly stimulate the VTA and inhibit the amygdala and/or nucleus accumbens.

Such effects would bring about a significant dopaminergic neurotransmission disinhibition in the VTA, which responds by flooding the nucleus accumbens, amygdala, VP, PFC and hippocampus with dopamine along the dopaminergic projections 81, giving rise to the dissociation. Continued stimulation of the vagus nerve prevents neurotransmitter equilibrium from being restored, during which time gene expression and other biochemical effects alter the physiology of the nerve cells. When stimulation is terminated, the duration of the subsequent dissociation is a function of the time needed for neuronal changes, such as biochemical effects and gene expression that were altered during the stimulation, to be restored to their former equilibria.

The nucleus tractus solitarius (NTS) also connects to structures that were identified above as being involved directly in the pathophysiology of migraine. Those structures include the hypothalamus, periaqueductal gray, locus ceruleus, and raphe nuclei. They are in turn connected to other structures that are more closely linked to the vascular afferents 860 and efferents 861, which are respectively the trigeminocervical complex and superior salivatory nucleus. The hypothalamus may also regulate activity of the thalamus, periaqueductal gray, locus ceruleus, trigeminocervical complex, and cortical structures via its secretion of orexin and other chemicals. Although most pathways from the NTS are shown in FIG. 9 to be unidirectional, it is understood that many of them are in fact bi-directional, such that the NTS receives and processes neural information, rather than simply relaying signals from one place to another [JEAN A. The nucleus tractus solitarius: neuroanatomic, neurochemical and functional aspects. Arch Int Physiol Biochim Biophys 1991; 99(5):A3-A52].

The locus ceruleus is responsible for mediating many of the sympathetic effects during stress, including those associated with migraine. The locus ceruleus is activated by stress and will respond by increasing norepinephrine secretion, which in turn will alter cognitive function through the prefrontal cortex, increase motivation through nucleus accumbens, activate the hypothalamic-pituitary-adrenal axis, and increase the sympathetic discharge as well as inhibit parasympathetic tone through the brainstem. Such inhibition of parasympathetic tone will specifically inhibit the parasympathetic pathway via the superior salivatory nucleus, thereby blocking the positive feedback loop that contributes to the maintenance of migraine pain and thereby bringing about a reduction in sinus congestion and related symptoms.

Much of the integration of autonomic information is performed in the NTS, parabrachial nucleus (PBN), and Edinger-Westphal nucleus (EW). As shown in FIG. 9, the NTS projects to the PBN, and the PBN projects to the EW. Within the brain stem, integration of autonomic activity may occur via pathways that project: (a) from EW to PBN; (b) from PBN to NTS; (c) from NTS to the paraventricular nucleus of the hypothalamus (PVN); and (d) from PVN to EW. Pathways that descend from brain stem centers of autonomic integration to the spinal cord originate in the EW, NTS, and PVN [LEOWY, A. D., Burton, H., 1978. Nuclei of the solitary tract: efferent projections to the lower brain stem and spinal cord of the cat. J. Comp. Neurol. 181, 421-449; LEOWY, A. D., Saper, C. B, 1978. Edinger-Westphal nucleus: projections to the brain stem and spinal cord in the cat. Brain Res. 150, 1-27].

Sympathetic control that is particularly relevant to the present invention is effected via preganglionic fibers that project from the cervicothoracic level of spinal cord to the superior cervical ganglion, which supplies sympathetic innervation to the face. For example, sympathetic nerves to the nose synapse in the superior cervical ganglion, which is shown in FIG. 9. Postsynaptic fibers 862 then travel via the carotid plexus where the deep petrosal nerve originates. The deep petrosal nerve unites with the greater superficial petrosal nerve to form the vidian nerve. The sympathetic fibers then pass through the sphenopalatine ganglion, without synapsing, to reach the nose and paranasal sinus mucosa. Stimulation of this sympathetic nerve induces vasoconstriction, but has little effect on mucous secretion. However, the parasympathetic pterygopalatine ganglion, which supplies the lacrimal gland, paranasal sinuses, and glands of the mucosa of the nasal cavity, also comprises sympathetic efferent (postganglionic) fibers from the superior cervical ganglion. This parasympathetic pathway complements the one shown in FIG. 9 involving the superior salvitory nucleus. Thus, the circuits shown in FIG. 9 show how vagal nerve stimulation may modulate nasal congestion and related symptoms, in migraine headaches and in comorbid conditions such as rhinitis and sinusitis, through modulation of sympathetic and parasympathetic pathways.

The disclosed vagal nerve stimulation may also aid in the prevention of recurrent migraine attacks over a longer period of time, through its effects on the raphe nuclei and locus ceruleus. The raphe nuclei provide extremely widespread serotonergic innervation of the entire cortex, diencephalon, and other brain structures. The NTS projects to multiple raphe nuclei, as do other nuclei of the dorsal medullary vagal complex, but the complexity of NTS-raphe pathways and transmitters is greater than for NTS-locus ceruleus interactions. Thus, the locus ceruleus is the major source of norepinephrine and the raphe of serotonin in most of the brain, and the NTS projects to both of them. Migraine is a disease in which both norepinephrine and serotonin are chronically low, and stimulation of the locus ceruleus and raphe nuclei via the NTS may ameliorate that problem, at a minimum as a prophylactic [Stephen J. Peroutka. Migraine: a chronic sympathetic nervous system disorder. Headache 44(2004): 53-64; E. HAMEL. Serotonin and migraine: biology and clinical implications. Cephalalgia 27 (2007): 1295-1300].

The disclosed devices and methods may also be used to treat types of headaches that are co-morbid with migraine, or that overlap in symptoms such that a diagnosis of migraine versus the other headache is difficult. One such headache with potentially overlapping symptoms is cluster headache [A O Kaup, N T Mathew, C Levyman, J Kailasam, L A Meadors and S S Villarreal. 'Side locked' migraine and trigeminal autonomic cephalgias: evidence for clinical overlap. Cephalalgia 23(2003): 43-49].

Cluster headache is a relatively rare but very painful disorder affecting males more than females. Its attacks come in clusters typically occurring 6 to 12 weeks at a time, anywhere from one to three times a year. The duration of a cluster headache 15 minutes to 3 hours, often beginning at night shortly after the patient has gone to sleep, and may recur two to six times during the night and into the next day. The pain is localized unilaterally in or around the eye, and almost invariably, cluster headache is accompanied by autonomic symptoms such as lacrimation, eye redness, drooping eyelid, nasal stuffiness, and runny nose [Arne May. Cluster headache: pathogenesis, diagnosis, and management. Lancet 366(2005): 843-55].

Anatomical structures identified in FIG. 9 in connection with migraine are also involved in cluster headaches, including the trigeminovascular system, but the key site for triggering the pain and controlling the cycling features of the headache is in the posterior hypothalamic grey matter region. The associated autonomic dysregulation might originate centrally in association with the hypothalamic disturbance, or through trigeminal discharge, or through compression of pericarotid sympathetic fibers due to vasodilation or perivascular edema that is evoked by parasympathetic overactivity during attacks [Peter J Goadsby. Pathophysiology of cluster headache: a trigeminal autonomic cephalgia. Lancet Neurology 1(2002): 251-57; Massimo Leone, Gennaro Bussone. Pathophysiology of trigeminal autonomic cephalalgias. Lancet Neurol 8(2009): 755-64]. Trauma may also be involved in the pathogenesis of cluster headaches [Russell W. Walker. Cluster Headache and Head Trauma: Is There an Association? Current Pain and Headache Reports 11(2007): 137-140].

Inhalation of pure oxygen via a non-rebreathing facial mask is effective at stopping cluster headache attacks, and it is used for treatment in conjunction with migraine treatments, including sumatriptan and oral ergotamine. Because there is highly specific activation of the hypothalamic grey matter in cluster headache, deep brain stimulation (DBS) in the hypothalamus is used to treat refractory cases [A Mauskop. Vagus nerve stimulation relieves chronic refractory migraine and cluster headaches. Cephalalgia 25(2005):82-96; Robert Levy, Timothy R. Deer, and Jaimie Henderson. Intracranial Neurostimulation for Pain Control: A Review. Pain Physician 13(2010):157-165]. Vagal nerve stimulation has also been used in conjunction with DBS [Angelo Franzini, G. Messina, Massimo Leone, Alberto Proietti Cecchini, Giovanni Broggi and Gennaro Bussone. Feasibility of simultaneous vagal nerve and deep brain stimulation in chronic cluster headache: case report and considerations. Neurol Sci 30 (Suppl 1, 2009): S137-S139]. The present invention differs from other VNS treatments for cluster headaches in that it may be performed without DBS and non-invasively, including using magnetic stimulation, and in that it involves modulation of glutamate or glutamate receptors (e.g., Pathways 83 in FIG. 9).

The disclosed devices and methods may also be used to treat rhinitis and sinusitis, irrespective of whether the nasal or paranasal sinus problems are accompanied by a headache. Rhinitis usually refers to inflammation of the mucus membranes of the nose (although inflammatory cell infiltrates are not characteristic of all disorders considered to be rhinitis), whereas sinusitis usually refers to inflammation in the sinuses. The distinction may be understood from the following two paragraphs.

The nasal cavity is divided by the nasal septum, and small, rounded, bony projections known as turbinates are located within the breathing passage to promote air filtration, humidification, and temperature regulation. The nasal cavity and turbinates are lined with mucosa containing interspersed goblet cells that secrete a thin layer of mucus that is moved by ciliary action to the posterior nasopharynx. Below the mucosa, the submucosa comprises serous and mucus-producing seromucous nasal glands, nerves, and extensive vasculature. Thus, the secretory tissue of the nose includes epithelial cells, submucosal glands, and relatively large anterior or lateral serous glands. The vasculature of the nose contains capacitance vessels such as sinusoids and distensible venules, as well as arteriovenous anastomoses, arterioles, and capillaries. As described below, the nerves of the nasal cavity comprise trigeminal sensory (nociceptive), sympathetic, and parasympathetic nerve fibers.

Hollow, normally air-filled cavities in the bones of the face and skull, known as the paranasal sinuses, lie adjacent to the nose, and each sinus is connected to the nasal cavity by a small opening (an ostium). Mucosa also lines the sinuses, which is continuous with the mucosa of the nasal cavity through the ostia. Thus, rhinitis and sinusitis may both involve mucosal inflammation, but in adjacent, interconnected anatomical structures [James N. BARANIUK. Neural regulation of mucosal function. Pulmonary Pharmacology & Therapeutics 21 (2008): 442-448; Peter H. HWANG. Review of Acute Rhinosinusitis—A 51-Year-Old Woman With Acute Onset of Facial Pressure, Rhinorrhea, and Tooth Pain. JAMA. 301(2009, 17): 1798-1807].

Rhinitis can be caused by allergic, nonallergic, infectious, hormonal, occupational, and other factors. Allergic rhinitis is traditionally thought of as being either seasonal or perennial, reflecting the prevailing pollen levels. The term "vasomotor rhinitis" has been used to refer to a form of nonallergic rhinitis that may be due to parasympathetic hyperactivity and sympathetic hypoactivity, which may be particularly relevant to migraine patients with nasal congestion [Timothy L. SMITH. Vasomotor rhinitis is not a wastebasket diagnosis. Arch Otolaryngol Head Neck Surg 129 (2003):584-587]. Nonallergic rhinitis may be triggered (other than by allergens), for example, by cold air, spicy foods, and aspirin or other drugs. Approximately 44% to 87% of patients with rhinitis might have mixed rhinitis, which is a combination of allergic and nonallergic rhinitis [J. BOUSQUET et al. Allergic Rhinitis and its Impact on Asthma (ARIA) 2008 Update. Allergy 63 (2008, Suppl. 86): 8-160; Mark S. DYKEWICZ and Daniel L. Hamilos. Rhinitis and sinusitis. J Allergy Clin Immunol 125(2010):S103-15; R. J. SALIB, P. G. Harries, S. B. Nair, P. H. Howarth. Mechanisms and mediators of nasal symptoms in nonallergic rhinitis. Clinical and Experimental Allergy, 38(2008), 393-404].

The symptoms of rhinitis and sinusitis overlap, and sinusitis rarely occurs in the absence of rhinitis. When nasal inflammation accompanies sinusitis, it is referred to as rhinosinusitis. The most common cause of rhinosinusitis is viral infection (the common cold), but rhinosinusitis may also be caused by microorganisms and fungus; noninfectious, nonimmunologic causes; and allergic and nonallergic immunologic inflammation. Rhinosinusitis is typically classified as acute or chronic, depending on whether the symptoms last for less than twelve weeks or not (according to a common definition, but four weeks is also used). When the nose is chronically inflamed, most notably with eosinophil infiltration, polyps may form within the nasal cavity (polyposis), exacerbating the nasal congestion. Nasal polyps and chronic rhinosinusitis are often taken together as one disease entity, because it seems impossible to clearly differentiate between them. Nasal polyposis is therefore considered to be a subgroup of chronic rhinosinusitis. Physical problems affecting the structure of the nasal passage can also cause nasal congestion, including such problems as septal deviation and adenoid hypertrophy [Mark S. DYKEWICZ and Daniel L. Hamilos. Rhinitis and sinusitis. J Allergy Clin Immunol 125(2010):S103-15; Yvonne CHAN and Frederick A. Kuhn. An update on the classifications, diagnosis, and treatment of rhinosinusitis. Current Opinion in Otolaryngology & Head and Neck Surgery 17(2009):204-208; Andrew J WOOD and Richard G Douglas. Pathogenesis and treatment of chronic rhinosinusitis. Postgrad Med J 86(2010): 359-364; Michael S. BENNINGER. Adult chronic rhinosinusitis: Definitions, diagnosis, epidemiology, and pathophysiology. Otolaryngology—Head and Neck Surgery 129 (2003, 3 Supplement):S1-S32].

The first step in the management of rhinitis and sinusitus is prevention by avoidance of causative agents. Subsequent management may include pharmacological and possibly surgical treatment. Conventional treatments for rhinitis include the following classes of drugs: antihistamines, corticosteroids, decongestants, leukotriene receptor agonists, anticholinergics, and mast cell stabilizers (e.g., cromolyn), each of which might be administered orally or intranasally. Immunotherapy, which consists of repeated subcutaneous injections of potent standardized extracts of specific allergens, may also be tried [Erwin W. GELFAND and Marshall Plaut. Current Trends in Allergic Reactions: A multidisciplinary approach to patient management. CLINICIAN 21(2003, 3): 7-12; Eli O. MELTZER. Evaluation of the optimal oral antihistamine for patients with allergic rhinitis. Mayo Clin Proc. 80(2005, 9):1170-1176]. Depending on the suspected etiology, sinusitis may be treated with antibiotics, corticosteroids, or surgery [Yvonne CHAN and Frederick A. Kuhn. An update on the classifications, diagnosis, and treatment of rhinosinusitis. Current Opinion in Otolaryngology & Head and Neck Surgery 17(2009):204-208; Andrew J WOOD and Richard G Douglas. Pathogenesis and treatment of chronic rhinosinusitis. Postgrad Med J 86(2010): 359-364].

However, the patient may experience considerable discomfort and diminished quality of life during the management of a severe episode of rhinitis or acute sinusitis. Furthermore, chronic sinusitis, lasting for 12 or more weeks, may be particularly difficult to treat. Individuals with sinus polyposis have a high recurrence rate, even after surgery [Rhoda WYNN and Gady Har-El. Recurrence rates after endoscopic sinus surgery for massive sinus polyposis. Laryngoscope 114(2004):811-813]. Common side effects for decongestants include insomnia, irritability, palpitations, and hypertension. Side effects for antihistamines include bitter taste and somnolence. Side effects for anticholinergics include nasal dryness. Side effects for corticosteroids include nasal bleeding and septal perforation. Side effects for antibiotics include allergic reaction. Accordingly, there is need in the art for treatments that promptly reduce the symptoms associated with rhinitis and sinusitis, without producing such side effects. Special populations such as children, the elderly, and pregnant women are especially in need of improved treatments. Therefore, additional non-pharmacological methods have been developed to treat rhinitis and sinusitis. They include nasal saline irrigation [HARVEY R, Hannan S A, Badia L, and Scadding G. Nasal saline irrigations for the symptoms of chronic rhinosinusitis. Cochrane Database of Systematic Reviews 2007, Issue 3. Art. No.: CD006394], acupuncture [Jonathan ROBERTS, Aarnoud Huissoon, Janine Dretzke, Dechao Wang and Christopher Hyde. A systematic review of the clinical effectiveness of acupuncture for
  allergic rhinitis. BMC Complementary and Alternative Medicine 8(2008):13, pp. 1-10], and vidian neurectomy [Akiyoshi KONNO. Historical, Pathophysiological, and Therapeutic Aspects of Vidian Neurectomy. Curr Allergy Asthma Rep 10(2010):105-112].

An objective of the present invention to provide a novel non-pharmacological treatment for the symptoms that are associated with rhinitis and sinusitis, using magnetic or electrode-based vagus nerve stimulation (VNS) as taught herein. The disclosed treatment may be performed irrespective of the presence of a comorbid condition, such as migraine or cluster headache. Evidence for the originality of the disclosed methods and devices comes from the fact that nasal congestion, rhinitis and sinusitis have been reported as adverse events in patients treated with VNS, which teach away from the present invention [Paula CORABIAN and Patricia Leggett. Vagus Nerve Stimulation for Refractory Epilepsy, page 15. HTA 24:Series A March 2001, Alberta Heritage Foundation for Medical Research 1500, 10104-103 Avenue. Edmonton, Alberta T5J4A7, CANADA; U.S. Food and Drug Administration. 4047b1_00_FDA Clinical Review Memo (2004), page 47. FDA. Division of General, Restorative, and Neurological Devices, 9200 Corporate Boulevard HFZ-410, Rockville, Md. 20850]. Other reports are silent about the effects of vagus nerve stimulation on the symptoms of rhinitis and sinusitis. MAUSKOP describes two cluster headache patients who had nasal congestion and lacrimation and whose headache was successfully treated with vagal nerve stimulation, but he does not indicate whether the VNS also helped reduce the nasal congestion and lacrimation [A MAUSKOP. Vagus nerve stimulation relieves chronic refractory migraine and cluster headaches. Cephalalgia 25(2005): 82-86]. Another report describes a patient with nasal congestion, but it does not indicate whether VNS helped reduce the congestion [Angelo FRANZINI, G. Messina, Massimo Leone, Alberto Proietti Cecchini, Giovanni Broggi, Gennaro Bussone. Feasibility of simultaneous vagal nerve and deep brain stimulation in chronic cluster headache: case report and considerations. Neurol Sci 30 (2009, Suppl 1):S137-S139]. Otherwise, patients treated with VNS have not been reported to experience either nasal congestion or decongestion, either prior to treatment or as a side effect of the VNS treatment [Harold A. SACKEIM, A. John Rush, Mark S. George, Lauren B. Marangell, Mustafa M. Husain, Ziad Nahas, Christopher R. Johnson, Stuart Seidman, Cole Giller, Stephen Haines, Richard K. Simpson, Jr., and Robert R. Goodman. Vagus Nerve Stimulation (VNS) for Treatment-Resistant Depression: Efficacy, Side Effects, and Predictors of Outcome. Neuropsychopharmacology 25(2001, 5): 713-728].

U.S. Pat. No. 7,877,146, entitled Methods of treating medical conditions by neuromodulation of the sympathetic nervous system, to REZAI et al. mentions rhinitis, sinusitis, and nasal congestion as conditions that may be treated by electrical stimulation, but does not teach the use of vagus nerve stimulation.

U.S. Pat. No. 7,885,709, entitled Nerve stimulation for treating disorders, to BEN-DAVID, teaches vagus nerve stimulation, but only for patients with heart failure, and only discloses rhinitis and sinusitis within a long list of medical conditions.

Patent application US20050075702, entitled Device and method for inhibiting release of pro-inflammatory mediator, to SHAFER, teaches stimulating the vagus nerve, to inhibit release of a proinflammatory mediator, listing rhinitis and sinusitis within a long list of medical conditions, but only in connection with co-stimulation of a sympathetic neuron and does not even consider inhibition of histamine or other mechanisms that do not involve proinflammatory mediators. Furthermore, the present invention uses different electrical stimulation parameters than those used by SHAFER, and the present invention may stimulate the vagus nerve magnetically and noninvasively.

Patent application US20060178703, entitled Treating inflammatory disorders by electrical vagus nerve stimulation, to HUSTON et al., discloses stimulation of the vagus nerve to treat an individual . . . at risk for an inflammatory disorder . . . provided that . . . the condition is not asthma . . . . The application names sinusitis and rhinitis in a long list of disorders that may be so treated. However, the present invention uses different electrical stimulation parameters than those used by Huston et al., and the present invention may stimulate the vagus nerve magnetically and noninvasively. Furthermore, asthma may be comorbid with sinusitis and rhinitis, such that BOUSQUET et al write "Most patients with asthma have rhinitis, suggesting the concept of "one airway one disease" [J. BOUSQUET et al. Allergic Rhinitis and its Impact on Asthma (ARIA) 2008 Update. Allergy 63 (2008, Suppl. 86): 8-160]. However, HUSTON et al. do not explain how their disclosed method could treat sinusitis or rhinitis without also treating actual or potential asthma. Moreover, although cytokine-mediated inflammation may secondarily promote the dilation and engorgement of the veins within the nose and sinuses, increased mucus secretion, and increased vascular permeability causing tissue swelling/edema that is associated with rhinitis and sinusitis, it is possible for those three traits to occur through other non-cytokine mechanisms, such as histamine release, sympathetic hypoactivity, and parasympathetic hyperactivity. Those other mechanisms may also be modulated by vagus nerve stimulation, without necessarily having a significant effect on cytokine-mediated inflammation.

The devices and methods for treatment of rhinitis and sinusitis by stimulation of the vagus nerve are those described above and illustrated in FIGS. 1 to 7. Portions of FIGS. 8 and 9 are also relevant to the mechanism of treatment of sinusitis and rhinitis, as indicated below. Applicant believes that at least one of the primary mechanisms of action for treating sinusitis and rhinisits according to the present invention is by causing the systemic release of natural, endogenous β-agonists, epinephrine and norepinephrine, which counteract the effects of histamine on the symptoms of these disorders. The electrical field delivered to the vagus nerve by the device(s) of the prevent invention has been optimized to stimulate the release of these hormones into the circulation at concentrations that produce a reduction in the symptoms associated with sinusitis and/or rhinitis, but have little affect on heart rate or blood pressure. In one embodiment of the present invention, the release of these catecholamines is accomplished by generating a parasympathetic, afferent vagal signal to the brain, which then triggers an efferent sympathetic signal to stimulate the release of catecholamines from the adrenal glands. In animal studies demonstrating the effects of applicant's signal for treating bronchoconstriction, data has indicated that the device(s) of the present invention can be effective even if the vagus nerve is tied off distal to the electrode and that the bronchodilation effect can be blocked with the β-blocker propranolol. In addition, stimulation is ineffective in animals that have had their adrenal glands removed (the endogenous source of these catecholamines). Simon B J, Emala C W, Lewis L M, Theodoro D, Purim-Shem-Tov Y, Sepulveda P, Hoffmann T J, Staats P. Vagal Nerve Stimulation for Relief of Bronchoconstriction: Preliminary Clinical Data and Mechanism of Action. *NANS 13th Meeting*, Las Vegas, December 2009. Hoffmann T J, Mendez S, Staats, P, Emala C, Guo P. Inhibition of Histamine-Induced Bronchoconstriction in Guinea Pig and Swine by Pulsed Electrical Vagus Nerve Stimulation. *Neuromodulation.* 2009; 12: 261-269.

In one embodiment of the invention, the presently disclosed vagus nerve stimulation (VNS) differs from VNS as it is currently practiced for treatment of epilepsy, depression, and other disorders in that the stimulation may be performed alternately on the left and right vagus nerves in the neck, as needed. The position alternation is performed because in approximately 80 percent of individuals, nasal congestion cycles between the left and right sides of the nose, with a cycle time of from 50 minutes to four hours, the amplitude of which is influenced by posture [KENNEDY D W, Zinreich S J, Kumar A J, Rosenbaum A E, Johns M E. Physiologic mucosal changes within the nose and ethmoid sinus: imaging of the nasal cycle by MRI. Laryngoscope (1988, 9):928-933]. Thus, positioning of the stimulating device may be in response to the patient's reporting of nostril patency, or it may be performed more objectively by methods known in the art to evaluate congestion, such as MRI imaging, rhinoscopy, acoustic rhinometry, rhinomanometry, plythsomography, or thermometry, for example, by placing a thermistor under each nostril. Such direct or indirect, continuous or intermittent measurements of nasal patency are also useful in documenting the response of the patient's nose and sinus congestion to vagal nerve stimulation.

Migraine, rhinitis and sinusitis may all result in nasal inflammation, nasal obstruction, runny nose (rhinorrea), mucus discharge, nasal itching and sneezing. They often also occur with symptoms of inflammation of the outer eye (conjunctivitis) as evidenced by watery and red eyes. These symptoms may also result from conditions such as Horner's syndrome, nasal reflex sympathetic dystrophy, rhinitis medicamentosa, and treatment with alpha-adrenergic antagonists. Consequently, the comorbitity and mixture of rhinitis, sinusitis, and other conditions with migraine/sinus headache may make it difficult to attribute those symptoms to any one medical condition. Nevertheless, whatever its etiology, nasal congestion and blockage may be understood to result from at least the following factors: dilation and engorgement of the veins within the nose and sinuses, increased mucus secretion, and/or increased vascular permeability causing tissue swelling/edema, wherein each such factor may also possibly be promoted by a variety of cell types and chemicals (e.g., mast cells and histamine).

Nerves within the nose and sinus may affect each of those factors. Those nerves may also modulate the sensory perception of nasal/sinus congestion, for example, wherein stimulation of nerves by metholated vapors decreases the sensation of congestion (but not the degree of actual congestion), or wherein abnormal primary afferent signaling gives rise to the sensation of congestion even in the absence of inflammation and impaired nasal airflow [Robert M NACLERIO, Claus Bachert, James N Baraniuk. Pathophysiology of nasal congestion. International Journal of General Medicine 3(2010): 47-57]. As disclosed herein, the present invention uses vagus nerve stimulation to ameliorate the symptoms associated with rhinitis and sinusitis, by affecting the above-mentioned factors, primarily through modulation of nerves of the nose and paranasal sinuses that are associated with the sympathetic and parasympathetic nervous system, via circuits comprising those described above in connection with FIG. 9. Such circuits may include the entire feedback loop of a reflex initiated by irritants, or only components of the loop. Thus, the methods may also modulate sensory nerves that are associated with the trigeminal nerve, as well as the perception of congestion and other symptoms associated with rhinitis and sinusitis, via circuits comprising those that are also described above in connection with FIG. 9.

The nose has a complex nervous system that includes sensory, parasympathetic, and sympathetic nerves. Sensory nerves derived from the trigeminal ganglion transmit signals from the mucosa, leading to the sensations of itching and congestion and to reflexes such as sneezing. The parasympathetic and sympathetic nerves of the nose affect the glandular and vascular nasal apparatuses. Neural function can be chronically upregulated in the presence of mucosal inflammation. It can also be acutely upregulated with an allergic reaction, or acutely upregulated in the absence of inflammation in cases of nonallergic rhinitis [Seema SARIN, Bradley Undem, Alvin Sanico, and Alkis Togias. The role of the nervous system in rhinitis. J Allergy Clin Immunol 118(2006): 999-1014; Brendan J. CANNING. Neurology of Allergic Inflammation and Rhinitis. Current Allergy and Asthma Reports 2002, 2:210-215; Dennis KIM and James N. Baraniuk. Neural aspects of allergic rhinitis. Curr Opin Otolaryngol Head Neck Surg 15(2007): 268-273; James N. BARANIUK. Neurogenic Mechanisms in Rhinosinusitis. Current Allergy and Asthma Reports 1(2001): 252-261; James N. BARANIUK, Kristina Naranch Petrie, Uyenphuong Le, Chih-Feng Tai, Yong-Jin Park, Atsushi Yuta, Mushtaq Ali, Christopher J. VandenBussche, and Benjamin Nelson. Neuropathology in Rhinosinusitis. Am J Respir Crit Care Med 171(2005): 5-11].

The parasympathetic innervation of the nasal airways, as well as of the anterior nasopharynx and ethmoid sinuses, originates from the facial nucleus of the brain stem and the superior salivatory nucleus. Preganglionic fibers follow the greater superficial petrosal nerve and the vidian nerve to synapse in the sphenopalatine ganglion (see FIG. 9). Postganglionic fibers innervate serous and mucous glands, arteries, veins, and arteriovenous anastomoses. Stimulation of the parasympathetic nerves causes glandular secretions rich in mucous glycoproteins, lactoferrin, lysozyme, secretory leukoprotease inhibitor, neutral endopeptidase, and secretory IgA. In addition, vasodilation can be induced by means of direct stimulation of parasympathetic nasal nerves, probably mediated by vasoactive intestinal peptide. Thus, inhibition of the parasympathetic nerves by the disclosed vagus nerve stimulation can inhibit nasal congestion or promote nasal decongestion by inhibiting glandular secretion or by inhibiting vasodilation, independent of other mechanisms.

Sympathetic input in the nose originates from preganglionic fibers in the thoracolumbar region of the spinal cord, which pass into the vagosympathetic trunk and relay in the superior cervical ganglion (see FIG. 9). The nasal vascular bed is primarily under sympathetic nervous control. Congestion of nasal mucosa may be caused by dilatation of venous sinusoids and/or collecting veins and constriction of outflow veins, both of which can increase mucosal blood volume. Opposite changes in these mechanisms promote mucosal decongestion. Adrenergic mechanisms play principal roles in the sympathetic control of nasal venous systems. Although both alpha- and beta-adrenoceptors exist in all nasal venous vessels, upon sympathetic nerve stimulation, the alpha-adrenergic constrictive effect is seen in the lateral collecting vein, septal collecting vein, anterior collecting vein, dorsal nasal vein and septal mucosa, whereas a beta-adrenergic relaxant effect is seen in the sphenopalatine vein. According to the vascular arrangements in the nasal mucosa, constriction of the venous sinusoid septal mucosa and collecting veins (anterior collecting vein, lateral collecting vein, and septal collecting vein) of both venous systems will decrease mucosal blood volume. Relaxation of posterior outflow vein (sphenopalatine vein), coupled with constriction of anterior outflow vein (dorsal nasal vein), will favor venous drainage through the posterior venous system. Thus, stimulation of the nasal and paranasal sinus sympathetic nerves by the disclosed vagus nerve stimulation may promote nasal decongestion, independent of other mechanisms, by constriction of venous sinusoids and/or collecting veins and/or dilation of outflow veins [Min WANG and Mary A. Lung. Adrenergic mechanisms in canine nasal venous systems. British Journal of Pharmacology 138(2003): 145-155].

All forms of nasal symptoms can be induced entirely by neural mechanisms, which occur in normal, healthy individuals in response to unavoidable environmental irritants. In some such individuals, non-allergic rhinitis (nonallergic, noninfectious rhinitis; idiopathic rhinitis; and vasomotor rhinitis) might represent hyperresponsive variability that is found within a population of individuals, or day-to-day variability for a given individual, but still within a wide physiological range that is observed in response to irritants. In hyperresponsive individuals, sensory nerves may respond to normally subthreshold stimuli; sensory ganglia could be hyperresponsive; synaptic transmission within the central nervous system could be unusually efficacious; autonomic ganglia signal-filtering could be unusual, and autonomic nerve terminals may be overly potentiated. Accordingly, effects of the disclosed vagal nerve stimulation that inhibit hyper-responsiveness originating at any such component of the nervous system may counteract the symptoms of rhinitis and sinusitis.

However, symptoms such as a runny nose and nasal congestion can also be generated by biochemical mediators that are produced during an immune response or under an inflammatory condition. In particular, symptoms of rhinitis may be caused by an increase in histamine, which is triggered by airborne allergens in allergic rhinitis. Within minutes of inhalation of an allergen in sensitized subjects, the allergens are recognized by IgE antibody that is bound to mast cells, causing degranulation of the mast cell and release of preformed mediators, particularly histamine. The released histamine then acts directly on H1, H2, and H3 receptors on the nasal vasculature to cause vasodilation and increased vascular permeability.

the histamine H3 effect in nasal mucosa may be attributed to a prejunctional inhibition of norepinephrine release from sympathetic neurons, which would otherwise promote nasal patency [Thomas TAYLOR-CLARK, Reena Sodha, Ben Warner and John Foreman. Histamine receptors that influence blockage of the normal human nasal airway. British Journal of Pharmacology 144(2005): 867-874; LoriAnn M. VARTY, Eric Gustafson, Maureen Laverty, John A. Hey. Activation of histamine H3 receptors in human nasal mucosa inhibits sympathetic vasoconstriction. European Journal of Pharmacology 484(2004): 83-89]. Histamine is also found to coexist widely with norepinephrine within sympathetic nerves that innervate different tissues in different species, such that histamine is now recognized to be a neurotransmitter of the sympathetic nerve system [HE G, Hu J, Ma X, Li M, Wang H, Meng J, Jia M, Luo X. Sympathetic histamine exerts different pre- and post-synaptic functions according to the frequencies of nerve stimulation in guinea pig vas deferens. J Neurochem 106(2008, 4):1710-1719]. Thus, nasal histamine may originate not only from mast cell degranulation, but also from the sympathetic nerves themselves. Accordingly, effects of the disclosed vagus nerve stimulation that inhibit the synthesis or release of histamine from sympathetic nerves, and effects that inhibit the synthesis or activity of histamine receptors, will promote uninhibited norepinephrine release within the nose and sinuses, and inhibit vasodilation and increased vascular permeability, by counteracting the potential role of histamine in promoting the symptoms of rhinitis and sinusitis.

Extensive crosstalk exists between nerves and mast cells in the nose and most other tissue (870 in FIG. 8B). Stimulation of parasympathetic nerve endings through the vidian nerve, which provides the main parasympathetic nerve supply to nasal respiratory and maxillary sinus mucosa, is associated with a significant increase in histamine release from mucosal mast cells in patients with vasomotor rhinitis [MASINI E, Rucci L, Cirri-Borghi M B, Giannella E, Mannaioni P F. Stimulation and resection of Vidian nerve in patients with chronic hypertrophic non-allergic rhinitis: effect on histamine content in nasal mucosa. Agents and Actions/Inflammation Research 18(1986, 1/2): 251-3.; L. RUCCI, E. Masini, M. B. Cirri Borghi, E. Giannella and P. F. Mannaioni. Histamine release from nasal mucosal mast cells in patients with chronic hypertrophic non-allergic rhinitis, after parasympathetic nerve stimulation. Agents and Actions/Inflammation Research 25 (1988, 3/4): 314-320]. In this context, histamine released from mucosal mast cells by cholinergic stimulation could enhance the parasympathetic response of glands and vessels. Thus, there appears to be a functional relationship between parasympathetic innervation, tissue histamine synthesis and stores, and mast cell degranulation [R. J. SALIB, P. G. Harries, S. B. Nair, and P. H. Howarth. Mechanisms and mediators of nasal symptoms in non-allergic rhinitis. Clinical and Experimental Allergy 38(2008): 393-404]. Accordingly, effects of the disclosed vagus nerve stimulation that inhibit the parasympathetic nerves of the nose and paranasal sinuses will counteract the potential role of mast cells and histamine in promoting the symptoms of rhinitis and sinusitis.

Many other nerve/mast cell associations have been shown to occur between all subtypes of mast cells and substance P- and CGRP-containing neurons, wherein mast cell degranulation and histamine release is promoted [HANNEKE P. M. van der Kleij and John Bienenstock. Significance of Conversation between Mast Cells and Nerves. Allergy, Asthma, and Clinical Immunology 1(2005, 2):65-80]. As described above, such nerve cells comprise the sensory nerves that are associated with the trigeminal nerve, including the maxillary (V2) branch that innervates the nose. Accordingly, effects of the disclosed vagus nerve stimulation that inhibit the release of substance P, CGRP, and related molecules from the sensory nerves in the nose and paranasal sinuses, including effects that inhibit antidromal trigeminal nerve activity, may also inhibit the release of histamine and other molecules from mast cells, thereby inhibiting the symptoms of rhinitis and sinusitis.

It is understood that above-mentioned effects of the disclosed vagus nerve stimulation, which inhibit or counteract mast cell degranulation and histamine release, will also inhibit the effects of other pre-stored mediators within mast cells, such as serine proteases, proteoglycans, sulphatases, and tumour necrosis factor. Such inhibition will also prevent a second or third wave of mast cell mediators from even being synthesized, much less released, including prostaglandins, leukotrienes, and cytokines such as interleukin (IL)-4, IL-5, IL-6, IL-8, and IL-13.

It is also understood that effects of the disclosed vagus nerve stimulation may involve systemic mechanisms in addition to local mechanisms, particularly systemic sympathetic mechanisms. In that regard, it is noted that the brain stem parasympathetic nuclei can independently regulate nasal, laryngeal, and tracheobronchial efferent responses to irritant stimulation in each respiratory tract location. This contrasts with the more generalized, "all-or-nothing" systemic response of the sympathetic nervous system. With this in mind, hyperactivity of the parasympathetic nervous system, which generally responds on time scales that are much shorter than time scales typical of the sympathetic nervous system, may be in part a homeostatic response to hypoactivity of the slower-responding sympathetic nervous system. Consistent with this view is the observation that systemic sympathetic hypofunction is ordinarily found in allergic rhinitis patients. However, the parasympathetic system in such patients is often normal, at least as indicated by cardiovagal measurements, which suggests a prompt adaptation of the parasympathetic nervous system to the prevailing level of activity of the sympathetic nervous system [Stacey L. ISHMAN, Timothy J. Martin, Daniel W. Hambrook, Timothy L. Smith, Safwan S. Jaradeh and Todd A. Loehrl. Autonomic nervous system evaluation in allergic rhinitis. Otolaryngology—Head and Neck Surgery 136 (2007): 51-56]. Accordingly, to the extent that the disclosed vagus nerve stimulation enhances the activity of the sympathetic nervous system systemically, for example, by inducing the release of catecholamines (epinephrine and/or norepinephrine) from the adrenal glands and/or from nerve endings that are distributed throughout the body, then this may also result in a corresponding homeostatic local adaptation of activity of the parasympathetic nervous system.

The disclosed devices and methods may also be used to treat additional disorders that may be co-morbid with migraine, such as anxiety disorders, in which the nervous system may also be hyper-reactive and in which attacks may be triggered by some of the same factors that trigger migraine and asthma attacks. The annual prevalence of anxiety disorders is eighteen percent in the general population, divided among particular forms of anxiety disorders (panic disorder, agoraphobia without panic, specific phobia, social phobia, generalized anxiety disorder, posttraumatic stress disorder, obsessive-compulsive disorder, separation anxiety disorder) [Ronald C. Kessler, Wai Tat Chiu, Olga Demler, Ellen E. Walters. Prevalence, Severity, and Comorbidity of 12-Month DSM-IV Disorders in the National Comorbidity Survey Replication. Arch Gen Psychiatry 62(2005):617-627].

Compared to individuals without migraine, migraineurs are 3.7 to 6.6 times more likely to be diagnosed with panic disorder, 5.7 times more likely to suffer from generalized anxiety disorder, 5.1 times more likely to suffer from obsessive-compulsive disorder, and 2.6 times more likely to be diagnosed with a phobia [H. C. DIENER, M. Küper, and T. Kurth. Migraine-associated risks and co-morbidity. J Neurol (2008) 255:1290-1301; Nathalie Jette, Scott Patten, Jeanne Williams, Werner Becker, Samuel Wiebe. Comorbidity of Migraine and Psychiatric Disorders—A National Population-Based Study. Headache 2008; 48:501-516; Shuu-Jiun WANG, Ping-Kun Chen and Jong-Ling Fuh. Co-morbidities of migraine. Frontiers in Neurology 1 (Article 16, 2010): pp. 1-9. doi: 10.3389/fneur.2010.00016; Stephen D. Silberstein. Shared Mechanisms and Comorbidities in Neurologic and Psychiatric Disorders. Headache 41(Supplement s1, 2001): S11-S18].

The treatment of anxiety disorders is important in and of itself, but it is all the more important in migraineurs because co-morbid anxiety disorder is associated with a progression from episodic migraines to chronic migraines [Todd A. Smitherman, Jeanetta C. Rains, and Donald B. Penzien. Psychiatric Comorbidities and Migraine Chronification. Current Pain and Headache Reports 13(2009):326-331]. It should be noted that anxiety disorders are comorbid with asthma, in addition to migraine, and all three may involve triggers and hypersensitivity [Peter P. Roy-Byrne, Karina W. Davidson, Ronald C. Kessler, et al. Anxiety disorders and comorbid medical illness. General Hospital Psychiatry 30 (2008) 208-225; Naomi M. Simon and Diana Fischmann. The implications of medical and psychiatric comorbidity with panic disorder. J Clin Psychiatry 66(Supplement 4, 2005): 8-15]. Some of the association between migraine and anxiety disorders occurs in individuals who suffer from vertigo, which may be considered to be a special type of disease entity with its own pathophysiology [J M Furman, C D Balaban, R G Jacob, D A Marcus. Migraine-anxiety related dizziness (MARD): a new disorder? J Neurol Neurosurg Psychiatry 2005 76: 1-8; Naomi M. Simon and Diana Fischmann. The implications of medical and psychiatric comorbidity with panic disorder. J Clin Psychiatry 66(Supplement 4, 2005): 8-15].

Part of the association between migraine and anxiety disorder may be also due to a common genetic disposition, for example with genes related to serotonin and/or to dopamine being involved [Xenia Gonda, Zoltan Rihmer, Gabriella Juhasz, Terezia Zsombok, Gyorgy Bagdy. High anxiety and migraine are associated with the s allele of the 5HTTLPR gene polymorphism. Psychiatry Research 149

(2007) 261-266; Stephen J. Peroutka, Susan C. Price, Tara L. Wilhoit, and Keith W. Jones. Comorbid Migraine with Aura, Anxiety, and Depression Is Associated with Dopamine D2 Receptor (DRD2) NcoI Alleles. Molecular Medicine 4(1998): 14-21]. More generally though, the association between migraine and anxiety disorder has been attributed to three mechanisms: aberrant serotonergic (5-HT) functioning, medication overuse or drug abuse (e.g., long-term use of "Ecstasy"), and psychological mechanisms (fear of pain, fear of anxiety-related sensations, i.e., anxiety sensitivity, and unwarranted avoidance behaviors) [Todd A. Smitherman, Jeanetta C. Rains, and Donald B. Penzien. Psychiatric Comorbidities and Migraine Chronification. Current Pain and Headache Reports 13(2009):326-331].

The particular anxiety disorder that is cited as being most consistently associated with migraine is panic disorder, so in what follows, treatment of panic disorder will be specifically discussed, with the understanding that other anxiety disorders may be treated as well. As with migraine, panic disorder occurs preferentially in women, and its prevalence increases in adolescence and decreases with old age. Like migraine, panic disorder attacks are said to be triggered, and as in migraine the most commonly reported antecedent trigger is negative or stressful life events. At the cellular level, the trigger for panic attacks is thought to involve changes in sodium [A. I. Molosh, P. L. Johnson, S. D. Fitz, J. A. DiMicco, J. P. Herman, and A. Shekhar. Changes in central sodium and not osmolarity or lactate induce panic-like responses in a model of panic disorder. Neuropsychopharmacology 35(6, 2010): 1333-1347].

The neurological pathways that are involved in panic disorder comprise connections between many of the structures shown in FIG. 9, namely, the amygdala interacting with the parabrachial nucleus, periaqueductal gray, hippocampus, prefrontal cortex, locus ceruleus, and hypothalamus. Respiratory effects that may be associated with asthma co-morbidity are particularly mediated by signals through the parabrachial nucleus. As with migraine, the panic attack is self-sustaining after being triggered, but the positive feedback loops appear to involve autonomic pathways (e.g., with increased heart rate, blood pressure and respiration) and cognitive recognition (increased fear resulting from recognized increasing fear) to a greater extent than migraine [Peter P Roy-Byrne, Michelle G Craske, Murray B Stein. Panic disorder. Lancet 368(2006): 1023-1032]. Unless a migraine attack is coincident with the panic attack, the trigeminocervical complex and superior salivatory nucleus are not necessarily part of the positive feedback loop.

Currently, selective serotonin reuptake inhibitors (SSRIs) are the preferred treatment for panic disorder, on the basis of many positive placebo-controlled, randomized trials supporting the efficacy of six different drugs: fluoxetine, fluvoxamine, sertraline, paroxetine, citalopram, and escitalopram. However, patients with migraine are also treated with triptans, and potentially life-threatening Serotonin Syndrome may develop as the result of the combined administration of SSRIs and triptans [Randolph W. Evans. The FDA Alert on Serotonin Syndrome With Combined Use of SSRIs or SNRIs and Triptans: An Analysis of the 29 Case Reports. MedGenMed 9(3, 2007): 48]. Accordingly, there is a need for new anxiety disorders treatments, particularly in individuals with co-morbid migraine. The presently disclosed methods and devices involving vagal nerve stimulation (VNS) are intended as such a treatment. The present invention differs from other VNS treatments for anxiety disorders in that it may be performed non-invasively, including using magnetic stimulation to the vagus nerve, and in that it involves modulation of glutamate or glutamate receptors (e.g., Pathways 83 in FIG. 9). U.S. Pat. No. 5,899,922, entitled Manipulation of nervous systems by electric fields, to Loos and U.S. Pat. No. 5,782,874, entitled Method and apparatus for manipulating nervous systems, to Loos disclose the treatment of disorders that include panic attack. However, they differ from the present disclosure in that they use field electrodes that are placed away from the body, rather than the contact electrodes disclosed herein, they teach stimulation of the sympathetic nervous system rather than the vagus nerve, and they do not teach the use of magnetic stimulation. Patent application US20060064140, entitled Methods and systems for stimulating a trigeminal nerve to treat a psychiatric disorder, to Whitehurst et al. discloses nerve stimulation to treat panic disorder, but does not teach non-invasive stimulation and does not teach magnetic stimulation.

As described above, migraine headaches are due in part to hypoactivity of the sympathetic nervous system, as evidenced for example by reduced norepinephrine levels in migraineurs. More generally, in migraine there is an imbalance between the sympathetic and parasympathetic nervous systems in which the former is hypoactive and the latter is hyperactive. Stimulation of the vagus nerve as described herein is intended to restore the sympathetic/parasympathetic balance to a more normal range, for example by activating the locus ceruleus to increase sympathetic discharge and inhibit parasympathetic tone through its connections within the brainstem, or by activating a structure such as the hypothalmus that might restore autonomic balance. Such stimulation may also cause the release of catecholamines (epinephrine and/or norepinephrine) from the adrenal glands and/or from nerve endings that are distributed throughout the body, in which circulation primarily through the carotid artery delivers the catacholamines to the brain.

However, it is understood that the vagus nerve is not the only nerve or tissue that may be stimulated as a countermeasure against sympathetic hypoactivity or sympathetic/parasympathetic imbalance. Commonly assigned co-pending patent applications US20070106338, entitled Direct and Indirect Control of Muscle for the Treatment of Pathologies to ERRICO and US20100249873, entitled Direct and Indirect Control of Muscle for the Treatment of Pathologies, to ERRICO, contemplate the electrical stimulation of nerves emanating from a patient's sympathetic nerve chain, as well as stimulation of the nerve plexus of fibers emanating from both the sympathetic nerve chain and the tenth cranial nerve (the vagus nerve), such as the hepatic plexus. U.S. Pat. No. 7,418,292 to SHAFER also relates to electrical stimulation of neurons of the sympathetic nervous system. U.S. Pat. No. 7,877,146, entitled Methods of treating medical conditions by neuromodulation of the sympathetic nervous system, to Rezai et al is concerned with the neuromodulation of the sympathetic nervous system to treat respiratory and pulmonary conditions, but mentions treatment of migraine within a long list of diseases that may be treated. The stimulation of a branch of the greater splanchnic nerve also causes release of catecholamines from the adrenal gland, in addition to direct electrical stimulation of that gland [Xi Guo and Arun R. Wakade. Differential secretion of catecholamines in response to peptidergic and cholinergic transmitters in rat adrenals. Journal of Physiology 475(3, 1994):539-545].

In such applications involving sympathetic stimulation, the stimulating electrode would ordinarily be implanted invasively, but it is also possible to implant the stimulating electrodes percutaneously [Patent application US20100234907, entitled Splanchnic Nerve Stimulation for Treatment of Obesity, to Dobak]. Considering that the devices and methods disclosed herein are intended for the stimulation of deep nerves, in situations where the introduction of electrodes percutaneously is feasible, the presently disclosed non-invasive devices may work as well.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating a primary headache in a patient, the method comprising:
   positioning a housing in contact with an outer skin surface of a neck of the patient;
   generating an electrical impulse with a power supply housed within the housing; and
   transmitting, as the housing is in contact with the outer skin surface of the neck of the patient, the electrical impulse from the housing non-invasively and transcutaneously through the outer skin surface of the neck of the patient to a nerve fiber of a vagus nerve in the patient, wherein the electrical impulse at least partially relieves a symptom of the primary headache and thereby treats the primary headache.

2. The method of claim 1, wherein the transmitting comprises transcutaneously passing an electric current through the outer skin surface of the patient to a target region within the patient.

3. The method of claim 2, further comprising:
   generating an electric field at or near the housing; and
   shaping the electric field such that the electric field modulates a nerve at the target region; and wherein the electric field does not substantially modulate a nerve or muscle between the outer skin surface and the target region.

4. The method of claim 1, wherein the positioning comprises positioning an electrically permeable surface of the housing adjacent to the skin surface of the neck of the patient and the generating comprises generating the electrical impulse with a power source and a pulse generator located within the housing.

5. The method of claim 4, wherein the transmitting comprises applying the electrical impulse to an electrode within the housing and transmitting the electrical impulse through a conductive gel within the housing to the electrically permeable surface.

6. The method of claim 1, wherein the electrical impulse at least partially relieves the symptom within 30 minutes of the transmitting.

7. The method of claim 1, wherein the electrical impulse is transmitted transcutaneously through the outer skin surface of the patient to generate an electrical impulse at or near the nerve fiber.

8. The method of claim 1, wherein the transmitting comprises generating a magnetic field exterior to the patient to induce an electrical impulse at or near the nerve fiber within the patient.

9. The method of claim 1, wherein the nerve fiber is at least approximately 1-2 cm below the outer skin surface of the patient.

10. The method of claim 1, wherein the one or more electrical impulse is substantially constrained from modulating a nerve in a region between the outer skin surface and the selected nerve fiber.

11. The method of claim 1 wherein the primary headache is migraine.

12. The method of claim 1 wherein the primary headache is cluster headache.

13. The method of claim 1 wherein the primary headache is tension-type headache.

14. The method of claim 1, wherein the primary headache is trigeminal autonomic cephalalgia.

15. The method of claim 1, wherein the nerve fiber is an afferent parasympathetic nerve.

16. The method of claim 1, wherein the electrical impulse comprises bursts of pulses with a frequency from about 5 Hz to about 100 Hz.

17. The method of claim 1, wherein the electrical impulse comprises bursts from 1 to 20 pulses with each of the pulses from about 50 to about 1000 microseconds in duration.

18. The method of claim 1, wherein the electrical impulse increases an inhibitory neurotransmitter in a brain of the patient.

19. A method of treating a primary headache in a patient, the method comprising:
   positioning a housing in contact with an outer skin surface of a neck of the patient;
   generating an electrical impulse with a power supply housed within the housing;
   transmitting, as the housing is in contact with the outer skin surface of the neck of the patient, the electrical impulse from the housing non-invasively and transcutaneously through the outer skin surface of the patient to a nerve fiber of a vagus nerve, wherein the nerve fiber is, at least approximately 1-2 cm below the outer skin surface of the patient; and wherein the electrical impulse at least partially relieves a symptom of the primary headache and thereby treats the primary headache.

20. The method of claim 19 wherein the transmitting step is carried out by transcutaneously passing an electric current through the outer skin surface of the patient to a target region within the patient.

21. The method of claim 20, further comprising:
   generating an electric field at or near the housing; and
   shaping the electric field such that the electric field modulates a nerve at the target region; and wherein the electric field does not substantially modulate a nerve or muscle between the outer skin surface and the target region.

22. The method of claim 19, wherein the positioning comprises positioning an electrically permeable surface of the housing adjacent to the skin surface of the neck of the patient and the generating comprises generating the electrical impulse with a power source and a pulse generator located within the housing.

23. The method of claim 22, wherein the transmitting comprises applying the electrical impulse to an electrode within the housing and transmitting the electrical impulse through a conductive gel within the housing to the electrically permeable surface.

24. The method of claim 19, wherein the electrical impulse at least partially relieves the symptom within 30 minutes of the transmitting.

25. The method of claim 19, wherein the electrical impulse is transmitted transcutaneously through the outer skin surface of the patient to generate an electrical impulse at or near the nerve fiber.

26. The method of claim 19, wherein the transmitting comprises generating a magnetic field exterior to the patient to induce an electrical impulse at or near the nerve fiber within the patient.

27. The method of claim 19 wherein the electrical impulse is substantially constrained from modulating a nerve in a region between the outer skin surface and the nerve fiber.

28. The method of claim 19 wherein the primary headache is migraine.

29. The method of claim 19 wherein the primary headache is cluster headache.

30. The method of claim 19 wherein the nerve fiber is an afferent parasympathetic nerve.

31. The method of claim 19, wherein the electrical impulse comprises bursts of pulses with a frequency from about 5 Hz to about 100 Hz.

32. The method of claim 19, wherein the electrical impulse comprises bursts from 1 to 20 pulses with each of the pulses from about 50 to about 1000 microseconds in duration.

33. The method of claim 19 wherein the primary headache is tension-type headache.

34. The method of claim 19, wherein the primary headache is trigeminal autonomic cephalalgia.

35. The method of claim 19, wherein the electrical impulse increases an inhibitory neurotransmitter in a brain of the patient.

\* \* \* \* \*